US012594285B2

(12) United States Patent
Latefi

(10) Patent No.: US 12,594,285 B2
(45) Date of Patent: \*Apr. 7, 2026

(54) COMPOSITIONS AND METHODS FOR PROTECTING AGAINST AIRBORNE PATHOGENS AND IRRITANTS

(71) Applicant: APPLIED BIOLOGICAL LABORATORIES, INC., Brooklyn, NY (US)

(72) Inventor: Nazlie Latefi, New York, NY (US)

(73) Assignee: APPLIED BIOLOGICAL LABORATORIES, INC., New York, NY (US)

(\*) Notice: Subject to any disclaimer, the term of this patent is extended or adjusted under 35 U.S.C. 154(b) by 0 days.

This patent is subject to a terminal disclaimer.

(21) Appl. No.: 17/497,813

(22) Filed: Oct. 8, 2021

(65) Prior Publication Data

US 2022/0047614 A1     Feb. 17, 2022

Related U.S. Application Data

(63) Continuation of application No. 15/691,648, filed on Aug. 30, 2017, now Pat. No. 12,447,166, which is a continuation-in-part of application No. 15/442,604, filed on Feb. 24, 2017, now Pat. No. 12,447,200.

(60) Provisional application No. 62/299,775, filed on Feb. 25, 2016.

(51) Int. Cl.
| | |
|---|---|
| *A61K 31/7012* | (2006.01) |
| *A61K 9/00* | (2006.01) |
| *A61K 31/352* | (2006.01) |
| *A61K 31/7016* | (2006.01) |
| *A61K 33/30* | (2006.01) |
| *A61K 33/34* | (2006.01) |
| *A61K 33/38* | (2006.01) |
| *A61K 36/28* | (2006.01) |
| *A61K 36/328* | (2006.01) |
| *A61K 36/53* | (2006.01) |
| *A61K 36/752* | (2006.01) |
| *A61K 38/17* | (2006.01) |
| *A61K 38/40* | (2006.01) |
| *A61K 38/47* | (2006.01) |
| *A61K 45/06* | (2006.01) |
| *A61K 47/10* | (2017.01) |
| *A61K 47/26* | (2006.01) |
| *A61K 47/44* | (2017.01) |
| *A61P 11/00* | (2006.01) |
| *A61P 31/00* | (2006.01) |
| *C12N 9/24* | (2006.01) |

(52) U.S. Cl.
CPC ........ *A61K 31/7012* (2013.01); *A61K 9/0019* (2013.01); *A61K 9/0043* (2013.01); *A61K 9/0073* (2013.01); *A61K 31/352* (2013.01); *A61K 31/7016* (2013.01); *A61K 33/30*

(2013.01); *A61K 33/34* (2013.01); *A61K 33/38* (2013.01); *A61K 36/28* (2013.01); *A61K 36/328* (2013.01); *A61K 36/53* (2013.01); *A61K 36/752* (2013.01); *A61K 38/1774* (2013.01); *A61K 38/40* (2013.01); *A61K 38/47* (2013.01); *A61K 45/06* (2013.01); *A61K 47/10* (2013.01); *A61K 47/26* (2013.01); *A61K 47/44* (2013.01); *A61P 11/00* (2018.01); *A61P 31/00* (2018.01); *C12Y 302/01017* (2013.01); *C12N 9/24* (2013.01); *C12N 2760/16263* (2013.01)

(58) Field of Classification Search
CPC .............. A61K 31/7012; A61K 9/0019; A61K 9/0043; A61K 9/0073; A61K 31/352; A61K 31/7016; A61K 33/30; A61K 33/34; A61K 33/38; A61K 36/28; A61K 36/328; A61K 36/53; A61K 36/752; A61K 38/1774; A61K 38/40; A61K 38/47; A61K 45/06; A61K 47/10; A61K 47/26; A61K 47/44; A61P 11/00; A61P 31/00; C12Y 302/01017; C12N 9/24; C12N 2760/16263
See application file for complete search history.

(56) References Cited

U.S. PATENT DOCUMENTS

| | | | | |
|---|---|---|---|---|
| 2,156,254 A | * | 4/1939 | Manchey ............. | A61K 9/0043 514/781 |
| 4,734,729 A | | 3/1988 | Wolfgang et al. | |
| 5,576,299 A | | 11/1996 | Ando et al. | |
| 5,993,089 A | | 11/1999 | Weaver et al. | |

(Continued)

FOREIGN PATENT DOCUMENTS

| | | |
|---|---|---|
| CN | 1248603 A | 3/2000 |
| CN | 1679926 A | 10/2005 |

(Continued)

OTHER PUBLICATIONS

Miriam Kuipers, et al., Design and Fungicidal Activity of Mucoadhesive Lactoferrin Tablets for the Treatment of Oropharyngeal Candidosis, 9 Drug Delivery 31 (Year: 2002).\*
Gabriella Cisani, et al, Inhibition of Herpes Simplex Virus-Induced Cytopathic Effect by Modified Hen Egg-white Lysozymes, 10 Curr. Microbiol. 35 (Year: 1984).\*
Abstract—44th Annual Meeting of the Brazilian Society for Biochemistry and Molecular Biology, Aug. 2015, p. 1 (Year: 2015).\*
Abouhmad et al., "T4 lysozyme fused with cellulos-binding module for antimicrobial cellulosic wound dressing materials," Journal of Applied Microbiology, vol. 121, pp. 115-125 (2016).

(Continued)

*Primary Examiner* — Sean M Basquill
(74) *Attorney, Agent, or Firm* — Jonathan Ball; Greenberg Traurig, LLP

(57) ABSTRACT

The present disclosure features methods and compositions for enhancing the ability of the respiratory membranes to filter airborne pathogens and protect a subject from respiratory infections that result from inhalation or ingestion of such pathogens. In particular, the disclosure provides antimicrobial compositions that prevent and treat respiratory infections caused by bacteria, fungi, and viruses.

8 Claims, 33 Drawing Sheets

(56) References Cited

U.S. PATENT DOCUMENTS

| | | | |
|---|---|---|---|
| 6,020,333 | A | 2/2000 | Berque |
| 6,093,417 | A | 7/2000 | Petrus |
| 6,183,742 | B1 | 2/2001 | Kiczka |
| 6,329,339 | B1 | 12/2001 | Pompei et al. |
| 6,365,156 | B1 | 4/2002 | Lee |
| 6,503,881 | B2 | 1/2003 | Krieger et al. |
| 6,716,813 | B2 | 4/2004 | Lim et al. |
| 7,459,283 | B2 | 12/2008 | Wertz et al. |
| 7,662,607 | B2 | 2/2010 | Wang et al. |
| 7,846,430 | B2 | 12/2010 | Ferrari |
| 7,989,003 | B2 | 8/2011 | Hensley et al. |
| 8,263,138 | B2 | 9/2012 | Perraudin |
| 2003/0134779 | A1 | 7/2003 | Diarra et al. |
| 2003/0219402 | A1 | 11/2003 | Rutter |
| 2004/0063617 | A1* | 4/2004 | Huang ................. C07K 14/415 514/2.3 |
| 2005/0158327 | A1 | 7/2005 | Mohapatra et al. |
| 2005/0245467 | A1 | 11/2005 | Berg |
| 2006/0159671 | A1 | 7/2006 | Fischetti |
| 2007/0116750 | A1 | 5/2007 | Wolcott |
| 2009/0142298 | A1 | 6/2009 | Shatunovskiy |
| 2010/0143490 | A1 | 6/2010 | Roberts et al. |
| 2010/0160245 | A1 | 6/2010 | Lines |
| 2010/0209419 | A1* | 8/2010 | Bhushan ................. A61P 35/00 424/94.1 |
| 2010/0233129 | A1 | 9/2010 | Fichot |
| 2011/0015120 | A1 | 1/2011 | Bortolin |
| 2011/0052727 | A1 | 3/2011 | Polansky |
| 2011/0059919 | A1 | 3/2011 | Grassauer et al. |
| 2011/0301077 | A1 | 12/2011 | Perraudin |
| 2012/0171164 | A1 | 7/2012 | Wittke et al. |
| 2013/0028882 | A1* | 1/2013 | Colman ............... A61K 36/185 514/54 |
| 2013/0034542 | A1 | 2/2013 | Ganter et al. |
| 2013/0058912 | A1 | 3/2013 | Griswold et al. |
| 2013/0309220 | A1 | 11/2013 | Matalon |
| 2014/0121237 | A1 | 5/2014 | Tripp et al. |
| 2015/0093371 | A1 | 4/2015 | Colman et al. |
| 2016/0022713 | A1 | 1/2016 | Wang et al. |
| 2016/0144004 | A1 | 5/2016 | Pellico |
| 2017/0065720 | A1 | 3/2017 | Nguyen et al. |
| 2017/0246262 | A1 | 8/2017 | Latefi |
| 2017/0360815 | A1* | 12/2017 | Latefi ................. A61K 38/1774 |

FOREIGN PATENT DOCUMENTS

| | | | |
|---|---|---|---|
| CN | 101190331 | A | 6/2008 |
| CN | 100493605 | C | 6/2009 |
| CN | 101947278 | A | 1/2011 |
| EP | 2845606 | A1 | 3/2015 |
| GB | 981260 | A1 | 1/1965 |
| GB | 1171183 | A | 11/1969 |
| GB | 1174187 | A | 12/1969 |
| GB | 1431709 | | 4/1976 |
| GB | 2374008 | A | 10/2002 |
| JP | 2001525814 | A | 12/2001 |
| JP | 2009102370 | A | 5/2009 |
| JP | 2013515022 | A | 5/2013 |
| KR | 20100132737 | A | 12/2010 |
| KR | 101119538 | B1 | 2/2012 |
| KR | 20120065654 | A | 6/2012 |
| RU | 2504396 | C1 | 1/2014 |
| RU | 2535053 | C2 | 12/2014 |
| RU | 2548803 | C2 | 4/2015 |
| WO | 9527736 | A1 | 10/1995 |
| WO | 1998006425 | A1 | 2/1998 |
| WO | WO-0032171 | A2 * | 6/2000 ............ A61K 9/006 |
| WO | 2001092336 | A1 | 12/2001 |
| WO | 2003/051281 | A3 | 6/2003 |
| WO | 2006028497 | A2 | 3/2006 |
| WO | WO-2009009156 | A2 * | 1/2009 .......... A61K 31/573 |
| WO | 2011130799 | A1 | 10/2011 |
| WO | 2012022734 | A2 | 2/2012 |
| WO | 2014151523 | A1 | 9/2014 |
| WO | WO15092041 | A1 | 6/2015 |
| WO | 2017147540 | A1 | 8/2017 |

OTHER PUBLICATIONS

International Search Report and Written Opinion to corresponding International Application No. PCT/US2017/019535 mailed May 8, 2017 (12 pages).

Lei et al., "Dynamic Spongy Microporous Films to Load Lysozyme for Antibacterial Coating," Acta Polymerica Sinica, No. 5, pp. 744-751 (2017).

Marlin et al., "A Soluble Form of Intercellular Adhesion Molecule—1 Inhibits Rhinovirus Infection," Nature; London, vol. 344, No. 6261, pp. 70-72 (1990).

Muscedere et al., "Prevention of nosocomial infections in critically ill patients with lactoferrin (Prevail study): study protocol for a randomized controlled trial," Trials, vol. 17, No. 474 (2016).

Pammi et al., "Oral lactoferrin for the treatment of sepsis and necrotizing enterocolitis in neonates (Review)," Issue 10, 14 pages (2011).

Samaranayake et al., "Synergistic activity of lysozyme and antifungal agents against Candida albicans biofilms on denture acrylic surfaces," ScienceDirect, vol. 54, pp. 115-126 (2009).

Turner et al., "Efficacy of Tremacamra, a Soluble Intercellular Adhesion Molecule 1, for Experimental Rhinovirus Infection: A randomized Clinical Trial," JAMA, May 19, 1999, vol. 281, No. 19, pp. 1797-1804.

Search Report and Written Opinion in corresponding Singapore Patent Application No. 11201806868T, dated Nov. 28, 2019 (13 pages).

Search Report for corresponding Russian Patent Application No. 2018133581 (2 pages).

Office Action for corresponding Russian Patent Application No. 2018133581, issued on Aug. 11, 2020 (5 pages.

Yulish, et al., "Factors of immunity in respiratory infections and methods for their activating in aid of a pediatrist," 2010, vol. 5, No. 6, pp. 63-67 (English Abstract).

First Examination Report for corresponding Indian Application No. 201817032360, dated Jun. 25, 2020 (6 pages).

Wakabayashi et al., "Lactoferrin for prevention of common viral infections," Journal of Infection and Chemotherapy, Aug. 30, 2014, vol. 20, 666-671.

Al-Nabulsi et al., "Enhancing the antimicrobial effects of bovine lactoferrin against Escherichia coli 0157:h7 be cation chelation, NaCl and temperature," Journa Iof Applied Microbiology, Dec. 12, 2005, vol. 100, 244-255.

Davis et al., "Quercetin reduces susceptibility to influenza infection following stressful exercise," American Journal of Physiology-Regulatory, Integrative and Comparative Physiology, Aug. 1, 2008, vol. 295 R505-R509.

Kim et al., Inhibition of influenza virus replication by plant-derived isoquercetin, Antiviral Research, Aug. 31, 2010, vol. 88, 227-235.

Martin Koenighofer et al: "Carrageenan nasal spray in virus confirmed common cold: individual patient data analysis of two randomized controlled trials", Multidisciplinary Respiratory Medicine, Biomed Central Ltd, London, UK, vol. 9, No. 1, Nov. 12, 2014 (Nov. 12, 2014), p. 57.

Jefferson Tom: "Advances in the diagnosis and management of influenza", Current Infectious Disease Reports, Current Science, Philadelphia, PA, US, vol. 4, No. 3, May 1, 2002 (May 1, 2002), pp. 206-210.

Schiller, L., "Osmotic Effects of Polyethylene Glycol," Gastroenterology, vol. 94, No. 4, p. 933-941. Apr. 1988.

* cited by examiner

Effects of HRV3 treatment on LDH release
upon Rhinovirus A16 infection

Effects of HRV4 treatment on LDH release
upon Rhinovirus A16 infection

FIG. 13

Influenza H1N1 Replication

Influenza H1N1 Replication

Influenza H1N1 Replication

Influenza H1N1 Replication

Effects of Formulations on MCC at 48 Hours upon HRV-A16 Infection

Effect of Formulations on Apical H1N1 Genome Copy Number at D1 and D2

Effects of Formulations on TEER upon H1N1 Infection

COMPOSITIONS AND METHODS FOR PROTECTING AGAINST AIRBORNE PATHOGENS AND IRRITANTS

This application is a continuation claiming the benefit of and priority to U.S. application Ser. No. 15/691,648, filed Aug. 30, 2017, which is a continuation-in-part of U.S. application Ser. No. 15/442,604 filed Feb. 24, 2017, which claims priority to and the benefit of under 35 U.S.C. § 119(e) to provisional application Ser. No. 62/299,755, filed Feb. 25, 2016, the entire contents of each application are hereby incorporated by reference in their entirety.

FIELD OF THE DISCLOSURE

The disclosure relates to compositions and methods of augmenting the health and filtering capabilities of upper respiratory epithelial and mucous membranes. In particular, the disclosure relates to compositions and methods for protecting the epithelial and mucous membranes of a subject from infection by airborne pathogens, such as viruses, bacteria, and fungi, and irritation from undesirable airborne particles such as allergens, irritants, or odorants. The disclosure further relates to compositions for application to the respiratory tract (e.g., the nasal and oral mucosa, etc.) of a human for prophylaxis of microbial and viral infections, particularly human rhinovirus (HRV) and human influenza virus infections.

BACKGROUND

Respiratory infections typically occur when airborne pathogens come into contact with mucous membranes (e.g., nasal membranes, nasal hairs, esophageal membranes, etc.) via inhaled or ingested liquid or aerosol droplets. Inhalation or ingestion of pathogens through the nose or mouth is a primary cause of respiratory disease and may also cause systemic disease such as poliomyelitis or foot and mouth disease. Airborne pathogens may enter the lungs after inhalation or ingestion, or they may bind receptors found on nasal and other membranes throughout the upper and lower respiratory tracts which serve as an entry points by which pathogens, allergens, or irritants can enter into the bloodstream and cause respiratory, as well as other, types of infection or allergic reaction. Unfortunately, there is no convenient, effective way to minimize or prevent infection or allergy by inhaled or ingested microorganisms. Therefore, there is an urgent need to develop new compositions and methods to protect against airborne pathogens, allergens, and irritants, and particularly against viruses, particularly human rhinovirus (HRV), human influenza virus, or both.

SUMMARY OF INVENTION

In accordance with the foregoing objectives and others, the present disclosure features compositions, such as nasal sprays, oral sprays, oral rinses, lozenges, and the like, and associated methods of using such compositions for enhancing the ability of the epithelial membranes to filter certain airborne pathogens. In particular, the disclosure provides antimicrobial compositions that prevent and treat respiratory infections and allergies caused by irritants, allergens, bacteria, fungi, and viruses. In preferred implementations, the compositions protect a subject from viral infections, particularly from human rhinovirus and/or human influenza virus.

In one aspect of the invention, a composition is provided for prophylaxis or treatment of a human subject suffering from, or at risk of suffering from, a respiratory infection. The composition may comprise one or more antimicrobial or antiviral compounds dispersed in a carrier, typically, but not necessarily, a liquid carrier. The liquid carrier is ideally, but not necessarily, of suitable rheology to be sprayed as an aerosol or fine mist. The composition may comprise one or more ingredients selected from the group consisting of an emollient, an occlusive, a humectant, a carrier, an excipient, an emulsifier, and an essential oil. In some embodiments, the composition for prophylaxis or treatment of respiratory infection may comprise active ingredient that combat infection against viruses that bind intercellular adhesion molecule 1 (ICAM-1) and/or viruses that bind sialic acid (or extracellular portions thereof). In some embodiments, the pharmaceutical composition for preventing or treating respiratory infection may comprise a pharmaceutically acceptable carrier and at least two (e.g., two, three, four) active (e.g., antimicrobial and/or antiviral, etc.) agents selected from lactoferrin (e.g., apolactoferrin, etc.), lysozyme, ICAM-1 (e.g., soluble ICAM-1, etc.), sialic acid (e.g., sialyllactose, etc.), and a neuraminidase inhibitor (e.g., quercetin, etc.). In one implementation, a composition is provided for prophylaxis or treatment of a human subject suffering from, or at risk of suffering from, infection of the respiratory tract with human rhinovirus (HRV) comprising, in a suitable liquid carrier: (i) soluble ICAM-1 ("sICAM-1") and/or an ICAM-1 inhibitor; (ii) lysozyme; and (iii) lactoferrin (e.g., apolactoferrin, etc.). In another implementation, a composition is provided for prophylaxis or treatment of a human subject suffering from, or at risk of suffering from, infection of the respiratory tract with human influenza virus comprising, in a suitable liquid carrier: (i) sialic acid (e.g., sialyllactose, etc.); (ii) lysozyme; (iii) lactoferrin; and (iv) optionally, a neuraminidase inhibitor such as, for example, quercetin. In yet another implementation, a composition is provided for prophylaxis or treatment of a human subject suffering from, or at risk of suffering from, infection of the respiratory tract with human rhinovirus (HRV) and human influenza virus comprising, in a suitable liquid carrier: (i) soluble ICAM-1 (sICAM-1) and/or an ICAM-1 inhibitor; (ii) lysozyme; (iii) lactoferrin, (iv) sialic acid and/or a derivate therefore (e.g., sialyllactose, etc.); and (v) optionally, a neuraminidase inhibitor. Any of the compositions according to these embodiments, may further comprise one or more of zinc peroxide, copper, and silver. Any of the compositions according to these embodiments, may further comprise carrageenan. Any of the compositions according to these embodiments, may further comprise one or more of IgA, IgG, and IgM. The compositions may further comprise one or more ingredients selected from the group consisting of marshmallow extract, Calendula extract, citrus peel extract, honey extract, rosemary extract, myrrh extract, *Helichrysum* extract, arrowroot extract, neem oil, vitamin C, vitamin E, and grapefruit seed extract. The carrier may be aqueous, and may include one or more pharmaceutically acceptable excipients, including, without limitation, diluents, buffering agents, pH adjusters (e.g., citric acid, etc.), thickeners and suspending agents (e.g., gum acacia, xanthan gum, hydroxypropylmethylcellulose, microcrystalline cellulose, sodium carboxymethylcellulose, etc.), rheology modifiers, preservatives (e.g., phenethyl alcohol, benzalkonium chloride, sodium EDTA, etc.), isotonicity adjusters (e.g., sodium chloride, polyols, sucrose, etc.), humectants (e.g., glycerin, etc.), surfactants (e.g., polysorbates, such as polysorbate 80, sucrose palmitate, glyceryl stearate, glyceryl stearate citrate, acetylated hydrogenated vegetable glyceride, etc.), and taste modifiers, to name a few. Any excipients should be compatible with the human mucosa and epithelium, and should not cause excessive drying or irritation to the mucosa or epithelium. The excipients should also account for the fact that water will tend to evaporate at body temperature and as such a secondary solvent may be included to aid in maintaining the soluble components in solution. The carrier may include a polyol, such as a $C_2$-$C_8$ polyol, including without limitation, glycerin, propylene glycol, 1,3-propane diol, butylene glycol, 1,4-butane diol, erythritol, threitol, arabitol, xylitol, mannitol, sorbitol, pentylene glycol, hexylene glycol, caprylyl glycol, hydrogenated starch hydrolysates, isomalt, maltitol, and the like. The compositions may comprise an amount of an alcohol, such as ethanol, provided it is in an amount that does not irritate or dry the mucosa. In some embodiments, the compositions are free of ethanol. In one embodiment, the carrier is an aqueous carrier including from about 1-95% or from about 5-50% or from about 10-40% or from about 15-35% or from about 20-30% 1,3-propanediol, on a (v/v), (w/v), or (w/w) basis. In some embodiments, the composition may have a kinematic viscosity ranging from about 1-1,500 or from about 5-1,000 or from about 10-750 or from about 20-500 centiStokes ($mm^2$/s). The compositions may have a Newtonian or non-Newtonian rheology. The compositions may be, for example, shear thinning and/or thixotropic, such that they readily flow through a spray nozzle and form a mist of suitable droplet size on shearing, but thicken in situ to form a film on the mucosa which is resistant to clearance from the nasal or oral cavity such that the active remain on the mucosa for a time sufficient to neutralize pathogens in contact with the mucosa. Typically, the composition will be of suitable viscosity to possess a residence time on the mucosa of the nasal or oral cavities of at least 1 minute, more preferably, at least 5, 10, 15, 20, 25, or 30 minutes following application. The composition should be semi-permeable in order to permit virions and other pathogens to penetrate the film and come into contact with the active ingredients, while possessing a sufficient barrier function to inhibit evaporation of water and volatile solvents in order to maintain the actives in solution.

The pharmaceutical composition may comprise lactoferrin and soluble ICAM-1. In some embodiments, lactoferrin and soluble ICAM-1 are the sole active agents. The lactoferrin (e.g., apolactoferrin, etc.) may be present in an amount of from about from about 0.5-5000 μg/mL and the soluble ICAM-1 may be present in an amount of from about 0.01-2000 μg/mL. In preferred embodiments, the pharmaceutical composition comprises a carrier that is from about 60-90% (v/v) water and from about 10-40% (or from 20-30%) (v/v) of a polyol (e.g., 1,3-propandiol, etc.). In some embodiments, the pharmaceutical composition may be used for the treatment or prophylaxis of a respiratory disease. In preferred embodiments, the composition may be used for the treatment of rhinovirus.

The pharmaceutical composition may comprise lysozyme and soluble ICAM-1. In some embodiments, lysozyme and soluble ICAM-1 are the sole active agents. The lysozyme may be present in an amount of from about from about 0.5-5000 μg/mL and the soluble ICAM-1 may be present in an amount of from about 0.25-20000 μg/mL. In preferred embodiments, the pharmaceutical composition comprises a carrier that is from about 60-90% (v/v) water and from about 10-40% (or from 20-30%) (v/v) of a polyol (e.g., 1,3-propandiol, etc.). In some embodiments, the pharmaceutical composition may be used for the treatment or prophylaxis of a respiratory disease. In preferred embodiments, the composition may be used for the treatment of rhinovirus.

The pharmaceutical composition may comprise lactoferrin (e.g., apolactoferrin, etc.), lysozyme and soluble ICAM-1. In some embodiments, lactoferrin, lysozyme and soluble ICAM-1 are the sole active agents. The lactoferrin (e.g., apolactoferrin, etc.) may be present in an amount of from about from about 0.5-5000 μg/mL, the lysozyme may be present in an amount of from about from about 0.5-5000 μg/mL and the soluble ICAM-1 may be present in an amount of from about 0.25-20000 μg/mL. In preferred embodiments, the pharmaceutical composition comprises a carrier that is from about 60-90% (v/v) water and from about 10-40% (or from 20-30%) (v/v) of a polyol (e.g., 1,3-propandiol, etc.). In some embodiments, the pharmaceutical composition may be used for the treatment or prophylaxis of a respiratory disease. In preferred embodiments, the composition may be used for the treatment of rhinovirus.

The pharmaceutical composition may comprise lactoferrin (e.g., apolactoferrin, etc.) and lysozyme. In some embodiments, lysozyme and lactoferrin are the sole active agents. The lactoferrin (e.g., apolactoferrin, etc.) may be present in an amount of from about from about 0.5-5000 μg/mL and the lysozyme may be present in an amount of from about from about 0.5-5000 μg/mL. In preferred embodiments, the pharmaceutical composition comprises a carrier that is from about 60-90% (v/v) water and from about 10-40% (or from 20-30%) (v/v) of a polyol (e.g., 1,3-propandiol). In some embodiments, the pharmaceutical composition may be used for the treatment or prophylaxis of a respiratory disease. In preferred embodiments, the composition may be used for the treatment of influenza.

The pharmaceutical composition may comprise lactoferrin (e.g., apolactoferrin, etc.) and sialic acid. In some embodiments, lysozyme and lactoferrin are the sole active agents. The lactoferrin (e.g., apolactoferrin, etc.) may be present in an amount of from about from about 0.5-5000 μg/mL and the sialic acid may be present in an amount of from about 0.01-2000 μg/mL (or from about 0.1-1000 μg/mL or from about 0.5-750 μg/mL) of sialic acid (e.g., sialyllactose, 6'-sialyllactose, 3-sialyllactose, 6'-sialyllactose and 3'-sialyllactose, etc.). In preferred embodiments, the pharmaceutical composition comprises a carrier that is from about 60-90% (v/v) water and from about 10-40% (or from 20-30%) (v/v) of a polyol (e.g., 1,3-propandiol, etc.). In some embodiments, the pharmaceutical composition may be used for the treatment or prophylaxis of a respiratory disease. In preferred embodiments, the composition may be used for the treatment of influenza.

The pharmaceutical composition may comprise lactoferrin (e.g., apolactoferrin, etc.), lysozyme, and sialic acid. In some embodiments, lysozyme and lactoferrin are the sole active agents. The lactoferrin (e.g., apolactoferrin, etc.) may be present in an amount of from about from about 0.5-5000 μg/mL, the lysozyme may be present in an amount of from about from about 0.5-5000 μg/mL, and the sialic acid may be present in an amount of from about 0.01-2000 μg/mL (or from about 0.1-1000 μg/mL or from about 0.5-750 μg/mL) of sialic acid (e.g., sialyllactose, 6'-sialyllactose, 3-sialyllactose, 6'-sialyllactose and 3'-sialyllactose, etc.). In preferred embodiments, the pharmaceutical composition comprises a carrier that is from about 60-90% (v/v) water and from about 10-40% (or from 20-30%) (v/v) of a polyol (e.g., 1,3-propandiol, etc.). In some embodiments, the pharmaceutical composition may be used for the treatment or prophylaxis of a respiratory disease. In preferred embodiments, the composition may be used for the treatment of influenza.

The pharmaceutical composition may comprise lactoferrin (e.g., apolactoferrin, etc.), lysozyme, a neuraminidase inhibitor (e.g., quercetin and isoforms thereof, isoquercetin, etc.), and sialic acid. In some embodiments, lysozyme, neuraminidase inhibitor, and lactoferrin are the sole active agents. The lactoferrin (e.g., apolactoferrin, etc.) may be present in an amount of from about from about 0.5-5000 μg/mL, the lysozyme may be present in an amount of from about from about 0.5-5000 μg/mL, the neuraminidase inhibitor may be present in an amount of from about 0.1-20 μM (or from 0.1-20 μM or from about 0.1-5 μM or from about 0.2-3 μM) neuraminidase inhibitor, and the sialic acid may be present in an amount of from about 0.01-2000 μg/mL (or from about 0.1-1000 μg/mL or from about 0.5-750 μg/mL) of sialic acid (e.g., sialyllactose, 6'-sialyllactose, 3-sialyllactose, 6'-sialyllactose and 3'-sialyllactose, etc.). In some embodiments, the lactoferrin and sialic acid and lysozyme are present in an amount such that the cytotoxicity of a mucous membrane affected by influenza (e.g., as measured by LDH release, etc.) is not increased when the composition is applied to the mucous membrane. In some embodiments, the pharmaceutical composition decreases the cytotoxicity of a mucous membrane to which the pharmaceutical composition is applied, as compared to an otherwise identical composition not comprising sialic acid and/or lactoferrin and/or lysozyme. In preferred embodiments, the pharmaceutical composition comprises a carrier that is from about 60-90% (v/v) water and from about 10-40% (or from 20-30%) (v/v) of a polyol (e.g., 1,3-propandiol, etc.). In some embodiments, the pharmaceutical composition may be used for the treatment or prophylaxis of a respiratory disease. In preferred embodiments, the composition may be used for the treatment of influenza. Typically the neuraminidase inhibitor is isoquercetin.

In some embodiments, the composition may comprise:
(i) about 0.00000001%-10% by weight ICAM-1 (e.g., soluble ICAM-1, etc.);
(ii) 0% (or from about 0.00000001%) to about 10% by weight of a neuraminidase inhibitor;
(iii) about 0.00000001% to about 10% by weight of sialic acid (e.g., sialyllactose, 2,3'-sialyllactose, and/or 2,6' sialyllactose, etc.);
(iv) about 0.00000001% to about 10% by weight of lysozyme; and
(v) about 0.00000001% to about 10% by weight of lactoferrin (e.g., apolactoferrin, etc.);
a pharmaceutically acceptable carrier and, optionally, one or more excipients.

In some embodiments, the composition may comprise:
(i) about 0.000001%-1% (or to about 0.1%) by weight ICAM-1 (e.g., soluble ICAM-1, etc.); and/or
(ii) 0% (or from about 0.000001%) to about 1% (or to about 0.1%) by weight of a neuraminidase inhibitor; and/or
(iii) about 0.000001% to about 0.001% (or to about 0.01%) by weight of sialic acid (e.g., sialyllactose, 2,3'-sialyllactose, and/or 2,6' sialyllactose); and/or
(iv) about 0.0001% to about 5% (or to about 1%) by weight of lysozyme; and/or
(v) about 0.00005% to about 5% (or to about 0.5%) by weight of lactoferrin (e.g., apolactoferrin, etc.);
a pharmaceutically acceptable carrier and, optionally, one or more excipients.

In some embodiments, the composition may comprise:
(i) about 0.0005%-0.05% by weight ICAM-1 (e.g., soluble ICAM-1, etc.); and/or (ii) 0% (or from about 0.005%) to about 0.05% by weight of a neuraminidase inhibitor; and/or
(iii) about 0.000005% to about 0.05% by weight of sialic acid (e.g., sialyllactose, 2,3'-sialyllactose, and/or 2,6' sialyllactose); and/or
(iv) about 0.0025% to about 0.25% by weight of lysozyme; and/or
(v) about 0.00005% to about 0.1% by weight of lactoferrin (e.g., apolactoferrin, etc.);
a pharmaceutically acceptable carrier and, optionally, one or more excipients.

The pharmaceutical composition may be used in a method of preventing or treating respiratory infection. The respiratory infection may be due to human rhinovirus and/or human influenza virus. In some embodiments, a composition for preventing or treating respiratory infection from human rhinovirus (HRV) may comprise:
(i) about 0.00000001% to about 10% by weight soluble ICAM-1;
(ii) about 0.000005% to about 10% by weight lysozyme; and
(iii) about 0.00000025% to about 10% by weight lactoferrin;
and a pharmaceutically acceptable carrier and, optionally, one or more excipients.

In some embodiments, a composition for preventing or treating respiratory infection from human rhinovirus (HRV) may comprise:
(i) about 0.000001%-1% (or to about 0.1%) by weight soluble ICAM-1;
(ii) about 0.0001% to about 5% (or to about 1%) by weight lysozyme; and
(iii) about 0.00005% to about 5% (or to about 0.5%) by weight lactoferrin;
and a pharmaceutically acceptable carrier and, optionally, one or more excipients.

In some embodiments, a composition for preventing or treating respiratory infection from human rhinovirus (HRV) may comprise:
(i) about 0.0005%-0.05% by weight soluble ICAM-1; and/or
(ii) about 0.0025% to about 0.25% by weight lysozyme; and/or
(iii) about 0.00005% to about 0.1% by weight lactoferrin;
and a pharmaceutically acceptable carrier and, optionally, one or more excipients.

In some embodiments, a composition for preventing or treating respiratory infection from human influenza virus may comprise:
(i) about 0.0000001% to about 10% by weight of said sialic acid (e.g., sialyllactose, etc.);
(ii) about 0.00000001% to about 10% by weight of said lysozyme;
(iii) about 0.00000001% to about 10% by weight of said lactoferrin; and
(iv) 0% (or from about 0.00000001%) to about 10% by weight of a neuraminidase inhibitor;
and a pharmaceutically acceptable carrier and, optionally, one or more excipients.

In some embodiments, a composition for preventing or treating respiratory infection from human influenza virus may comprise:
(i) about 0.000005% to about 0.05% by weight of said sialic acid (e.g., sialyllactose, etc.);
(ii) about 0.0001% to about 5% (or to about 1%) by weight of said lysozyme;

(iii) about 0.00005% to about 5% (or to about 0.5%) by weight of said lactoferrin; and (v) 0% (or from about 0.01%) to about 10% by weight of a neuraminidase inhibitor;

and a pharmaceutically acceptable carrier and, optionally, one or more excipients.

In some embodiments, a composition for preventing or treating respiratory infection from human influenza virus may comprise:

(i) about 0.000005% to about 0.05% by weight of said sialic acid (e.g., sialyllactose, etc.); and/or (ii) about 0.0025% to about 0.25% by weight of said lysozyme; and/or (iii) about 0.00005% to about 0.1% by weight of said lactoferrin; and/or (vi) 0% (or from about 0.000001%) to about 1% (or to about 0.1%) by weight of a neuraminidase inhibitor;

and a pharmaceutically acceptable carrier and, optionally, one or more excipients.

In some embodiments, the compositions of the invention will be aqueous solutions or suspensions comprising from about 0.5-5000 µg/mL (or from about 1-1000 µg/mL or from about 5-500 µg/mL) of lactoferrin (e.g., apolactoferrin, etc.). In some embodiments, the compositions of the invention will be aqueous solutions or suspensions comprising from about 0.25-20000 µg/mL (or from about 0.25-10000 µg/mL or from about 1-5000 µg/mL or from about 25-2500 µg/mL or from about 1000-12000 µg/mL) of lysozyme. In some embodiments, the compositions of the invention will be aqueous solutions or suspensions comprising from about 0.01-2000 µg/mL (or about 0.01-1000 µg/mL or from about 0.1-600 µg/mL or from about 0.1-100 µg/mL or from about 0.5-50 µg/mL) of ICAM-1 (e.g., soluble ICAM-1, etc.). In some embodiments, the compositions of the invention will be aqueous solutions or suspensions comprising from about 0.01-2000 µg/mL (or from about 0.1-1000 µg/mL or from about 0.5-750 µg/mL) of sialic acid (e.g., sialyllactose, etc.). In some embodiments the composition comprises a concentration of 6'-sialylllactose of about 0.01-2000 µg/mL (or from about 0.1-1000 µg/mL or from about 0.5-750 µg/mL) and a concentration of 3'-sialyllactose of about 0.01-2000 µg/mL (or from about 0.1-1000 µg/mL or from about 0.5-750 µg/mL). In some embodiments, the compositions of the invention will be aqueous solutions or suspensions comprising from about 0.005-1000 µg/mL (or from about 0.5-500 µg/mL or from about 0.25-375 µg/mL) of 3' sialyllactose and/or from about 0.005-1000 µg/mL (or from about 0.5-500 µg/mL or from about 0.25-375 µg/mL) of 6' sialyllactose. In some embodiments, the compositions will comprise from about 0.1-20 µM (or from 0.1-20 µM or from about 0.1-5 µM or from about 0.2-3 µM) neuraminidase inhibitor. In some embodiments, the compositions will comprise from about 0.1-20 µM (or from 0.1-20 µM or from about 0.1-5 µM or from about 0.2-3 µM) quercetin.

The pharmaceutical compositions according to the invention may be in the form of a nasal spray, nasal drops, oral spray, oral rinse, or lozenge. The carrier of the pharmaceutical composition may be selected to provide residence time of the composition on the nasal and/or oral mucosa of at least 1 minute, or at least 5 minutes, or at least 10 minutes, or at least 15 minutes, or at least 20 minutes, or at least 25 minutes, or at least 30 minutes following application. In some embodiments, the composition for application to the nasal or oral mucosa comprises one or more antiviral and/or antimicrobial agents dispersed in a liquid carrier comprising from about 1-99% (v/v) water or from about 60-90% (v/v) water and from about 10-40% (or from 20-30%) (v/v) of a polyol. In some embodiments, the pharmaceutically acceptable carrier is an aqueous solution comprising from about 5-50% (v/v), or from about 10-40% (v/v), or from about 15-35% (v/v), or from about 20-30% (v/v) 1,3-propanediol. The composition may be capable of being sprayed or ingested onto the mucosa, and is adapted to remain on the mucosa for at least 5 minutes (or at least 10 minutes, or at least 15 minutes, or at least 20 minutes, or at least 25 minutes, or at least 30 minutes) following application without substantially irritating or drying the mucosa.

Methods for prophylaxis and/or treatment of various viral infections are provided. In some embodiments, the method for prophylaxis and/or treatment of human rhinovirus infection, comprises applying any of the composition described herein to the nasal and/or oral mucosa of an individual in need thereof. In some embodiments, the nasal and/or oral mucosa of individuals in need thereof has human rhinovirus in contact therewith.

In one aspect, the invention provides for a pharmaceutical composition for preventing or treating subjects suffering from or at risk of suffering from a respiratory infection comprising: one or more antimicrobial or antiviral compounds; and a base mixture comprising one or more ingredients selected from the group consisting of a carrier, an emollient, an occlusive, a humectant, a polyol, an emulsifier, a preservative, a thickener or suspending agent, a surfactant, a pH adjuster, an isotonicity agent, and an essential oil. In an embodiment, the antimicrobial or antiviral compound is one or more selected from the group consisting of an antibody such as IgA, IgG, or IgM, a soluble ICAM-1, an ICAM-1 inhibitor, sialic acid, a neuraminidase inhibitor, lactoferrin, a lysozyme, zinc, zinc compounds, silver, silver compounds, copper, copper compounds, and combinations thereof. In an embodiment, the neuraminidase inhibitor is selected from the group consisting of quercetin, oseltamivir, zanamivir, laninamivir, and peramivir. In an embodiment, the ICAM-1 inhibitor is selected from the group consisting of an anti-ICAM-1 antibody, cytokine, CD11a, ezrin (EZR), CD18, glycyrrhetinic acid, pyrrolidinedithiocarbamate, NFkB activation inhibitor, heterocyclic thiazole, lipoic acid, efalizumab, 4-[(4-Methylphenyl)thio]thieno[2,3-c]pyridine-2-carboxamide, silibinin, stilbenes, (+)-epigalloyl-catechin-gallate [(+)-EGCG], and combinations thereof. In an embodiment, the one or more antimicrobial or antiviral compounds include soluble ICAM-1 and sialic acid (e.g., sialyllactose, 3' sialyllactose, and/or 6' sialyllactose, etc.). In an embodiment, the one or more antimicrobial or antiviral compounds include lactoferrin, lysozyme, neuraminidase inhibitor, IgA, IgG, IgM, zinc peroxide ($ZnO_2$), copper, and silver. In an embodiment, the respiratory infection is selected from the group consisting of a rhinovirus infection, an influenza virus infection, a fungal infection, and a bacterial infection. In an embodiment, one or more ingredients are selected from the group consisting of a marshmallow extract, a calendula extract, a citrus peel extract, a honey extracts, a rosemary extracts, a myrhh extract, a *Helichrysum* extract, a arrowroot extract, a neem oil, an argan oil, a vitamin C, a vitamin E, a grapefruit seed extract, and combinations thereof.

In one aspect, the invention provides for a method of prophylaxis or treatment of respiratory infection in subjects suffering from or at risk of suffering from respiratory infection comprising: determining a subject is suffering from or at risk of suffering from a respiratory infection; and administering a composition according to the invention comprising one or more antimicrobial or antiviral compounds and a base mixture comprising one or more ingredients selected from the group consisting of a carrier, an emollient, an occlusive, a humectant, an emulsifier, and an essential oil. In an embodiment, the one or more antimicrobial or antiviral compounds comprise soluble ICAM-1. In an embodiment, the one or more antimicrobial or antiviral compounds comprise sialic acid or a derivative thereof (e.g., sialyllactose, etc.). In one embodiment, the one or more antimicrobial or antiviral compounds comprise lactoferrin (e.g., apolactoferrin, etc.). In one embodiment, the one or more antimicrobial or antiviral compounds comprise lysozyme. In one embodiment, the one or more antimicrobial or antiviral compounds comprise a neuraminidase inhibitor. In one embodiment, the one or more antimicrobial or antiviral compounds comprise IgA, IgG, and/or IgM. In one embodiment, the one or more antimicrobial or antiviral compounds comprise zinc peroxide ($ZnO_2$), copper, and/or silver. The compositions may be administered by any suitable route, including orally, topically, nasally, and combinations thereof. In an embodiment, the composition is administered to nasal membranes. In an embodiment, the composition is administered using a device selected from the group consisting of an atomizer, an inhaler, a nebulizer, a spray bottle, and a spray pump. The composition may include a propellant or may be free of propellants.

These and other aspects of the invention will be better understood by reference to the following Detailed Description and appended claims.

BRIEF DESCRIPTION OF THE FIGURES

FIG. 13 illustrates the effect of Rhinovirus A16 infection on mucociliary clearance of epithelial cells with HRV treatments. Mucociliary clearance was monitored 48 (D2) hours post-inoculation on MucilAir™ 3D media.

13 different doses shown in Table 5 (IAV4-1, IAV4-2, and IAV4-3) and Influenza A H1N1 infection at 24 (D1) and 48 (D2) hours post-inoculation on MucilAir™ 3D media.

Figure 43:
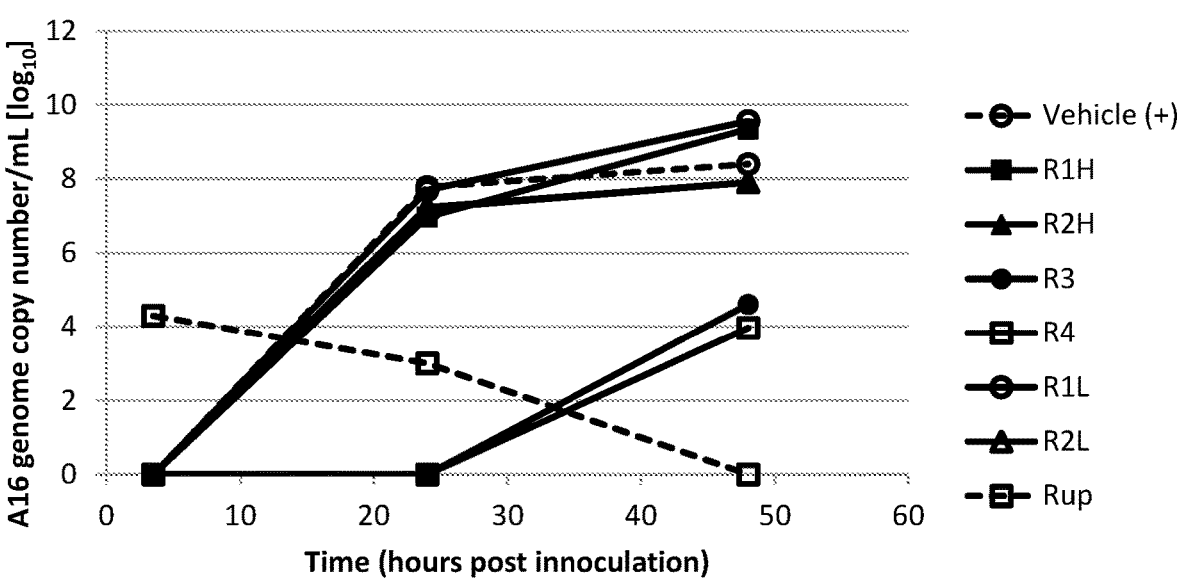

FIG. 43 illustrates the genome copy number of Rhinovirus A16 infection with apolactoferrin treatment (R1H and R1L), lysozyme treatment (R2H and R2L), and soluble ICAM-1 (R3 and R4). Viral load was measured at 3.5, 24, and 48 hours post-inoculation on MucilAir™ 3D media.

Figure 44:
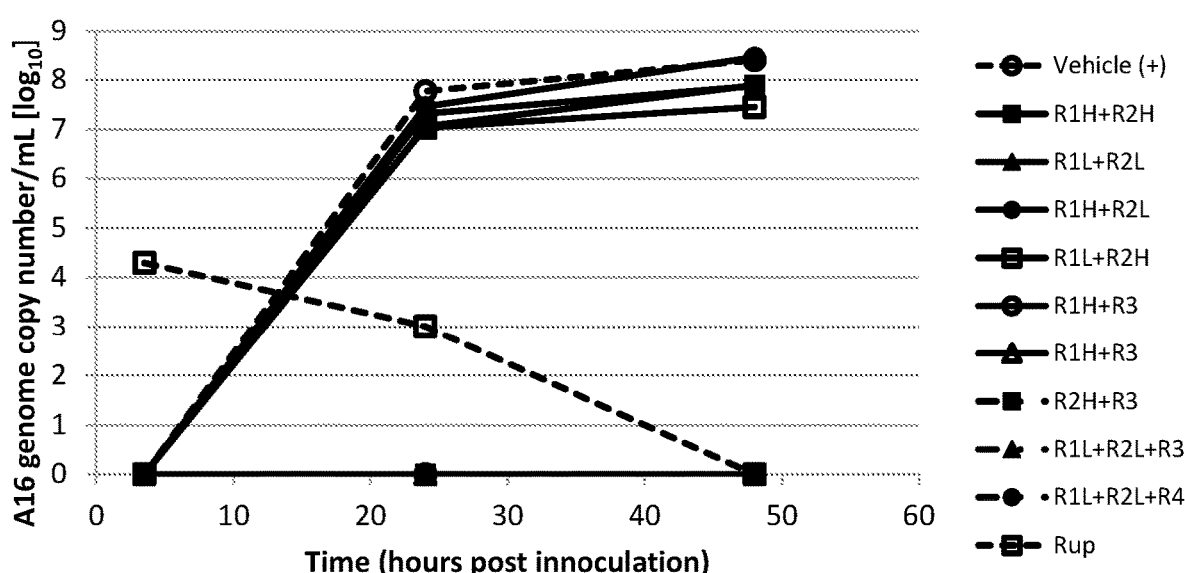

FIG. 44 illustrates the genome copy number of Rhinovirus A16 infection with formulations comprising combinations of the actives shown in FIG. 43. Viral load was measured at 3.5, 24, and 48 hours post-inoculation on MucilAir™ 3D media.

Figure 45:
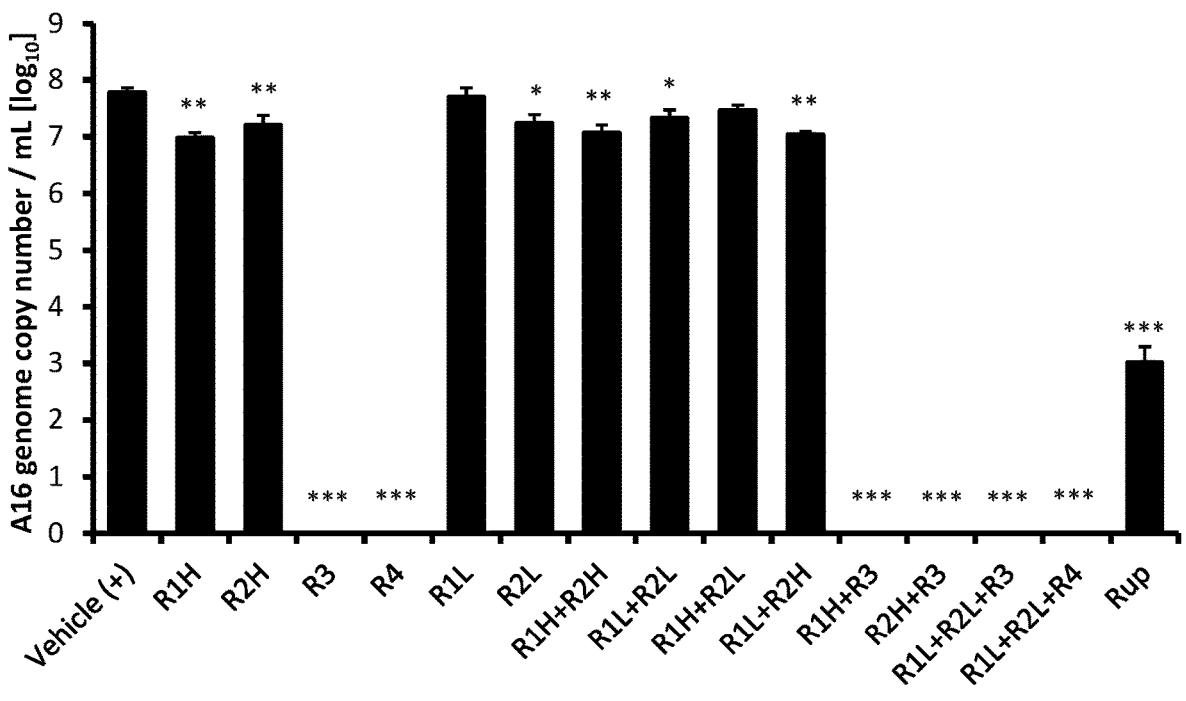

FIG. 45 shows the genome copy number ($Log_{10}$) of Rhinovirus A16 infection with formulations comprising combinations of the actives as detailed in Table 7 at 24 hours pi ("D1"). Statistical significance is measured with respect to control (Vehicle(+)): *:$p<0.05$; :$p<0.01$; *:$p<0.001$.

Figure 46:
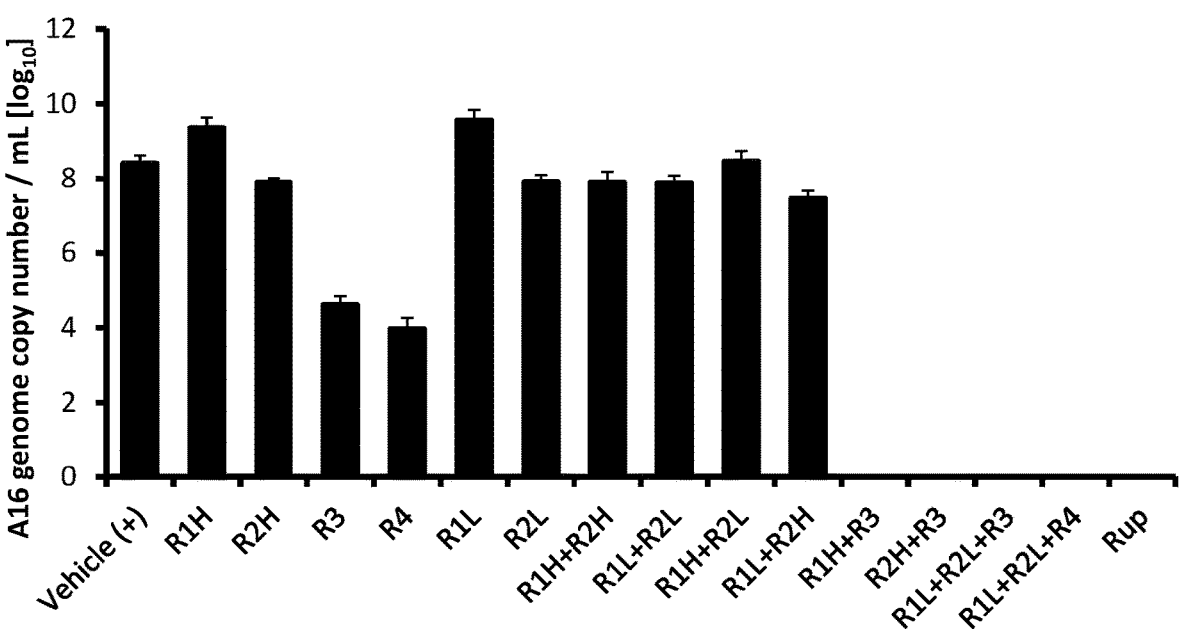

FIG. 46 shows the genome copy number ($Log_{10}$) of Rhinovirus A16 infection with formulations comprising combinations of the actives as detailed in Table 7 at 48 hours pi ("D1"). Statistical significance is measured with respect to control (Vehicle(+)): *:$p<0.05$; :$p<0.01$; *:$p<0.001$.

Figure 47A:
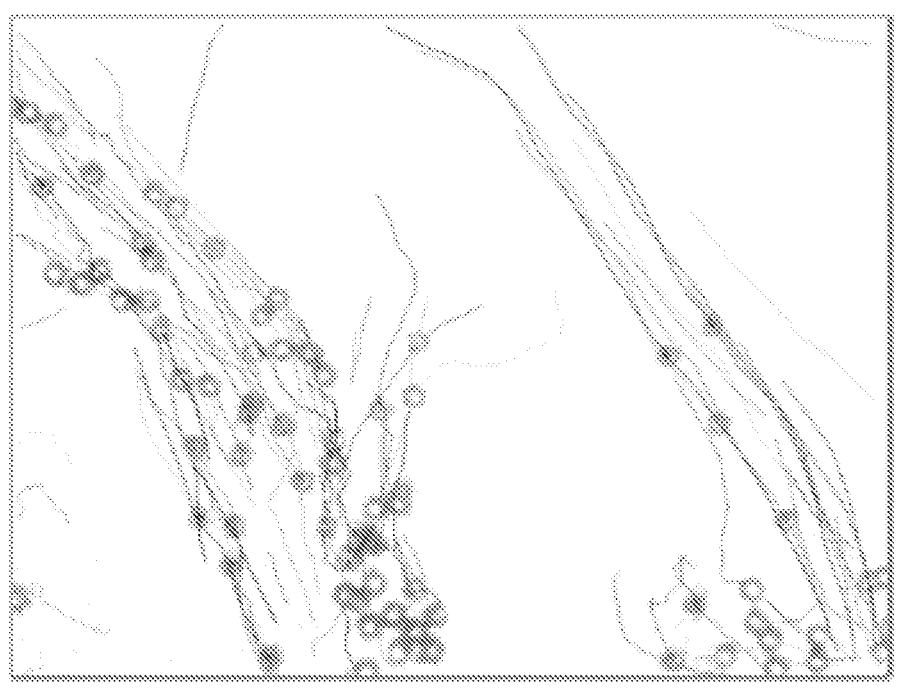
Figure 47B:
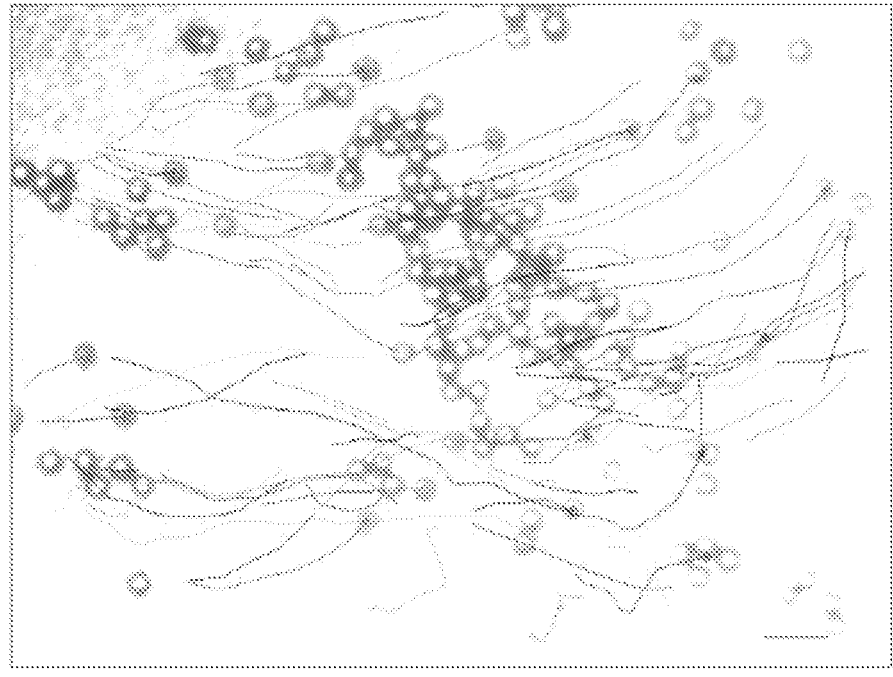

FIG. 47A shows the tracking analysis of beads on the medium for Vehicle (−) used to determine the effect of Rhinovirus A16 infection on mucociliary clearance at 48 hours pi ("D2"). FIG. 47B shows the tracking analysis for the apolactoferrin, lysozyme, and soluble ICAM-1 formulation (R1L+R2L+R4) at D2. The scale bar represents 100 µm, the circles represent individual beads, and the lines represent the trajectory of each measured bead.

Figure 48:
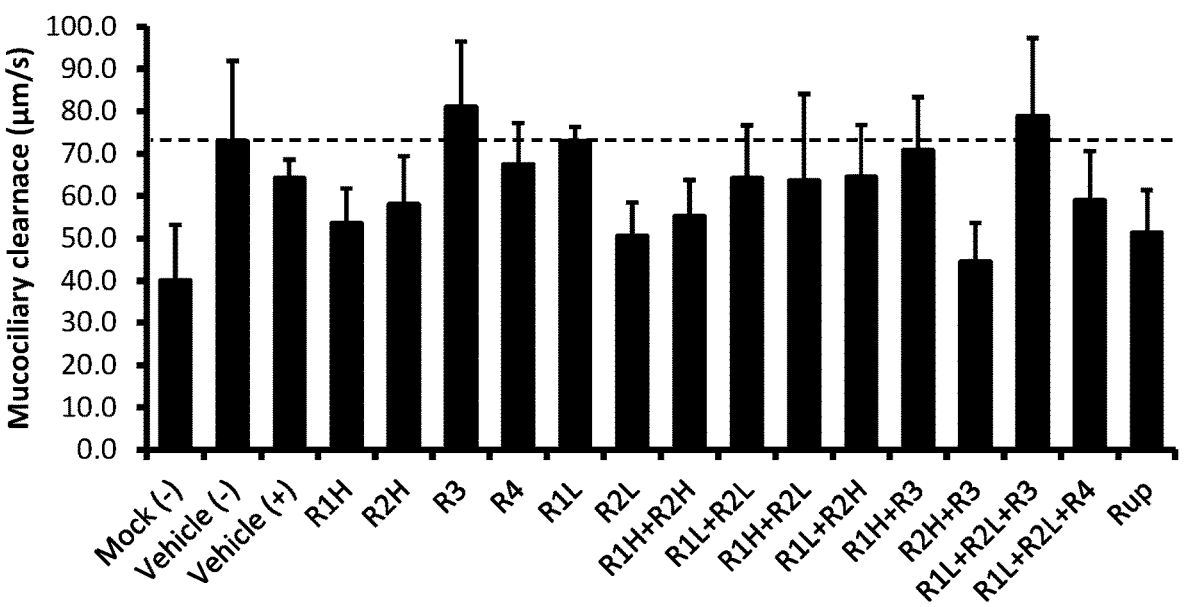

FIG. 48 illustrates the results of the MCC measurements for each specified formulation at D2. The dotted line represents infected Vehicle value for comparison.

Figure 49:
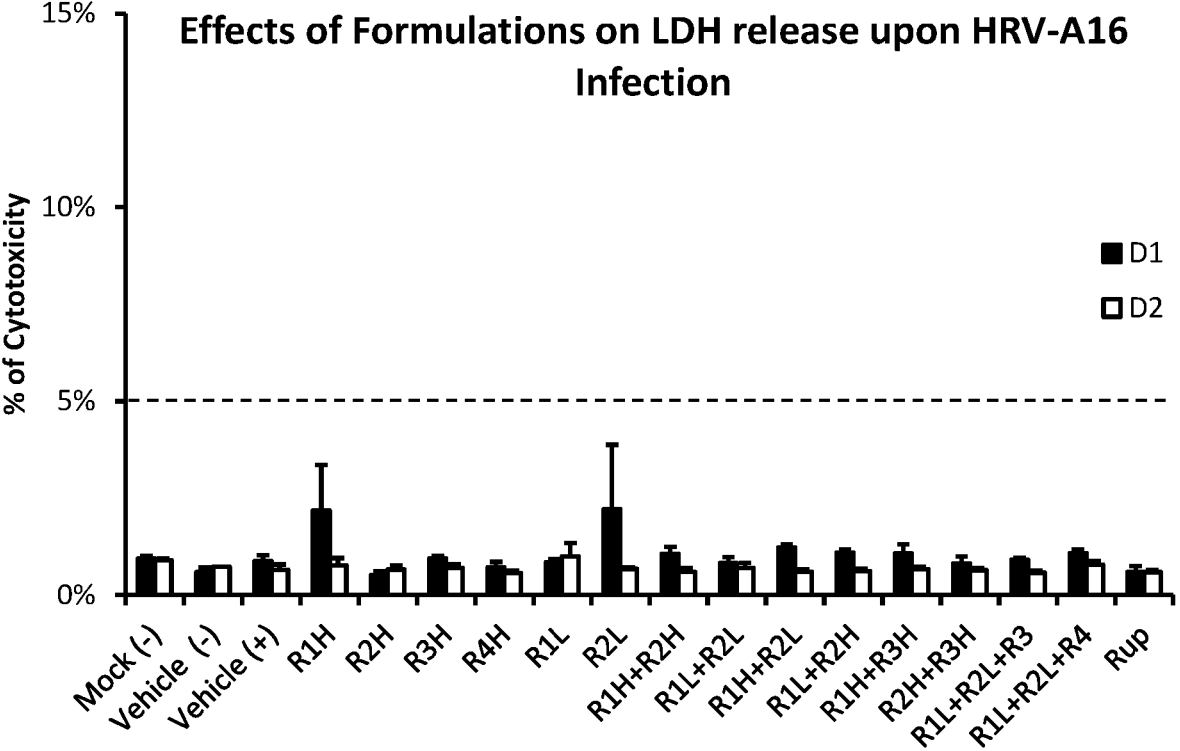

FIG. 49 illustrates the LDH release for innoculated medium with each specified formulation at D1 and D2. The dotted line represents the cytotoxic threshold.

Figure 50:
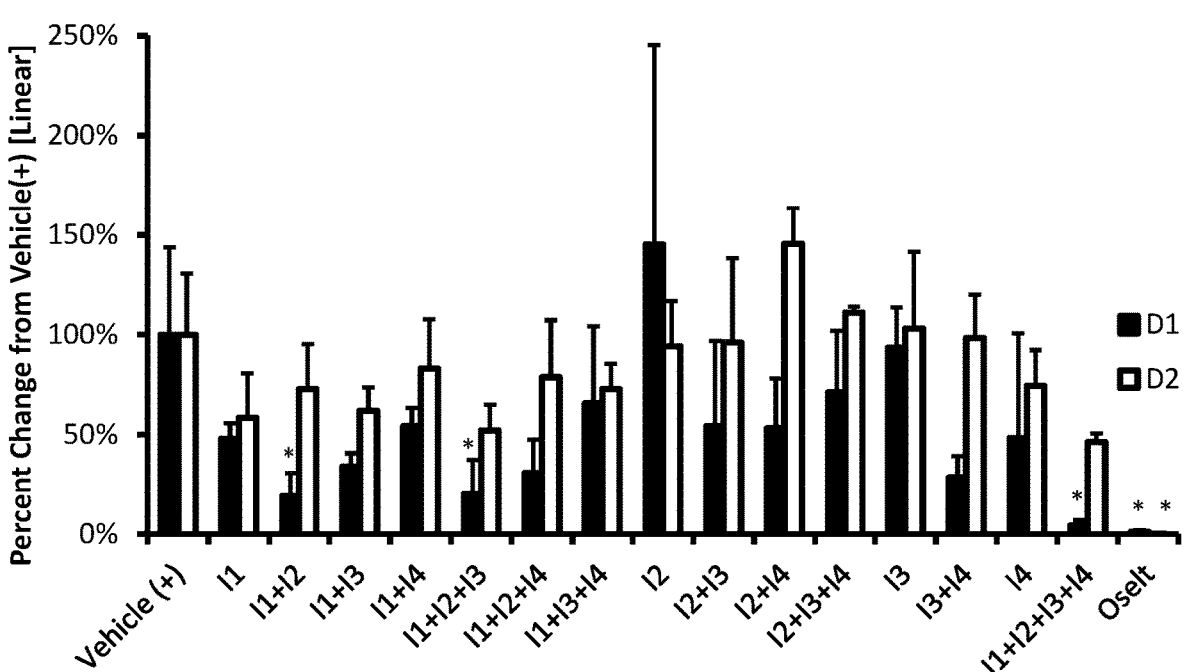

FIG. 50 illustrates the genome copy number (linear) of H1N1 infection as a percentage change from the genome copy number of Vehicle(+) at D1 and D2. Measurements were performed on apical washes of the media at D1 and D2. The formulations comprising combinations of the actives as detailed in Table 8 were applied to the inoculated media. Statistical significance is measured with respect to control (Vehicle(+)) on the specified day: *:$p<0.05$; :$p<0.01$; *:$p<0.001$.

Figure 51:
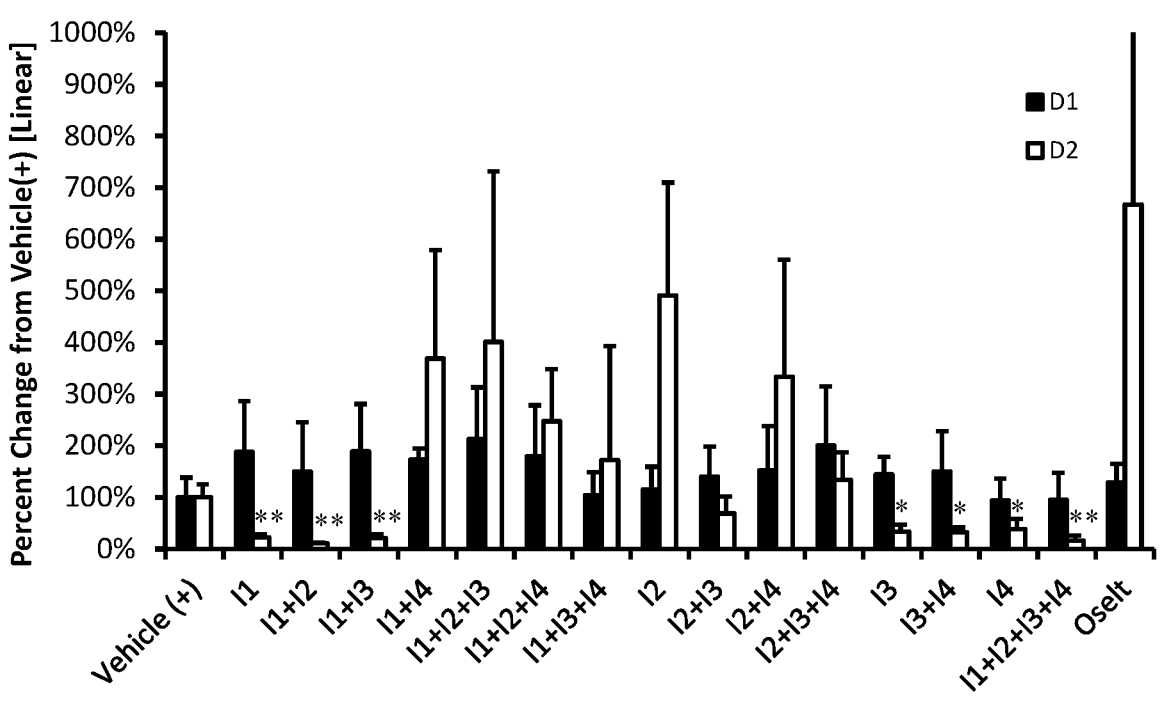

FIG. 51 illustrates the genome copy number (linear) of H1N1 infection as a percentage change from the genome copy number of Vehicle(+) at D1 and D2. Measurements were performed collected basal media at D1 and D2. The formulations comprising combinations of the actives as detailed in Table 8 were applied to the inoculated media. Statistical significance is measured with respect to control (Vehicle(+)) on the specified day: *:$p<0.05$; :$p<0.01$; *:$p<0.001$.

Figure 52:
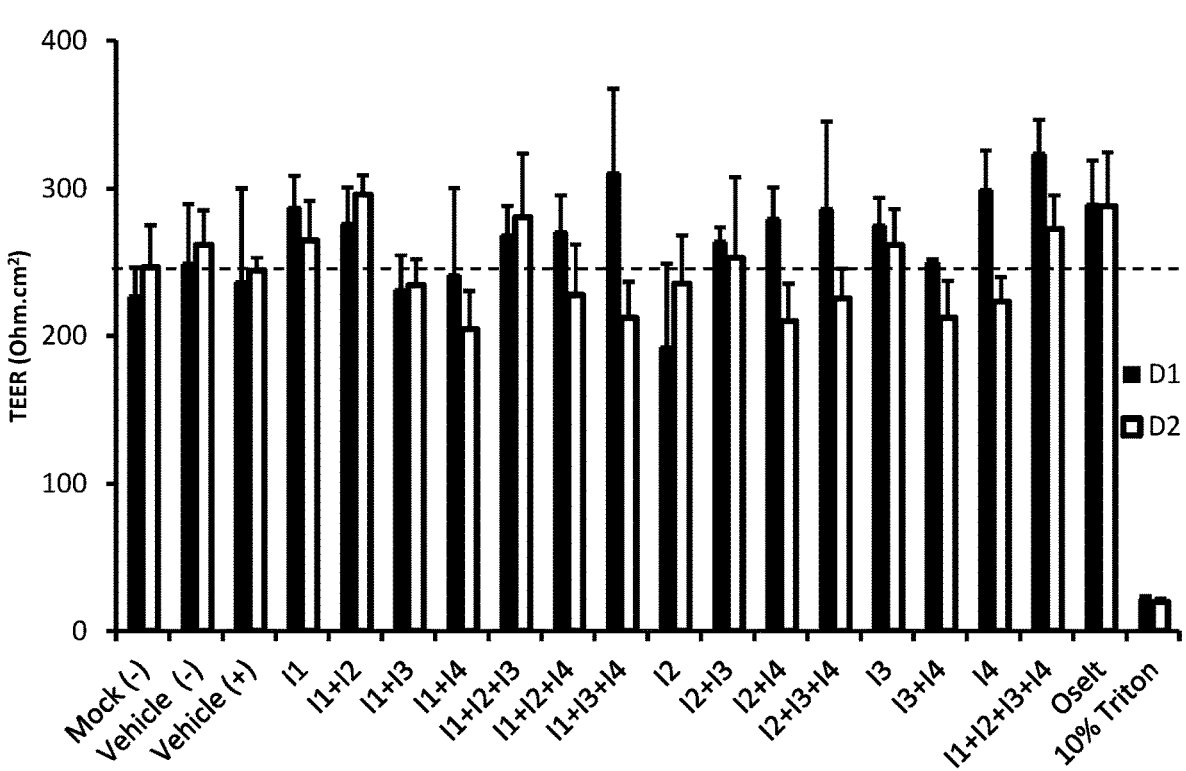

FIG. 52 illustrates the effect of Influenza A H1N1 infection on tissue integrity with various combinations of apolactoferrin, lysozyme, sialyllactoses, and quercetin at the doses shown in Table 8. TEER was monitored 24 (D1) and 48 (D2) hours post-inoculation on MucilAir™ 3D media. The dotted line represents Vehicle(+) for comparison.

Figure 53:
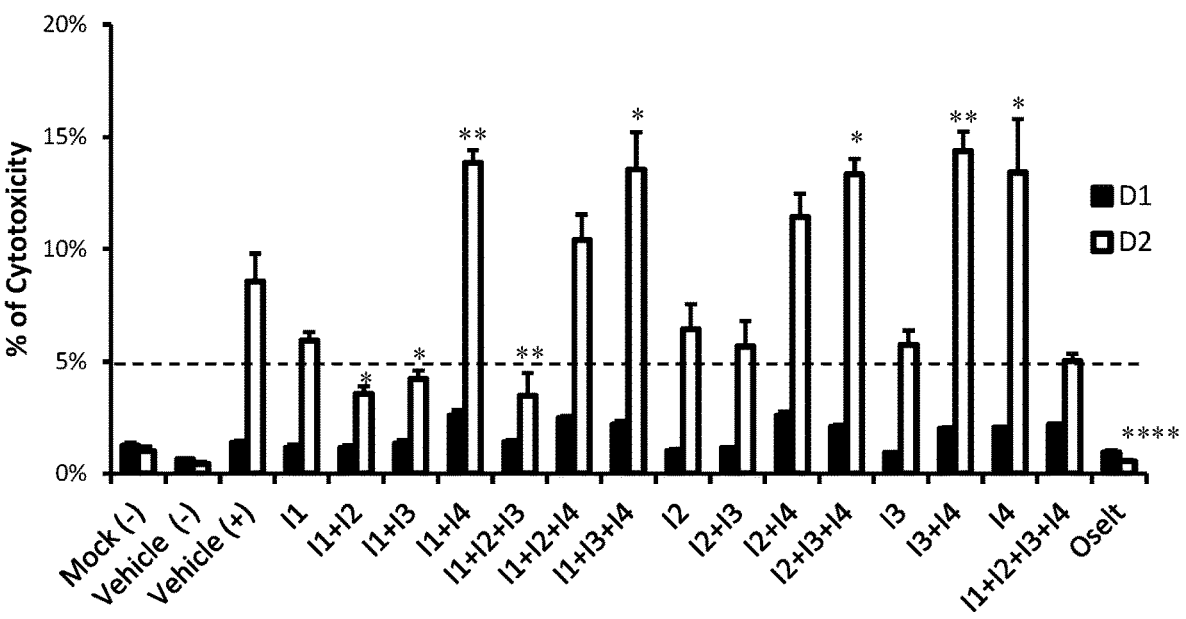

FIG. 53 illustrates the effect of Influenza A H1N1 infection on LDH release from epithelial cells with various combinations of apolactoferrin, lysozyme, sialyllactoses, and quercetin as shown in Table 8. Cytotoxicity was monitored 24 (D1) and 48 (D2) hours post-inoculation on MucilAir™ 3D media.

14

DETAILED DESCRIPTION OF THE DISCLOSURE

The present disclosure may be understood more readily by reference to the following detailed description and the Examples included therein. Before the present methods and techniques are disclosed and described, it is to be understood by one of skill in the art that this disclosure is not to be limited to the specific analytical or synthetic methods described herein. It is also to be understood that the terminology used herein is for the purpose of describing particular embodiments only and is not intended to be limiting. Unless defined otherwise, all technical and scientific terms used herein have the meaning commonly understood by one of ordinary skill in the art to which this disclosure belongs.

By "agent" or "therapeutic agent" is meant any small molecule chemical compound, antibody, nucleic acid molecule, or polypeptide or fragments thereof. By "therapeutic agent" is meant any of the compositions dedicated to preventing or treating respiratory infections described herein.

By "ameliorate" is meant decrease, suppress, attenuate, diminish, arrest, or stabilize the development or progression of a respiratory disease or a symptom thereof.

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

As used herein "an interfering RNA" refers to any double stranded or single stranded RNA sequence, capable—either directly or indirectly (i.e., upon conversion)—of inhibiting or down regulating gene expression by mediating RNA interference. Interfering RNA includes, but is not limited to, small interfering RNA ("siRNA") and small hairpin RNA ("shRNA"). "RNA interference" refers to the selective degradation of a sequence-compatible messenger RNA transcript.

As used herein "an shRNA" (small hairpin RNA) refers to an RNA molecule comprising an antisense region, a loop portion and a sense region, wherein the sense region has complementary nucleotides that base pair with the antisense region to form a duplex stem. Following post-transcriptional processing, the small hairpin RNA is converted into a small interfering RNA by a cleavage event mediated by the enzyme Dicer, which is a member of the RNase III family.

As used herein "an RNAi" (RNA interference) refers to a post-transcriptional silencing mechanism initiated by small double-stranded RNA molecules that suppress expression of genes with sequence homology.

As used herein, "changed as compared to a control" sample or subject is understood as having a level of the analytic or diagnostic or therapeutic indicator to be detected at a level that is statistically different than a sample from a normal, untreated, or control sample or subject. Control samples include, for example, cells in culture, one or more laboratory test animals, or one or more human subjects. Methods to select and test control samples are within the ability of those skilled in the art. An analytic substance can be a naturally occurring substance that is characteristically expressed or produced by the cell or organism (e.g., antibodies, pathogenic peptides or particles, and the like) or a substance produced by a reporter construct (e.g., β-galactosidase or luciferase, etc.). Depending on the detection method used, the amount and measurement of the change may vary. Determination of statistical significance is within the ability of those skilled in the art.

As used herein, the term "co-administering," or "co-administration," and the like refers to the act of administering two or more agents (e.g., an antimicrobial agent and an anti-viral agent, etc.), compounds, therapies, or the like, at or about the same time. The order or sequence of administering the different agents of the disclosure, e.g., antibiotics, anti-virals, antifungals, or immunotherapeutic agents, may vary and is not confined to any particular sequence. Co-administering may also refer to the situation where two or more agents are administered to different regions of the body or via different delivery schemes, e.g., where a first agent is administered intranasally and a second agent is administered systemically, or vice versa. Co-administering may also refer to two or more agents administered via the same delivery scheme, e.g., where a first agent is administered intranasally and a second agent is administered intranasally.

As used herein, the terms "comprises," "comprising," "containing" and "having" and the like are open-ended as defined by U.S. Patent law and can mean "includes," "including," and the like. The terms "consisting essentially of" or "consists essentially" likewise have the meaning ascribed to them in U.S. Patent law and are open-ended, allowing for the presence of more than that which is recited so long as basic or novel characteristics of that which is recited are not changed by the presence of more than that which is recited, but excludes prior art embodiments.

"Contacting a cell" is understood herein as providing an agent to a cell (e.g. a nasal membrane cell, etc.), such that the agent may interact with the cell (e.g., nasal membrane cell to be treated, etc.) and/or taken up by the cell, and have an effect on the cell. The agent (e.g., an antimicrobial or antiviral agent, etc.) may be delivered to the cell directly (e.g., by addition of the agent to a gel or aerosol formulation for nasal delivery, etc.). One of ordinary skill in the art will readily understand that administration of a therapeutic agent to a subject involves contacting the therapeutic agent with a cell or tissue of the subject.

As used herein, the term "coupled," as in reference to two or more agents being "coupled" together, refers to a covalent or otherwise stable association between the two or more agents. For example, a therapeutic agent may be coupled with an antimicrobial agent via a covalent bond, a covalently tethered linker moiety, or non-covalently through ionic interactions or hydrogen bonding. One or more agents that are coupled together retain substantially their same independent functions and characteristics. For example, the therapeutic agent when coupled to another agent may retain its same activity as if it were independent.

By "cycle" or "drug cycle" is meant the administration of repetitive dosing for a defined period of time, which may range from minutes to hours to days to weeks to months or even years.

By "cytokine" is meant a hormone that acts locally and that modulates an individual's to immune response.

As used herein, "detecting," "detection" and the like are understood to include an assay performed to determine one or more characteristics of a sample, e.g. identifying the presence, absence or amount of the analyte to be detected. For example, detection may include identification of a specific analyte in a sample or an activity of an agent in a sample. Detection may include the determination of the presence of nucleic acid or protein (e.g., antibody, cytokine, and the like) by PCR, immunoassay (e.g., ELISA, ELLA, etc.), microscopy, pathogen challenge, and the like. The amount of analyte or activity detected in the sample may be none or below the level of detection of the assay or method.

By "disease" is meant any condition or disorder that damages or interferes with the normal function of a cell, tissue, or organ. An exemplary disease is a respiratory infection.

The terms "effective amount," "therapeutically effective amount" or "pharmaceutically effective amount" as used herein, refer to an amount of an agent or compound that is sufficient to prevent or treat a disorder (e.g., a respiratory infection, a viral infection, etc.). In some embodiments, the result is a reduction in and/or alleviation of the signs, symptoms, or causes of a disorder, or any other desired alteration of a biological system. For example, an "effective amount" for therapeutic may be the amount of the composition comprising a compound as disclosed herein required to provide a clinically significant decrease in a disease/disorder (e.g. a respiratory infection, etc.). An "effective amount" or therapeutically effective amount of an agent or combination of agents of the disclosure may also be that amount or dose that is effective to substantially shrink or eliminate an infection, or prevent its occurrence. An appropriate "effective" amount in any individual case is determined using any suitable technique, (e.g., a dose escalation study, etc.) and will depend on the judgment of the practitioner. However, suitable dosage ranges are readily determinable by to one skilled in the art.

More than one dose may be required to provide an effective dose. It is understood that an effective dose in one population may or may not be sufficient in all populations. Thus, in connection with the administration of a therapeutic agent, the therapeutic agent may be "effective against" a disease or condition when administration in a clinically appropriate manner results in a beneficial effect for at least a statistically significant fraction of subjects, such as a prevention of disease onset, improvement of symptoms, a cure, a reduction in disease signs or symptoms, extension of life, improvement in quality of life, or other effect generally recognized as positive by medical doctors familiar with treating the particular type of disease or condition.

By "enhances" is meant a positive alteration of at least 10%, 25%, 50%, 75%, 100%, or any number there between.

As used herein, an "immunoassay" is a detection method based on the specific binding of at least one antibody to an antigen, e.g., ELISA, ELLA, RIA, western blot, and the like.

As used herein "immunogen," "immunogenic," and the like refer to substances that can promote an immune response, e.g., an antibody based or cell mediated immune response, in at least one organism.

By "immunogenic composition" is meant a composition comprising a molecule capable of inducing or modulating an immune response in a subject. Such an immune response may be a prophylactic or therapeutic immune response.

As used herein, the term "immunotherapeutic agent" refers to any agent, compound, or biologic that is capable of modulating the host's immune system. For example, an immunotherapeutic agent is capable of causing a stimulation of the immune system against a respiratory infection.

As used herein "inducing immunity" is meant to refer to any immune response generated against an antigen. In embodiments, immunity is mediated by antibodies against an infectious agent, which is exhibited by a vertebrate (e.g., a human, etc.), that prevents or ameliorates an infection or reduces at least one symptom thereof. The immunogenic compositions of the disclosure can stimulate the production of antibodies that, for example, neutralize airborne pathogens/infectious agents, block infectious agents from entering cells, block replication of infectious agents, and/or protect host cells from infection and destruction. The term can also refer to an immune response that is mediated by T-lymphocytes and/or other white blood cells against an infectious agent, exhibited by a vertebrate (e.g., a human, etc.), that prevents or ameliorates an infection or reduces at least one symptom thereof.

The term "isolated", as used herein, refers to any composition, molecule, or mixture that has undergone a laboratory purification procedure including, but not limited to, extraction, centrifugation, chromatographic separation (i.e., for example, thin layer chromatography or high performance liquid chromatography). Usually such a purification procedure provides an isolated composition, molecule, or mixture based upon physical, chemical, or electrical potential properties. Depending upon the choice of procedure an isolated composition, molecule, or mixture may contain other compositions, compounds or mixtures having similar chemical properties. For example, an isolated composition, molecule, or mixture may contain between 1-20%, 1-10%, or 1-5% of compositions or mixtures having similar chemical properties.

As used herein, the term "local" or "locally," as in local administration or coadministration of one or more therapeutics, refers to the delivery of a therapeutic agent to a bodily site (e.g. a nasal membrane, etc.) that is proximate or nearby the site of an infection, adjacent or immediately nearby the site of the infection, at the perimeter of or in contact with the infection, or within or inside the infected tissue. Local administration generally excludes systemic administration routes.

As used herein, "nucleic acid" as in a nucleic acid for delivery to a cell is understood by its usual meaning in the art as a polynucleotide or oligonucleotide that refers to a string of at least two base-sugar-phosphate combinations. Nucleotides are the monomeric units of nucleic acid polymers. The term includes deoxyribonucleic acid (DNA) and ribonucleic acid (RNA) in the form of an oligonucleotide messenger RNA, anti-sense, plasmid DNA, parts of a plasmid DNA, genetic material derived from a virus, and the like. Polynucleotides include nucleic acids of at least two monomers. Anti-sense polynucleotides are nucleic acids that interfere with the function of DNA or RNA. An siRNA or an shRNA is a double stranded RNA that inhibits or disrupts activity or translation, for example by promoting degradation of modifying splicing or processing of the cellular nucleic acid, e.g., mRNA, microRNA, and the like, to which it is targeted. As used herein, siRNA and shRNA include any double stranded RNA molecule that can modulate the stability, translation, or splicing of an RNA to which at least one strand of the double stranded nucleic acid hybridizes. RNAs are well known in the art, see e.g., patent publications WO/2002/044321, WO/2003/099298, US 20050277610, US 20050244858; and U.S. Pat. Nos. 7,297,786, 7,560,438 and 7,056,704, all of which are incorporated herein by reference. Nucleic acid as used herein is understood to include non-natural nucleotides (not occurring in nature), for example: a derivative of natural nucleotides such as phosphothionates or peptide nucleic acids (such as those described in the patents and applications cited immediately above). A nucleic acid can be delivered to a cell in order to produce a cellular change that is therapeutic or prophylactic. The nucleic acid may express a protein or polypeptide, e.g., a protein that is missing or non-functional in the cell or subject. The nucleic acid may be single or double stranded, may be sense or anti-sense, and can be delivered to a cell as naked DNA, in combination with agents to promote nucleic acid uptake to into a cell (e.g., transfection reagents, etc.), in the context of a viral vector, and the like. The nucleic acid can be targeted to a nucleic acid that is endogenous to the cell (mRNA or microRNA), or a heterologous nucleic acid (e.g., nucleic acid from a pathogen, such as a viral gene, etc.). Delivery of a nucleic acid means to transfer a nucleic acid from outside a subject to within the outer cell membrane of a cell in the subject.

"Obtaining" is understood herein as manufacturing, purchasing, synthesizing, isolating, purifying, or otherwise coming into possession of.

The term "pharmaceutically acceptable" as used herein, refers to a material, (e.g., a carrier or diluent, etc.), which does not abrogate the biological activity or properties of the compounds described herein, and is relatively nontoxic (i.e., the material is administered to an individual without causing undesirable biological effects or interacting in a deleterious manner with any of the components of the composition in which it is contained).

The phrase "pharmaceutically acceptable carrier, excipient, or diluent" is art recognized and includes a pharmaceutically acceptable material, composition or vehicle, suitable for administering compounds of the present disclosure to mammals. As used herein, the term "pharmaceutically acceptable" means being approved by a regulatory agency of the Federal or a state government or listed in the U.S. Pharmacopia, European Pharmacopia or other generally recognized pharmacopia for use in mammals, e.g., humans.

As used herein, the term "pharmaceutically effective regimen" refers to a systematic plan for the administration of one or more therapeutic agents, which includes aspects such as type of therapeutic agent, therapeutic agent concentrations, and any changes therein made during the course of the drug administration, which when administered is effective in treating and/or preventing an infection. Such considerations depend on the judgment of the practitioner and are readily determinable by one skilled in the art.

A "polypeptide" or "peptide" as used herein is understood as two or more independently selected natural or non-natural amino acids joined by a covalent bond (e.g., a peptide bond, etc.). A peptide can include 2, 3, 4, 5, 6, 7, 8, 9, 10, 11, 12, 13, 14, 15, 16, 17, 18, 19, 20, or more natural or non-natural amino acids joined by peptide bonds. Polypeptides as described herein include full length proteins (e.g., fully processed proteins, etc.) as well as shorter amino acids sequences (e.g., fragments of naturally occurring proteins or synthetic polypeptide fragments, etc.).

Ranges provided herein are understood to be shorthand for all of the values within the range including the limits of the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

By "reduces" is meant a negative alteration of at least 10%, 25%, 50%, 75%, 100%, or any number there between.

By "reference" is meant a standard or control condition.

As used herein, the term "regimen" refers to the various parameters that characterize how a drug or agent is administered, including, the dosage level, timing, and iterations, as well as the ratio of different drugs or agents to one another. The term "pharmaceutically effective regimen" refers to a particular regimen that provides a desired therapeutic result or effect. The term "iterations" refer to the general concept of repeating sets of administering one or more agents. For example, a combination of drug X and drug Y may be given (co-administered at or about at the same time and in any order) to a patient on a first day at dose Z. Drugs X and Y may then be administered (co-administered at or about at the same time and in any order) again at dose Z, or another dose, on a second day. The timing between the first and second days can be 1 day or anywhere up to several days, or a week, or several weeks, or months. The iterative administrations may also occur on the same day, separated by a specified number of minutes (e.g., 10 minutes, 20 minutes, 30 minutes or more) or hours (e.g., 1 hour, 2 hours, 4 hours, 6 hours, 12 hours, etc.). An effective dosing regimen may be determinable by those of ordinary skill in the art, e.g., prescribing physician, using standard practices.

A "sample" as used herein refers to a biological material that is isolated from its environment (e.g., blood or tissue from an animal, cells, or conditioned media from tissue culture). In embodiments, the sample is suspected of containing, or known to contain an analyte, such as an infectious agent or a protein of interest (e.g., antibody, cytokine, and the like). A sample can also be a partially purified fraction of a tissue or bodily fluid. A reference sample can be a "normal" sample, from a donor not having the disease or condition fluid, or from a normal tissue in a subject having the disease or condition, or an untreated to subject (e.g., a subject not treated with the vaccine, etc.). A reference sample can also be taken at a "zero time point" prior to contacting the cell or subject with the agent or therapeutic intervention to be tested.

As used herein, the term "selectively" means tending to occur at a higher frequency in one population than in another population.

By "specifically binds" is meant recognition and binding to a target (e.g., polypeptide, cell, and the like), while not substantially recognizing and/or binding other molecules in a sample, for example, a biological sample.

The term "subject", as used herein, refers to any organism that is capable of experiencing a respiratory infection. Such organisms include, but are not limited to, human, dog, cat, horse, cow, sheep, goat, mouse, rat, guinea pig, monkey, primate, non-human primate, avian, reptiles etc.

A subject "suffering from or suspected of suffering from" a specific disease, condition, or syndrome (e.g., a respiratory infection, etc.) has a sufficient number of risk factors or presents with a sufficient number or combination of signs or symptoms of the disease, condition, or syndrome such that a competent individual would diagnose or suspect that the subject was suffering from the disease, condition, or syndrome. Methods for identification of subjects suffering from or suspected of suffering from respiratory infection is within the ability of those in the art. Subjects suffering from, and suspected of suffering from, a specific disease, condition, or syndrome are not necessarily two distinct groups. The phrase "individual in need thereof" or "patient in need thereof" or "subject in need thereof" denotes an individual having a disease or condition (e.g., a respiratory infection, etc.). In some implementations, the individual in need thereof is a patient that has influenza virus or rhinovirus.

The term "prevent" or "prophylaxis" as used herein, includes preventing, diminishing the extent of, or delaying the onset of or progression of a disease or physiological manifestation of disease. "Prophylaxis" or "prevent" may refer to preventing, diminishing the extent of, or retarding the rate of infection (e.g., viral infection, etc.). The term "treat" includes reducing, diminishing, eliminating, ameliorating, forestalling, slowing the progression of, and/or delaying the onset of a given disease or physiological manifestation thereof. Non-limiting examples include humans, other mammals, bovines, rats, mice, dogs, monkeys, goat, sheep, cows, deer, and other non-mammalian animals including birds. In some embodiments, a patient is human.

As used herein, "susceptible to" or "prone to" or "predisposed to" a specific disease or condition and the like refers to an individual who based on genetic, environmental, health, and/or other risk factors is more likely to develop a disease or condition than the general population. An increase in likelihood of developing a disease may be an increase of about 10%, 20%, 50%, 100%, 150%, 200%, or more.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease.

The term "glycolipids", as used herein, refers to any molecule with at least one carbohydrate chain linked to a ceramide, a fatty acid chain, or any other lipid. Alternatively, a glycolipid maybe referred to as a glycosphingolipid.

As used herein and in the appended claims, the singular forms "a," "and," and "the" include plural reference unless the context clearly dictates otherwise. Thus, for example, reference to "a gene" is a reference to one or more genes and includes equivalents thereof known to those skilled in the art, and so forth.

Unless specifically stated or obvious from context, as used herein, the term "or" is understood to be inclusive.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

Unless otherwise indicated, all references to concentrations include the indicated amounts on a weight by weight, weight by volume or volume by volume basis. Any reference to a percent concentration will be understood to refer to wt/wt, wt/vol, or wt/vol. While certain embodiments may be described by concentrations as wt/wt or wt/vol, it should be understood that such compositions disclose the same % on a wt/wt or wt/vol basis. The density of any forms of the invention may be between 0.8 g/mL and 1.2 g/mL, for example between 0.9 g/mL and 1.1 g/mL or between 0.95 g/mL and 1.05 g/mL.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Other definitions appear in context throughout this disclosure.

Any therapeutic agents, compositions, or methods provided herein can be combined with one or more of any of the other therapeutic agents, compositions, and methods provided herein. It will be understood that derivatives such as esters, and prodrugs that retain the functionality of the base compound are contemplated.

The present disclosure provides compositions and methods for preventing and treating respiratory infections. The present disclosure features methods and compositions for enhancing the filtering capabilities of the nasal membranes and protecting against airborne pathogens by enhancing the health of the nasal membranes and filtering capabilities of nasal mucous. In particular, the disclosure features antimicrobial, antiviral, and antifungal compositions that prevent and treat respiratory infections caused by bacteria, viruses, and fungi, including influenza viruses and rhinoviruses (e.g. viruses that cause the flu and common cold, respectively). The present disclosure is based, at least in part, on the discovery that compositions including antimicrobial, antiviral, and/or antifungal functionalities may be used to enhance the health and filtering capabilities of nasal membranes and protect against airborne pathogens. In so doing, they must also maintain the physiological health of the membranes such as by maintaining a healthy pH and osmolarity and encouraging the propagation of healthy microflora. In a particular exemplary embodiment, the present disclosure relates to an antimicrobial and anti-fungal filtering composition formulated for topical application to the proximal anterior nares or the inner anterior nasal membrane, where it may also coat nasal hairs and enhance the filtering capabilities of the nose. Advantageously, the present disclosure, as described herein, provides a topically applied filtering composition for nasal and/or oral application that does not adversely affect the chemical properties of the respiratory membranes or mucosa (and enhances its natural filtering capabilities) and that will specifically target and protect against several disease causing microorganisms.

The present disclosure also provides for methods of enhancing the natural filtration properties of the respiratory membranes and reducing the number of microorganisms, allergens, and odorants entering the body through the nose or proliferating along the respiratory membranes. In some embodiments, this method includes application of a topical or inhaled, or ingested solution of antimicrobial, antiviral, anti-fungal, and/or odor-neutralizing composition to the mouth, the throat, the opening of the nostrils, the nasal epithelial inside the nostrils, and/or the nasal hairs. The antimicrobial, antiviral, and anti-fungal solution may be in gel, lotion, lozenge, vapor, or aerosol forms and may have a combination of active ingredients intended to bolster the natural filtration capabilities of the nose in a base medium that allows the active ingredients to be well tolerated, in their active forms, while preventing them from having undesirable effects. The compositions herein may also mimic the chemical properties of natural healthy mucous or saliva such as, for example, pH and osmolarity. The ingredients may be balanced to create a synergistic effect stronger than any of the ingredients alone and may also be balanced to maintain a healthy pH and osmolarity in the respiratory membranes as these parameters have been shown to affect the likelihood of disease transmission and allergic reaction. The active ingredients may include, but are not limited to, recombinant, naturally derived, or purified lactoferrin, lysozyme, ICAM, cationic peptides, glycosylated peptides, sialic acid, quercetin, or other bioflavonoids, in addition to any plant extract having antimicrobial properties (including but not limited to fruit peel extracts and carrageenans), silver, copper, or zinc micro particles, and lauric acid, which have proven antimicrobial properties. Various embodiments may also include one or more of the following ingredients: sodium bicarbonate, activated charcoal, cocoa butter, shea butter, beeswax, plant butters, glycerine, honey, alginates, or plant mucilage, and a preservative such as vitamin C, vitamin E, or rosmarinic acid. Various embodiments may include ingredients that, when mixed with the aforementioned active ingredients, create a formulation that is well-tolerated when applied to the opening of the nostrils, the nasal epithelia inside the nostrils, or the nasal hairs, and that allows the active ingredients to adhere to the areas of application for a sufficient period of time to prevent infection or allergy before reapplication.

Respiratory Function

Respiratory infections are among the most common type of communicable diseases throughout the world today. Almost yearly, new and potentially deadly diseases such as Middle East Respiratory Syndrome (MERS) and Avian and Swine influenzas capture world-wide attention and concern. New and unusual strains of influenza virus are continuously emerging and are capable of creating worldwide epidemics in a matter of months. Moreover, the current state of vaccine and anti-viral technology is not well equipped to deal with these outbreaks in a timely manner. At best, a targeted vaccine to a new viral strain is available in six months to a year, at which point an epidemic could be well underway.

Every day, about 12,000 liters of air is filtered by the average nose. The nasal passages filter 95% of particles greater than 15 μm in diameter out of the air. They are normally trapped by mucous and then ingested. Microorganisms and allergens are normally several orders of magnitude smaller than this threshold and have evolved to evade or overcome natural mucosal defenses in the nose, penetrate the nasal membranes, and/or enter the lower respiratory tract via the mouth or throat. According to the techniques herein, augmenting the respiratory membranes and mucosa with anti-microbial and filtering agents may allow a significant number of respiratory infections and allergies to be prevented in an easy, unobtrusive, and convenient way. Additionally, many of the undesirable particles entering the nose are odorants which can be a nuisance and which can be filtered or neutralized by certain substances such as but not limited to activated charcoal or sodium bicarbonate suspended in a carrier before they are able to bind odorant receptors.

The present disclosure is directed to an antimicrobial, antiviral, anti-fungal, odor-neutralizing topical application that simulates certain chemical properties of nasal mucous, does not impair the health or integrity of the nasal membranes, or adversely affect its beneficial microflora, and also serves as a filter to prevent airborne irritants and pathogens from penetrating the nasal membranes and/or entering the lower respiratory tract. In so doing, the compositions herein prevent infection of the respiratory tract, while also preventing irritation and/or allergic reactions.

In addition, the compositions herein may be isotonic to nasal epithelia and mucous membranes and contain compounds with health promoting properties. Beneficial microflora and certain properties of the nasal membrane such as osmolarity and pH have been shown to affect the likelihood of infection. Several medications and health conditions have been identified that make people more susceptible to respiratory infection. For example, diabetics are likely to have dry nasal membranes and suffer from fungal sinusitis. Oral contraceptives, sleep apnea machines, and allergies are also known to make the nasal membranes drier and more susceptible to infection.

The compositions of the present disclosure may include specific active ingredients with proven antimicrobial properties including but not limited to, ICAM-1, ICAM-1 inhibitors, sialic acid, neuraminidase inhibitors, lysozyme, lactoferrin, citrus oils, extracts, or derivatives, plant mucilage, peptides, glycopeptides, amino acids, antimicrobial oils, antimicrobial plant extracts, or defensins. The composition may include odor-neutralizing compounds such as, but not limited to activated charcoal or sodium bicarbonate. The composition may have adhesive properties and be specifically formulated to keep active ingredients and antimicrobials/antivirals on the surface of the nasal epithelium for an extended period of time. To achieve this, the compositions herein may include substances of low volatility, or occlusive substances such as, for example, polyols, shea butter, or other plant butters, coconut oil, beeswax, and bioadhesive substances such as mucilage, or alginates.

The nasal formulations described herein and their active ingredients are intended to be well tolerated, exert beneficial effect on ciliary function, have good dispensing properties, a high degree of adhesion, and maintain the chemical properties of the mucosa. In some embodiments, ingredients are balanced to create synergistic effects.

According to the techniques herein, one or more of the active ingredients may target undesirable microorganisms and viruses specifically. Many airborne pathogens such as rhinoviruses and influenza gain entry into nasal epithelial cells, nasal mucosa, or cells of the lower respiratory tract through specific cell surface targets. Decades of research have identified ICAM-1 (Intracellular Adhesion Molecule-1) as one such target for most rhinoviruses and another for influenza (Abraham and Colonno 1984). ICAM-1 is an intercellular adhesion molecule expressed on the cell surface of nasal epithelial cells, as well as cells of the lower respiratory tract. The N-terminal domain of ICAM-1 is recognized by receptors on certain rhinovirus capsids. Upon binding ICAM-1, the virus sheds its capsid and is transported into the cell where it initiates infection and an inflammatory response by the host. Influenza viruses exhibit a similar mechanism of infection: in humans, hemagglutinin (HA) on viral surfaces bind sialic acid attached to galactose (e.g. by an alpha 2,6 linkage (6'-sialyllactose) or by an alpha 2,3 linkage (3'-sialyllactose), etc.), on the host cell membrane of erythrocytes and cells of the upper respiratory tract.

Prior art such as, for example, U.S. Pat. Nos. 8,211,448, 8,940,339, and 8,211,448 disclose methods of entrapping airborne particles by using manufactured polymers or compounds. In sharp contrast to these prior art methods, the present disclosure renders airborne particles inert and augments the abilities of the nasal membranes to eliminate disease or allergy causing microorganisms and other undesirable particles. Moreover, embodiments utilizing more than one active ingredient may protect against more than one pathogen or irritant at the same time and in an augmented fashion. This differs from prior art methods that may target only one type of pathogen only weakly or moderately (e.g., U.S. Pat. Nos. 7,132,395; 6,514,936; 6,051,231; 6,649,592; Turner et al. JAMA 281 (19). 1797-1804. (1999)). This is important because the specific identity of a disease or allergy causing microorganism is often unknown at the time of initial exposure to a subject. In some embodiments of the present disclosure, drugs may be delivered to the surface of the nasal membranes without absorption through the membrane and without being bioadhesivly attached thereon (e.g., U.S. Pat. No. 6,391,452; US Publication No. 2001/0053359; U.S. Pat. No. 8,679,484; U.S. Pat. Nos. 645,626, 7,087,245). In some embodiments, the pharmaceutical compositions may not impart a protective layer with broad-based antimicrobial properties as disclosed in US Publication No. 2007/0135377, U.S. Pat. Nos. 7,166,435, 8,658,775, 8,658,775, 7,083,814, 7,807,656, 9,045,855, 6,649,592, and 9,029,351.

Typically, the techniques disclosed herein administer targeted antimicrobials in pharmaceutical compositions which also maintain the specific physiological and chemical properties of the nasal membranes or mucous such as, for example, their pH and osmolarity. In some embodiments, the methods of treating respiratory infection disclosed herein do not comprise non-targeted, indiscriminant antimicrobials to the nasal membranes that may contain alcohol, peroxide, or other harsh ingredients. Typically used in formulations (e.g., U.S. Pat. Nos. 8,999,406; 8,778,415; 7,638,147), these harsh ingredients change the pH or osmolarity of the nasal membranes and negatively impact microflora. In some embodiments, the pharmaceutical composition comprises less than 10% harsh ingredients (e.g., alcohol, peroxide, etc.) by weight of the composition or less than 5% harsh ingredients by weight of the composition or less than 1% harsh ingredients by weight of the composition or less than 0.1% harsh ingredients by weight of the composition or less than 0.01% harsh ingredients by weight of the composition. Typically, application of the pharmaceutical composition to a nasal membrane will alter the pH of the membrane and/or mucous by less than 20% or less than 10% or less than 5% or less than 1% or less than 0.1% of the pH prior to application. In some embodiments, application of the pharmaceutical composition to a nasal membrane will alter the osmolarity of the membrane and/or mucous by less than 20% or less than 10% or less than 5% or less than 1% or less than 0.1%.

Antimicrobial Compositions

The antimicrobial compositions herein may incorporate one or more antimicrobial and antiviral active ingredients within a base mixture comprising one or more of water, polyols, emollients, occlusives, humectants, emulsifiers, preservatives, thickeners and suspending agents, pH adjusters, isotonicity agents, and essential oils that allow it to remain at or near the site of application for at least 30 minutes (e.g. 30-60 minutes, 1-2 hours, 2-4 hours, 4-8 hours, 8-12 hours, 12-24 hours, 1-2 days, 2-7 days, a week or more) before being absorbed, and which have similar pH and osmolarity to mucous, and which do not clog pores. The time it takes for the antimicrobial composition to be absorbed can be determined by the saccharine test or other similar tests. In one embodiment, the active ingredient may be soluble ICAM-1, comprising just the extracellular domain, or another domain of ICAM-1 recombinantly expressed in bacteria. In other embodiments, the active ingredient may be soluble ICAM-1 recombinantly expressed in *Chlamydomonas reinhardtii*. In other embodiments, the active ingredient may be soluble ICAM-1 recombinantly expressed in another species of algae, or another living system.

In another embodiment, the active ingredient is sialic acid (e.g., neuraminic acid linked to a sugar molecule in one of several possible conformations, etc.). The sialic acid may be purified from a natural source or produced by fermentation and recombinant engineering. In another embodiment, the active ingredient may be a neuraminidase inhibitor such as quercetin, which is a bioflavanoid isolated from citrus peels or other natural sources. In another embodiment, the active ingredient is lactoferrin recombinantly expressed in bacteria. In other embodiments, the active ingredient is lactoferrin recombinantly expressed in *Chlamydomonas reinhardtii* or another appropriate expression system, e.g. algae, yeast, or bacteria, or purified from a natural source. In another embodiment, the active ingredient may be lysozyme recombinantly expressed in *Chlamydomonas reinhardtii* or another appropriate expression system, e.g. algae, or purified from a natural source. As disclosed herein, additional antimicrobial active ingredients may be used in the compositions of the disclosure, either alone or in combination.

In another embodiment, the active ingredient is a naturally occurring or genetically engineered antibody such as IgA, IgG, or IgM, or any of their domains in one of several possible conformations. The antibody may be purified from a natural source or produced by recombinant engineering in any appropriate and economically feasible expression system such as *Chlamydomonas reinhardtii* or another algae, a bacteria, a yeast, or a mammalian cell, or it may be purified from a natural source. In another embodiment, the active ingredient may be a neuraminidase inhibitor such as quercetin, which is a bioflavanoid isolated from citrus peels or other natural sources.

Algae or other plants are the preferred expression system because recombinantly engineered algae are far more economical to grow and harvest than mammalian cells or bacteria. Algae are grown for use as nutritional supplements themselves and are also used to bioengineer certain nutritional compounds for commercial production such as omega-3 fatty acids and carotenoids (Gimpel J A, Henriquez V, and Mayfield S P Frontiers in Microbiology 2015). Most metabolic engineering strategies have been geared towards enhancing commercial production of these compounds and also for using algae as biofuels. Advantageously, algae may be optimized to produce a range of different metabolites that have certain characteristics in an efficient manner. The expression of active ingredients may be optimized.

Transgenic algae have been shown to support recombinant protein expression from both the chloroplast and nuclear genomes (Rasal B A et al., Plant Biotechnology J 2010). Originally, only the nuclear genomes were used but the development of techniques required to express recombinant proteins in the chloroplast genome add versatility to the platform and make it possible to either express proteins that cannot be expressed in the nuclear genome or to express the proteins more efficiently. The majority of recombinant proteins produced today are produced mainly in bacteria, yeast (*S. cervisiae*), or mammalian cell culture. Other systems under development for large scale production include the yeast *P. pastoris*, insect cells, and other animals and plants. Any viable plant or animal expression system may be used but first, those which are likely to be the most cost-efficient such as those recombinant expression systems that will not require a high degree of purification will be investigated and sought out. This will make it possible for the embodiment to be sold over the counter without the need for clinical trials. If needed, other recombinant expression systems are used that may require higher degrees of purification.

As depicted in Table 1, the agents of the composition may be present according to the following percentages by weight of the composition:

TABLE 1

| Active Ingredients | % by weight | Example formulation (% by weight) |
| --- | --- | --- |
| sICAM-1 | 0.00000001%-10.0% | 0.000001%-1% |
| Lactoferrin | 0.00000001%-10.0% | 0.000001%-1% |
| Lysozyme | 0.00000001%-10.0% | 0.000001%-1% |

TABLE 1-continued

| Active Ingredients | % by weight | Example formulation (% by weight) |
| --- | --- | --- |
| Sialic acid | 0.00000001%-10.0% | 0.000001%-1% |
| Neuraminidase inhibitor | 0.00000001%-10.0% | 0.000001%-1% |

As indicated in Table 1, a neuraminidase inhibitor is optional but may be desirable in some embodiments, particularly where the composition is intended for prophylaxis or treatment of human influenza viral infection. The sialic acid may be in the form of free sialic acid, or may be the conjugate or adduct of sialic acid with a saccharide such as galactose, lactose, etc. Sialic acid may be any sialic acid for example acids within the sialic acid family which includes at least 43 derivatives conjugates or adducts of the nine-carbon sugar neuraminic acid. What is important is that the sialic acid, in whatever form, be capable of binding the influenza virions. Furthermore, the lactoferrin shown in Table 1 may be any form of lactoferrin including lactoferrins free from chelation with iron (apolactoferrin), lactoferrins rich in iron (hololactoferrin) or combinations thereof. As used herein, "ICAM-1" includes any form of ICAM-1 including, without limitation, the extracellular domain portions of ICAM-1, and, in particular, soluble ICAM-1 ("sICAM-1"). It will be understood that in any of the compositions of the invention which call for ICAM-1, soluble ICAM-1 may suitably be included.

As depicted in Table 1, ingredients may be present in a range of percent weights of the composition. ICAM-1 (including soluble ICAM-1) may be present in an amount from about 0.00000001% to 10% by weight of composition. More typically, ICAM-1 (including soluble ICAM-1) may be present in an amount from 0.0000001% to 0.1% by weight of the composition. More typically, ICAM-1 (including soluble ICAM-1) may be present in an amount from 0.000001% to 0.01% by weight of the composition. ICAM-1 may be present in an amount of about 0.00000001%, 0.0000001%, 0.000001%, 0.00001%, 0.0001%, 0.001%, 0.01%, 0.05%, 1%, 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1.0%, 1.05%, 1.1%, 1.15%, 1.2%, 1.25%, 1.3%, 1.35%, 1.4%, 1.45%, 1.5%, 1.55%, 1.6%, 1.65%, 1.7%, 1.76%, 1.8%, 1.85%, 1.9%, 1.95%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, and 10.0% by weight of composition. In some embodiments, ICAM-1 may be present from 0.2% to 1.0% by weight of composition. In some embodiments, ICAM-1 may be present from about 0.000005% to 0.05% by weight of the composition. In preferred embodiments, ICAM-1 may be present from about 0.00005% to 0.005% by weight of the composition.

A neuraminidase inhibitor (e.g., quercetin, isoforms of quercetin including isoquercetin, etc.) may be present in an amount from about 0.00000001% to 10% by weight of composition. More typically, neuraminidase inhibitor may be present in an amount from 0.0000001% to 0.1% by weight of the composition. More typically, a neuraminidase inhibitor may be present in an amount from 0.000001% to 0.01% by weight of the composition. A neuraminidase inhibitor may be present in an amount of about 0.00000001%, 0.0000001%, 0.000001%, 0.00001%, 0.0001%, 0.001%, 0.01%, 0.05%, 1%, 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1.0%, 1.05%, 1.1%, 1.15%, 1.2%, 1.25%, 1.3%, 1.35%, 1.4%, 1.45%, 1.5%, 1.55%, 1.6%, 1.65%, 1.7%, 1.76%, 1.8%, 1.85%, 1.9%, 1.95%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, and 10.0% by weight of composition. In some embodiments, a neuraminidase inhibitor may be present from 0.2% to 1.0% by weight of composition. In some embodiments, a neuraminidase inhibitor may be present from about 0.000005% to 0.05% by weight of the composition. In preferred embodiments, a neuraminidase inhibitor may be present from about 0.00005% to 0.005% by weight of the composition.

Lactoferrin may be present in 0.0000001% to 10.0% by weight of the composition. Lactoferrin may be present in 0.00000025%, 0.0000003%, 0.0000004%, 0.0000005%, 0.0000006%, 0.0000007%, 0.00000075%, 0.0000008%, 0.0000009%, 0.000001%, 0.000002%, 0.000003%, 0.000004%, 0.000005%, 0.000006%, 0.000007%, 0.000008%, 0.000009%, 0.00001%, 0.00002%, 0.00003%, 0.00004%, 0.00005%, 0.00006%, 0.00007%, 0.00008%, 0.00009%, 0.0001%, 0.0002%, 0.0003%, 0.0004%, 0.0005%, 0.0006%, 0.0007%, 0.0008, 0.0009%, 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, and 10.0% by weight of composition. In preferred embodiments, lactoferrin may be present from 0.0000001-1.0% by weight of composition.

Lysozyme may be present in 0.000001% to 10.0% by weight of the composition. Lysozyme may be present in 0.000005%, 0.000006%, 0.000007%, 0.000008%, 0.000009%, 0.00001%, 0.00002%, 0.00003%, 0.00004%, 0.00005%, 0.00006%, 0.00007%, 0.00008%, 0.00009%, 0.0001%, 0.0002%, 0.0003%, 0.0004%, 0.0005%, 0.0006%, 0.0007%, 0.0008, 0.0009%, 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, and 10.0% by weight of composition. In preferred embodiments, lysozyme may be present from 0.000001-1.0% by weight of composition.

Sialic acid may be present in 0.000000001% to 10.0% by weight of the composition. Sialic acid may be present in 0.000005%, 0.000006%, 0.000007%, 0.000008%, 0.000009%, 0.00001%, 0.00002%, 0.00003%, 0.00004%, 0.00005%, 0.00006%, 0.00007%, 0.00008%, 0.00009%, 0.0001%, 0.0002%, 0.0003%, 0.0004%, 0.0005%, 0.0006%, 0.0007%, 0.0008, 0.0009%, 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, and 10.0% by weight of composition. In preferred embodiments, sialic acid may be present from 0.000001-1.0% by weight of composition. Sialic acid may be in the form of sialyllactose (e.g., 3'-sialyllactose and/or 6'-sialyllactose, etc.).

In another embodiment, a formula may have the ingredients as shown in Table 2.

TABLE 2

| Active Ingredients | Amount (% by weight of composition) |
| --- | --- |
| sICAM-1 | 0.00000001%-10.0% |
| Lactoferrin | 0.00000001%-10.0% |
| Lysozyme | 0.00000001%-10.0% |
| Sialic Acid | 0.00000001%-10.0% |
| neuraminidase inhibitor | 0.00000001%-10.0% |
| IgA. IgG. IgM | 0%-0.00000001%-10% |
| Zinc (ZnO$_2$) | 0%-0.00000001%-5% |
| Copper | 0%-0.00000001%-5% |
| Silver | 0%-0.00000001%-5% |

Carrageenan may be present in 0.0000005% to 10.0% by weight of composition. Lysozyme may be present in 0.0000005%, 0.0000006%, 0.0000007%, 0.0000008%, 0.0000009%, 0.000001%, 0.000002%, 0.000003%, 0.000004%, 0.000005%, 0.000006%, 0.000007%, 0.000008%, 0.000009%, 0.00001%, 0.00002%, 0.00003%, 0.00004%, 0.00005%, 0.00006%, 0.00007%, 0.00008, 0.00009%, 0.0001%, 0.0002%, 0.0003%, 0.0004%, 0.0005%, 0.0006%, 0.0007%, 0.0008%, 0.0009%, 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, and 10.0% by weight of composition. In preferred embodiments, carrageenan may be present from 0.000001-4.0% by weight of composition.

Zinc (e.g. zinc peroxide, etc.) may be present in 0.0000001 to 5% by weight of composition. Zinc may be present in 0.01%, 0.015%, 0.02%, 0.025%, 0.03%, 0.035%, 0.04%, 0.045%, 0.05%, 0.055%, 0.060%, 0.065%, 0.070%, 0.075%, 0.080%, 0.085%, 0.090%, 0.095%, 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1.0%, 1.05%, 1.1%, 1.15%, 1.2%, 1.25%, 1.3%, 1.35%, 1.4%, 1.45%, 1.5%, 1.55%, 1.6%, 1.65%, 1.7%, 1.76%, 1.8%, 1.85%, 1.9%, 1.95%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10.0%, 10.5%, 11.0%, 11.5%, 12.0%, 12.5%, 13.0%, 13.5%, 14.0%, 14.5%, 15.0%, 15.5%, 16.0%, 16.5%, 17.0%, 17.5%, 18.0%, 18.5%, 19.0%, 19.5%, and 20.0% by weight of composition. In preferred embodiments, zinc peroxide (ZnO$_2$) may be present from 0.000001%% to 5.0% by weight of composition.

Copper may be present in 0.00000001% to 5% by weight of composition. Copper may be present in 0.000005%, 0.000006%, 0.000007%, 0.000008%, 0.000009%, 0.00001%, 0.00002%, 0.00003%, 0.00004%, 0.00005%, 0.00006%, 0.00007%, 0.00008%, 0.00009%, 0.0001%, 0.0002%, 0.0003%, 0.0004%, 0.0005%, 0.0006%, 0.0007%, 0.0008, 0.0009%, 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10.0%, 10.5%, 11.0%, 11.5%, 12.0%, 12.5%, 13.0%, 13.5%, 14.0%, 14.5%, 15.0%, 15.5%, 16.0%, 16.5%, 17.0%, 17.5%, 18.0% 18.5%, 19.0%, 19.5%, and 20.0% by weight of composition. In preferred embodiments, copper may be present from 0.00001-5.0% by weight of composition.

Silver may be present in 0.00000001% to 5% by weight of composition. Silver may be present in 0.000005%, 0.000006%, 0.000007%, 0.000008%, 0.000009%, 0.00001%, 0.00002%, 0.00003%, 0.00004%, 0.00005%, 0.00006%, 0.00007%, 0.00008%, 0.00009%, 0.0001%, 0.0002%, 0.0003%, 0.0004%, 0.0005%, 0.0006%, 0.0007%, 0.0008, 0.0009%, 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10.0%, 10.5%, 11.0%, 11.5%, 12.0%, 12.5%, 13.0%, 13.5%, 14.0%, 14.5%, 15.0%, 15.5%, 16.0%, 16.5%, 17.0%, 17.5%, 18.0% 18.5%, 19.0%, 19.5%, and 20.0% by weight of composition. In preferred embodiments, silver may be present from 0.00001-5.0% by weight of composition.

The composition may also include odor-neutralizing compounds such as activated charcoal or sodium bicarbonate alone or in combination. Other odor-neutralizing compounds are contemplated for inclusion in the composition.

As depicted in Table 3, an exemplary antimicrobial composition may further include the following additional ingredients, either alone or in combination: marshmallow extract, calendula extract, citrus peel extract, honey, rosemary extracts, myrrh extract, *Helichrysum* extract, arrowroot extract, neem oil, vitamin C, vitamin E, and grapefruit seed extract. These additional ingredients may be present according to the following weights of the composition. The extraction solvents and extraction processes will be optimized for the antimicrobial composition to be most effective and tolerable.

TABLE 3

| Additional Ingredients. | |
| --- | --- |
| Supportive or Herbal Ingredients | Amount (% by weight of composition) |
| Marshmallow extract | 0.00000001%-5% |
| Calendula extract | 0.00000001%-10% |
| Citrus peel extract | 0.00000001%-10% |
| Honey extracts | 0.00000001%-10% |
| Rosemary extracts | 0.00000001%-10% |
| Myrrh extract | 0.00000001%-10% |
| Helichrysum extract | 0.00000001%-10% |
| Arrowroot extract | 0.00000001%-10% |
| Neem oil | 0.00000001%-10% |
| Vitamin C | 0.00000001%-10% |
| Vitamin E | 0.00000001%-10% |
| Grapefruit seed extract | 0.00000001%-10% |
| Activated charcoal | 0.00000001%-10% |
| Sodium bicarbonate | 0.00000001%-10% |

As depicted in Table 4, an exemplary antimicrobial composition may further include the following additional base ingredients either alone or in combination: a polyol, a humectant (such as but not limited to glycerine, aloe vera, or butylene glycol), an emollient (such as but not limited to shea butter, castor oil, coconut oil, caprylic acid, butyl stearate, or triglyceride), an occlusive substance (such as but not limited to petroleum jelly, dimethicone, lanolin, cocoa butter, shea butter, beeswax, plant butters, or carnauba wax). The addition and exact concentrations of these ingredients may be optimized to achieve a barrier function that does not clog pores, keeps active ingredients in their bioactive conformations and in place for at least 30 minutes, maintains osmolarity and pH similar to physiological mucus, is tolerable and effective when applied.

TABLE 4

| Additional Base Ingredients. | |
| --- | --- |
| Base Ingredients | Amount (% by weight of composition) |
| Humectant | 0.01%-10%-75% |
| Emollient | 0.01%-10%-75% |
| Occlusive | 0.01%-10%-75% |
| Preservatives | 0.00001%-0.5%-5% |
| Emulsifiers | 0.01%-1%-20% |
| Thickener | 0.001%-1%-10% |

Unless otherwise indicated, any excipient or additive may be included in an amount sufficient to serve its intended functional purpose without harming or irritating the respiratory tissues. Unless otherwise indicated, all excipients may be present in an amount from about 0.000001% or 0.01% to about 1, 5, 10, or 25% by weight of the composition. The carrier may be any pharmaceutically acceptable diluent and may be solid at room temperature or liquid at room temperature. Suitable carriers include water, alcohol (ethanol), Propylene glycol, isopropanol, propanediol, glycerin, benzyl alcohol, isostearly isosterate, caprylic/capric triglyceride, oleyl oleate, tocopherol acetate, decyl cocoate, squalene, span 40, coco-caprylate/caprate, span 80, tocopherol, osstearic acid, oleyl erucate, span 20, glyceryl isostearate, and caprylic/capric triglyceride. The carrier may be, for example, in the form of an aqueous solution, a water in oil emulsion, or an oil in water emulsion. The emulsion carrier will typically comprise from 0.0001% to about 10% by weight of an emulsifier suitable to stabilize the emulsion. In one embodiment, the composition is intended for oral use and may include one or more of the following ingredients: glucose syrup, soy lecithin, alginates, sucralose, corn syrup, gelatin, erythritol, lecithin, plant mucins, carrageenan, chicory root extract, malitol, and *stevia*. In both oral and nasal formulations, it should be noted that the excipients should not interfere with the biological activity of the actives and should be compatible in solution with the actives. The excipients should also not penetrate the epithelia (respiratory membranes). Accordingly, it is desirable to have a higher solubility of the actives in the base composition to maintain them in solution and prevent penetration of the actives into the epithelia. In nasal formulations, the excipients should serve to maintain moisture in the mucosa and the compositional film thereon, such that the active ingredients do not precipitate from solution. In some embodiments, the carrier will comprise water, and a secondary solvent of lower volatility than the water in which the actives are also soluble. Ideally, the carrier and excipients are selected such that they have a polarity that is closer to the polarity of the active ingredients than to the polarity of the epithelia. The secondary solvent may serve to keep the actives soluble after water has evaporated. In oral formulations, loss of moisture is less important and it may be desirable to select excipients so as to retard the dissolution of the composition in the saliva.

Prepared compounds are purified using conventional methods to obtain compounds free of impurities. Prepared compounds are >75%, >80%, >85%, >90%, >95%, >96%, >97%, >98%, >99%, >99.5% pure. Optionally, preferred compounds are >99% pure.

Intracellular Adhesion Molecule (ICAM-1)

ICAM-1 is a member of the immunoglobulin superfamily of adhesion molecules. It is an integral membrane protein 505 amino acids long and has: i) five immunoglobulin-like extra-cellular domains at the amino-terminal (extracellular)

end, ii) a hydrophobic transmembrane domain (454-477); and iii) a short cytoplasmic domain at the carboxy-terminal end (478-505). Most rhinoviruses use ICAM-1 expressed on nasal epithelial membranes to gain entry into cells. There are three main types of rhinoviruses (HRV A, B, and C). HRV A and B can be further subdivided into about 100 subtypes. 85% of HRVA and 100% of HRVB use ICAM-1 to enter cells. HRV C rarely causes noticeable illness. According to the techniques herein, the addition of partially or fully purified soluble forms of ICAM-1, or any of its recombinantly engineered domains, to the compositions of the disclosure may keep the molecule in a stable form whereby it can competitively inhibit rhinovirus particles from interacting with endogenous ICAM-1 on cell membranes, thus preventing the first step of infection.

In some embodiments, the antimicrobial/antiviral compositions may be comprised of ICAM-1 inhibitors. ICAM-1 inhibitors used in the antimicrobial compositions include, but are not limited to, an anti-ICAM-1 antibody, cytokine, CD11a, ezrin (EZR), CD18, glycyrrhetinic acid, pyrrolidinedithiocarbamate, NFkB activation inhibitor, heterocyclic thiazole, lipoic acid, efalizumab, 4-[(4-Methylphenyl)thio] thieno[2,3-c]pyridine-2-carboxamide, silibinin, stilbenes, (+)-epigalloyl-catechin-gallate [(+)-EGCG], extracts of Piper sarmentosum, and combinations thereof. In some embodiments, the anti-ICAM-1 antibody is efalizumab (RAPTIVA).

Sialic Acid and Neuraminidase Inhibitors

Sialic acid rich oligosaccharides on cells of the upper respiratory tract normally help keep water on the surface and create a negative charge. Sialic acid is a generic term for the N- or 0-substituted derivatives of neuraminic acid, a monosaccharide with a nine-carbon backbone. It is also the name for the most common member of this group, N-acetyl-neuraminic acid (Neu5Ac or NANA). Influenza or other viruses are known to bind sialic acid residues via the hemagglutinin (HA) receptor on their surface after which they begin to replicate. When replication is complete, a viral enzyme, neuraminidase cleaves the viral particles so they are free to bind and infect other cells. According to the techniques herein, partially or fully purified sialic acid such as, e.g. N-acetylneuraminic acid (Neu5Ac), or any other neuraminic acid derivative or any of their recombinantly engineered domains may be added to keep the molecule in a stable form in which it may competitively inhibit influenza virus particles from interacting with sialic acid on respiratory cells or erythrocytes. The sialic acid family includes 43 derivatives of the nine carbon sugar neuraminic acid. In nature, they are usually found as components of oligosaccharide chains of mucins, glycoproteins, and glycolipids. Various species susceptible to influenza are thought to have slight variations in their sialic acid-galactose linkages. Influenza viruses that infect a particular species are thought to have specific affinity for sialic acid bound to galactose in that species-specific conformation. For example, on human respiratory epithelial cells sialic acid is primarily attached to galactose via an alpha 2,6 linkage so influenza viruses that infect humans are usually specifically targeted to that conformation of sialic acid. Human epithelial cells also have other less predominant types of sialic acid-galactose linkages such as the alpha 2,3 linkage that may be the predominant conformation in another species such as pigs. As such, one theory of how influenza might spread from one species to another is by having specificity for a conformation that is found in more than one species, or in mutating to become specific for another one.

Nasal mucous and other exocrine secretions contain sialic acid in soluble form which may serve a protective function by binding influenza viruses and other microorganisms and immobilizing them. Influenza viruses have evolved a method for cleaving themselves from soluble sialic acid using an enzyme called neuraminidase. Several antiviral drugs such as Tamiflu serve as neuraminidase inhibitors. In this regard, they keep the virus immobilized and unable to infect epithelial cells. There is no prior art attempting to use neuraminidase inhibitors in a topical solution applied to the nostrils to prevent infection. It is mainly administered systemically to cure infection. Quecertin, a bioflavanoid found in citrus peels and many other fruits and vegetables is an example of a naturally occurring neuraminidase inhibitor.

In some embodiments, antimicrobial compositions include neuraminidase inhibitors. Neuraminidase inhibitors include, but are not limited to, quercetin, oseltamivir, zanamivir, laninamivir, amantadine, peramivir, and any of their analogues.

Anti-Viral Agents

The anti-viral agents of the present invention may be obtained by natural processes (e.g., by inducing an animal, plant, fungi, bacteria, etc., to produce an analog of ICAM-1, or by inducing an animal to produce polyclonal or monoclonal anti-ICAM-1 anti-idiotypic, etc.); synthetic methods (e.g., by using the Merrifield method for synthesizing polypeptides of a functional derivatives of ICAM-1, etc.); recombinant technology (e.g., to produce the anti-viral functional derivatives of ICAM-1 in diverse hosts (e.g., yeast, bacteria, fungi, cultured mammalian cells, etc.), recombinant plasmids or viral vectors, or proteolysis. The choice of which method to employ depends upon factors such as convenience, desired yield, etc. It is not necessary to employ only one of the above-described methods, processes, or technologies to produce a particular anti-viral agent; the above-described processes, methods, and technologies may be combined in order to obtain a particular anti-viral agent. Ingredients are balanced to create synergistic effects.

Lactoferrin

Lactoferrin is naturally present in exocrine secretions including nasal mucous and serves a protective function against microorganisms. It is highly cationic, anti-bacterial, anti-viral, and anti-fungal. In tears, concentrations range from 1-3 mg/mL accounting for 15-30% of total protein. Human milk contains 1 mg/mL and bronchial secretions can have as much as 11.5% total protein. Concentrations in mucous range from 1 µg/mL to 8 µg/mL with challenge and from about 1-3% total protein (Raphael et al 1989). Levels of lactoferrin in mucosal secretions are thought to decrease with age, which might make older adults more susceptible to respiratory infection.

Lactoferrin exists in monomeric and tetrameric forms and tends to polymerize at high concentrations. It is a glycoprotein of approximately 703 amino acids and approximately 80 kD. Despite a 69% homology between human lactoferrin and bovine lactoferrin, in some studies, bovine lactoferrin was required at $\frac{1}{10}$ the concentration of human lactoferrin for an antimicrobial effect. Different types of lactoferrin may be more beneficial for certain mutations or types of infective organisms than others and can be tested to be optimized in the case of pending epidemics. In studies of herpes simplex virus (topical application) and hepatitis C infection, lactoferrin was protective before contact with the virus but not after, making application to the site of infection (such as nasal membranes) more relevant than systemic application.

Lysozyme

Lysozyme, like lactoferrin, is normally present in exocrine secretions. It is also highly cationic, anti-bacterial, anti-viral, and anti-fungal. According to one study (Atsushi et al 1998), the average concentration in mucous is 20-30 μg/mL. In tears, the concentration of lysozyme is about 103 mg/mL according to Raphael et al 1989. Levels of lysozyme in mucous are also thought to decrease with age.

Mucosal Antibodies

Nasal secretions contain immunoglobulins offering antibody mediated defense and research indicates a majority is the secretory form of IgA (sIgA) (Kirkeby et al., 2000). S-IgA antibodies prevent microbial attachment and the absorption of molecular antigens including potential allergens. Certain bacteria produce IgA proteases, by cleaving IgA, these enzymes may interfere with the barrier function of these antibodies. Research indicates that cleavage of IgA may result in atopic disease. Other antibodies most commonly found in nasal secretions and which may serve protective functions are IgG and IgM (Kirkeby et al 2000). By augmenting the amounts of these antibodies, the present disclosure may protect against undesirable irritants or pathogens.

Recombinant Engineering

Several possible sources of the aforementioned biological compounds exist such as human or bovine exocrine secretions. However, these may be in limited supply and pose safety risks. Recombinant bio-manufacturing is another possible source of the compounds. Bio-manufacturing can utilize genetically engineered microorganisms like bacteria, fungi, animal cells, yeast, or plants (including algae). Expression in mammalian cell lines, bacteria, and yeast is often costly. One of the reasons for this is the need for purification. Algae offer several advantages to other methods in that very high levels of purification are often not required. It is estimated that protein production in plants can be as much as four orders of magnitude less expensive than production in mammalian cell culture on a per gram of unpurified protein basis. In addition, plant material such as algae is for the most part "Generally Regarded as Safe" as are their genetically modified counterparts. Commercial scale production seems feasible since recombinant algal bioreactors for several classically expensive biological molecules has proven promising (see Rasala et al Plant Biotech. 2010).

Methods of Treatment

Novel methods and compositions for enhancing the filtering capabilities of the respiratory membranes and protecting against airborne pathogens are described herein. The delivery methods of the present disclosure maximize exposure of the airway to antimicrobial/antiviral compositions for protection against airborne pathogens. The novel therapeutic methods may also involve administration of an antimicrobial composition as a therapeutic agent.

In any of the above aspects or embodiments, the method may reduce the growth of a respiratory infection, shrink the infection, or eradicate the infection. In related embodiments, the infection shrinks by 5%, 10%, 25%, 50%, 75%, 85%, 90%, 95%, or 99% or more as compared to its original size.

In any of the above aspects or embodiments, the methods may involve administering the therapeutic agent multiple times per day. In yet further related embodiments, the methods may involve administering the therapeutic agent on a first day and repeating the administration on one or more subsequent days. In yet further related embodiments, the first day and one or more subsequent days are separated by between 1 day and about 3 weeks. In related embodiments, the therapeutic agent and another agent are coadministered. In related embodiments, the therapeutic agent and other agents are administered in a ratio of about 1:2, 1:4, 1:10, 1:20, 1:25, 1:50, 1:100, 1:200, or any ratio there between (weight ratio of therapeutic agent: agent). It is further contemplated within the scope of the disclosure that the therapeutic agent may be administered over the course of one or more cycles. In any of the above aspects or embodiments, the therapeutic agent and another agent can be delivered simultaneously.

In any of the above aspects or embodiments, the therapeutic agent may be any antimicrobial composition as described herein that is used to prevent or treat a respiratory disease or disorder. In related embodiments, the respiratory disease or disorder is caused by airborne pathogens. In certain embodiments, the therapeutic agent is an antimicrobial/antiviral agent.

The antimicrobial agent can be any agent well known in the art, including, but not limited to, those described herein.

In yet other embodiments, the therapeutic agent may be a therapeutic antibody. The therapeutic antibody can be any therapeutic antibody well known in the art, including, but not limited to, those described herein.

In embodiments, the therapeutic agent may be a therapeutic nucleic acid molecule. The therapeutic nucleic acid molecule can be any therapeutic nucleic acid molecule well known in the art.

In embodiments, the therapeutic agent may be a radioisotope. The radioisotope may be any radioisotope well known in the art.

In other embodiments, the therapeutic agent may be a combination of two or more drug compounds.

In any of the above aspects or embodiments, the methods involve administering a therapeutically effective amount of an immunotherapeutic agent. The immunotherapeutic agent may be any suitable means by which to trigger a further immune response that targets destruction of the cells of the infection.

In embodiments, the immunotherapeutic agent enhances the immunomodulatory effects of the therapeutic agent. In related embodiments, the immunotherapeutic agent further reduces the growth of the infection or further shrinks the infection.

The immunotherapeutic agent may be administered before, during, or after the therapeutic agent has been administered. In embodiments, the immunotherapeutic agent is administered before the first administration of the therapeutic agent. In embodiments, the immunotherapeutic agent is administered simultaneously with the first administration of the therapeutic agent.

In any of the above aspects or embodiments, the therapeutic agent and the immunotherapeutic agent can be administered in a ratio of about 1:2, 1:4, 1:10, 1:25, 1:50, 1:100, 1:200, or any ratio there between (weight ratio of therapeutic agent: immunotherapeutic agent).

In any of the above aspects or embodiments, the immunotherapeutic agent can be administered intranasally, locally, regionally, or systemically (e.g. intravenously, etc.).

In any of the above aspects or embodiments, the therapeutic agent and the immunotherapeutic agent may be coupled.

Therapeutic Agents

The present disclosure contemplates any therapeutic agent suitable for use in the methods described herein (e.g., any type of antimicrobial/antiviral agent to treat respiratory disease, etc.). Suitable therapeutic agents include, but are not limited to, pharmaceutical drugs or compounds (i.e., small molecule drugs), therapeutic antibodies, therapeutic proteins or biologics (e.g., hormone therapies, etc.), and nucleic acid molecules (e.g., siRNAs, etc.).

In some embodiments, the therapeutic agent is an agent that has been shown to have antimicrobial properties against infectious organisms. In related embodiments, the therapeutic agent is an existing market-approved pharmaceutical drug or other market-approved composition for treating infection using a conventional approach.

In some embodiments, the therapeutic agent is an anti-microbial composition as described herein. In some embodiments, antimicrobial compositions include compositions with anti-bacterial, anti-viral, and/or anti-fungal properties. Antimicrobial compositions include but are not limited to: an antibody such as IgA, IgG, or IgM, a soluble ICAM-1, an ICAM-1 inhibitor, sialic acid, a neuraminidase inhibitor, lactoferrin, a lysozyme, a zinc compound, silver, silver compounds, copper, copper compounds, and combinations thereof. Neuraminidase inhibitors include but are not limited to: quercetin, oseltamivir, zanamivir, laninamivir, and per-amivir. ICAM-1 inhibitors include but are not limited to: soluble ICAM-1, an anti-ICAM-1 antibody, cytokine, CD11a, ezrin (EZR), CD18, glycyrrhetinic acid, pyrrolidin-edithiocarbamate, NFkB activation inhibitor, heterocyclic thiazole, lipoic acid, efalizumab, 4-[(4-Methylphenyl)thio] thieno[2,3-c]pyridine-2-carboxamide, silibinin, stilbenes, (+)-epigalloyl-catechin-gallate [(+)-EGCG], and combinations thereof. In some embodiments, the anti-ICAM-1 antibody is efalizumab (RAPTIVA).

The disclosure also contemplates any derivative form of the aforementioned pharmaceutical agents and therapeutic agents. Common derivatizations may include, for example, adding a chemical moiety to improve solubility and/or stability, or a targeting moiety, which allows more specific targeting of the molecule to a specific cell or region of the body. The pharmaceutical agents may also be formulated in any suitable combinations, wherein the drugs may either mixed in individual form or coupled together in a manner that retains the functionality of each drug. The drugs may also be derivatized to include a radioisotope or other cell-killing moiety to make the molecule even more effective at killing the cell. In addition, the drugs, or a portion thereof, may be modified with fluorescence compound or other detectable labels which may allow tracking of the drug or agent in the body or within the tumor. The pharmaceutical drug or otherwise any of the aforementioned therapeutic agents may be provided in a precursor form such that they the drug only gains its activity or function after it has been processed in some manner, e.g., metabolized by a cell.

Therapeutic antibodies contemplated by the present disclosure may include any isotype (IgA, IgG, IgE, IgM, or IgD) of an anti-microbial or antiviral antibody or immune-active fragment or derivative thereof. Such fragments may include, for example, single-chain variable fragments (scFv), antigen-binding fragment (Fab), crystallizable frag-ment (Fc) modified to contain an antigen or epitope binding region, and domain antibodies. Derivatized versions of therapeutic antibodies may include, for example, diabodies, nanobodies, bispecific antibodies, and virtually any anti-body-derived structure which contains or is engineered to contain an appropriate and effective antigen binding site.

Examples of antibody-based antimicrobial therapies that may be utilized by the disclosure can include, for example, an antibody specific for ICAM-1. In some embodiments, the anti-ICAM-1 antibody is efalizumab (RAPTIVA).

The disclosure also contemplates that preventing or treat-ing respiratory disease may be effected using a nucleic acid molecule that targets a specified "target gene" that has a role in infection. The effect of the nucleic acid molecule on the target gene may include gene silencing, mRNA destruction, or inhibited transcription, or the like, such that the level of expression and/or conversion of the target gene to an oper-able encoded polypeptide are substantially affected (up or down) such that the cancer is inhibited and/or destroyed by the agent. The term "target gene" refers to nucleic acid sequences (e.g., genomic DNAs or mRNAs, etc.) encoding a target protein, peptide, or polypeptide, or that encode for or are regulatory nucleic acids (e.g., a "target gene" for purpose of the instant disclosure can also be a miRNA or miRNA-encoding gene sequence, etc.) which have a role in infection. In certain embodiments, the term "target gene" is also meant to include isoforms, mutants, polymorphisms, and splice variants of target genes.

Any nucleic acid based agent well known in the art may be suitable for use in the disclosure. Exemplary types of nucleic acid based agents include, but are not limited to, single stranded ribonucleic acid agents (e.g., microRNAs, etc.), antisense-type oligonucleotide agents, double-stranded ribonucleic acid agents, and the like.

Methods for constructing therapeutic nucleic acids are well known in the art. For example, interfering RNA can be assembled from two separate oligonucleotides, where one strand is the sense strand and the other is the antisense strand, wherein the antisense and sense strands are self-complementary (i.e., each strand comprises a nucleotide sequence that is complementary to nucleotide sequence in the other strand; such as where the antisense strand and sense strand form a duplex or double stranded structure); the antisense strand comprises nucleotide sequence that is complementary to a nucleotide sequence in a target nucleic acid molecule or a portion thereof and the sense strand comprises nucleotide sequence corresponding to the target nucleic acid sequence or a portion thereof.

Alternatively, interfering RNA may be assembled from a single oligonucleotide, where the self-complementary sense and antisense regions are linked by means of nucleic acid based or non-nucleic acid-based linker(s). The interfering RNA may be a polynucleotide with a duplex, asymmetric duplex, hairpin or asymmetric hairpin secondary structure, having self-complementary sense and antisense regions, wherein the antisense region comprises a nucleotide sequence that is complementary to nucleotide sequence in a separate target nucleic acid molecule or a portion thereof and the sense region having nucleotide sequence corresponding to the target nucleic acid sequence or a portion thereof. The interfering RNA can be a circular single-stranded polynucle-otide having two or more loop structures and a stem com-prising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNA interference.

Methods for administering/delivering therapeutic nucleic acids are well known in the art. For example, therapeutic nucleic acid molecules may be delivered in a delivery vehicle, such as a lipid vesicle or other polymer carrier material known in the art. Non-limiting examples of addi-tional lipid-based carrier systems (which may be prepared with at least one modified cationic lipid of the disclosure) suitable for use in the present disclosure include lipoplexes (see, e.g., U.S. Patent Publication No. 20030203865; and Zhang et al., J. Control Release, 100:165-180 (2004)), pH-sensitive lipoplexes (see, e.g., U.S. Patent Publication No. 2002/0192275), reversibly masked lipoplexes (see, e.g., U.S. Patent Publication Nos. 2003/0180950), cationic lipid-based compositions (see, e.g., U.S. Pat. No. 6,756,054; and U.S. Patent Publication No. 2005/0234232), cationic liposomes (see, e.g., U.S. Patent Publication Nos. 2003/0229040, 2002/0160038, and 2002/0012998; U.S. Pat. No. 5,908,635; and PCT Publication No. WO 01/72283), anionic liposomes (see, e.g., U.S. Patent Publication No. 2003/0026831), pH-sensitive liposomes (see, e.g., U.S. Patent Publication No. 2002/0192274; and AU 2003/210303), antibody-coated liposomes (see, e.g., U.S. Patent Publication No. 2003/0108597; and PCT Publication No. WO 00/50008), cell-type specific to liposomes (see, e.g., U.S. Patent Publication No. 2003/0198664), liposomes containing nucleic acid and peptides (see, e.g., U.S. Pat. No. 6,207,456), liposomes containing lipids derivatized with releasable hydrophilic polymers (see, e.g., U.S. Patent Publication No. 2003/0031704), lipid-entrapped nucleic acid (see, e.g., PCT Publication Nos. WO 03/057190 and WO 03/059322), lipid-encapsulated nucleic acid (see, e.g., U.S. Patent Publication No. 2003/0129221; and U.S. Pat. No. 5,756,122), other liposomal compositions (see, e.g., U.S. Patent Publication Nos. 2003/0035829 and 2003/0072794; and U.S. Pat. No. 6,200,599), stabilized mixtures of liposomes and emulsions (see, e.g., EP1304160), emulsion compositions (see, e.g., U.S. Pat. No. 6,747,014), and nucleic acid micro-emulsions (see, e.g., U.S. Patent Publication No. 2005/0037086).

If suitable, any of the agents of the disclosure, including pharmaceutical drugs, biologics, and therapeutic antibodies, may also be delivered via the above described carrier systems. All carrier systems may further be modified with a targeting moiety or the like in order to facilitate delivery of the composition to a site of infection in the respiratory airways.

It will be appreciated that conventional means for delivering active agents are often severely limited by biological, chemical, and physical barriers. Typically, these barriers are imposed by the environment through which delivery occurs, the environment of the target for delivery, or the target itself. Biologically or chemically active agents are particularly vulnerable to such barriers. In the delivery to animals of biologically active or chemically active pharmacological and therapeutic agents, physical and chemical barriers are imposed by the body. Examples of physical bathers are the skin and various organ membranes that are traversed before reaching a target, and examples of chemical barriers include, but are not limited to, variations in pH, lipid bilayers, and degrading enzymes. The cellular membrane also represents an important barrier having a significant effect on the effectiveness of drug delivery.

Immunotherapeutic Agents

In another aspect, the disclosure employs one or more immunotherapeutic agents that may further enhance the respiratory infection clearing effects imparted by the use of the antimicrobial/antiviral therapeutic agent. For example, the immunotherapeutic agent may be delivered after the effects of the antimicrobial agent has set in, but the disclosure is not limited to this concept. The disclosure contemplates any administration regimen involving multiple agents so long as the therapeutic benefits attributable to each of the agents may occur. It is also contemplated within the scope of the disclosure that administration of the one or more immunotherapeutic agents may have immunostimulatory activity that provides prophylaxis against further recurrence of an infection. This immunostimulatory effect may be achieved when the agent is given intranasally or systemically.

Those skilled in the art will appreciate that an immunotherapeutic agent is a treatment that aims to use an individual's own immune system to fight infection or disease. This may be accomplished by boosting the individual's own immune system or to provide supplemental pieces of an otherwise defective or deficient immune system.

Immunotherapy is a form of biological therapy that can be used in the present disclosure to supplement and/or enhance the effects of treating with the therapeutic agent. There are generally two recognized forms of immunotherapy, which are referred to as active immunotherapies and passive immunotherapies. Active immunotherapies stimulate the body's own immune system to fight a disease. Passive immunotherapies use immune system components, such as antibodies, prepared outside the body, to enhance the body's immune response level. Immunotherapies may also work by targeting certain types of cells or antigens (specific immunotherapies) or they may work by more generally stimulating the immune system (non-specific immunotherapies, or sometimes referred to as adjuvants). Some examples of immunotherapies contemplated by the disclosure include monoclonal antibody therapy, non-specific immunotherapies and adjuvants (substances which boost the immune response such as interleukin-2 and interferon-alpha), immunomodulating drugs (such as thalidomide and lenalidomide), and vaccines.

Accordingly, immunotherapeutic agents, which may also be referred to as "immunomodulators" may include, for example, interleukins (e.g., IL-2, IL-7, or IL-12, etc.), certain other cytokines (e.g., interferons, growth colony stimulating factor (G-CSF), imiquimod, etc.), chemokines, and other types of agents, which can include antigens, epitopes, antibodies, monoclonal antibodies, or even a delivery vehicle to deliver one or more of these compounds, and may even also include recombinant immune system cells. Such immunotherapeutic agents may include recombinant forms, synthetic forms, and natural preparations (see D'Alessandro, N. et al., Cancer Therapy: Differentiation, Immunomodulation and Angiogenesis, New York: Springer-Verlag, 1993).

In another embodiment, the immunotherapeutic agent takes advantage of the body's innate immune system and has the effect when introduced of triggering the innate immune response against the unwanted pathogens.

Introduction of the immunotherapeutic agents of the disclosure, may be achieved using any suitable approach, including by local or regional administration of the agent at, near, or within the respiratory infection. The agent may also be delivered, where suitable, via gene therapy. For example, the antibody-inducing antigen may be introduced by injecting or otherwise directly administering a genetic vector or otherwise nucleic acid molecule capable of expressing the desired antigen. The antigens themselves may also be directly administered into the target infected tissue.

Target Respiratory Diseases

The present disclosure contemplates treating a broad range of respiratory diseases, including infections of all types, locations, sizes, and characteristics. For example, the methods of the disclosure are suitable for treating, for example, sinusitis, influenza, and rhinovirus (the common cold).

In other embodiments, virtually any type of respiratory-related infection may be treated by the present disclosure including, but not limited to, the following respiratory infections: tonsillitis, pharyngitis, laryngitis, sinusitis, otitis media, certain types of influenza, bronchitis, pneumonia, and the common cold.

The compositions of the invention are contemplated to be suitable for prophylaxis and/or treatment of infection from any serotype of human rhinovirus (HRV). HRV may include, without limitation, the species Rhinovirus A (including serotypes HRV-A1, HRV-A2, HRV-A7, HRV-A8, HRV-A9, HRV-A10, HRV-A11, HRV-A12, HRV-A13, HRV-A15, HRV-A16, HRV-A18, HRV-A19, HRV-A20, HRV-A21, HRV-A22, HRV-A23, HRV-A24, HRV-A25, HRV-A28, HRV-A29, HRV-A30, HRV-A31, HRV-A32, HRV-A33, HRV-A34, HRV-A36, HRV-A38, HRV-A39, HRV-A40, HRV-A41, HRV-A43, HRV-A44, HRV-A45, HRV-A46, HRV-A47, HRV-A49, HRV-A50, HRV-A51, HRV-A53, HRV-A54, HRV-A55, HRV-A56, HRV-A57, HRV-A58, HRV-A59, HRV-A60, HRV-A61, HRV-A62, HRV-A63, HRV-A64, HRV-A65, HRV-A66, HRV-A67, HRV-A68, HRV-A71, HRV-A73, HRV-A74, HRV-A75, HRV-A76, HRV-A77, HRV-A78, HRV-A80, HRV-A81, HRV-A82, HRV-A85,HRV-A88, HRV-A89, HRV-A90, HRV-A94, HRV-A95, HRV-A96, HRV-A98, HRV-A100, HRV-A101, HRV-A102 and HRV-A103), Rhinovirus B (including the serotypes HRV-B3, HRV-B4, HRV-B5, HRV-B6, HRV-B14, HRV-B17, HRV-B26, HRV-B27, HRV-B35, HRV-B37, HRV-B42, HRV-B48, HRV-B52, HRV-B69, HRV-B70, HRV-B72, HRV-B79, HRV-B83, HRV-B84, HRV-B86, HRV-B91, HRV-B92, HRV-B93, HRV-B97, and HRV-B99), and Rhinovirus C (including, without limitation, serotypes HRV-C1, HRV-C2, HRV-C3, HRV-C4, HRV-05, HRV-C6, HRV-C7, HRV-C8, HRV-C9, HRV-C10, HRV-C11, HRV-C12, HRV-C13, HRV-C14, HRV-C15, HRV-C16, HRV-C17, HRV-C18, HRV-C19, HRV-C20, HRV-C21, HRV-C22, HRV-C23, HRV-C24, HRV-C25, HRV-C26, HRV-C27, HRV-C28, HRV-C29, HRV-C30, HRV-C31, HRV-C32, HRV-C33, HRV-C34, HRV-C35, HRV-C36, HRV-C37, HRV-C38, HRV-C39, HRV-C40, HRV-C41, HRV-C42, HRV-C43, HRV-C44, HRV-C45, HRV-C46, HRV-C47, HRV-C48, HRV-C49, HRV-050 and HRV-051). In some embodiments, the inventive compositions are contemplated to be useful in the prophylaxis or treatment of viral infection from any rhinovirus or enterovirus, and in particular any virus which binds Intercellular adhesion molecule 1 (ICAM-1). The compositions of the invention are also contemplated to be suitable for prophylaxis and/or treatment of infection from any serotype of human influenza virus, including without limitation, those of the genera Influenzavirus A, Influenzavirus B, and Influenzavirus B, including the species influenza A virus (including, without limitation, serotypes H1N1, H2N2, H3N2, H5N1, H7N7, H1N2, H9N2, H7N2, H7N3, H10N7, and H7N9 to name a few), influenza B virus, and influenza C virus. In some embodiments, the inventive compositions are contemplated to be useful in the prophylaxis or treatment of viral infection from any sialic acid-binding virus, including influenza virus, reovirus, adenovirus and/or rotavirus. When sprayed into the nasal cavity and/or mouth, the compositions of the invention form a deposit on the mucosa, ideally having a long residence time (e.g., at least 1 minute, at least 5 minutes, at least 10 minutes, at least 15 minutes, at least 20 minutes, at least 25 minutes, at least 30 minutes, etc.) on the mucosa, but desirably do not cause excessive drying or irritation of the mucosa. Preferred compositions according to the invention are applied to the nasal and/or oral mucosa for prophylaxis or treatment of human rhinovirus and human influenza virus infection.

The present disclosure may generally treat and/or prevent all forms of the above infections. For example, the method of the disclosure advantageously may treat or prevent infections arising in any part of the respiratory tract including, but not limited to, the upper respiratory tract (nose, sinuses, larynx and pharynx) and the lower respiratory tract (trachea, primary bronchi, bronchial tubes, bronchioles, and lungs).

Reduction of infection means a measurable decrease in growth of the infection. For example, and without limitation, the infection may be reduced by at least about a factor of 10 (for example 100, 1000-fold or more) or by decrease of at least about 10% (for example at least about 20, 30, 40, 50, 60, 70, 80, 90, 95, 99 or 100%) as compared to the growth measured over time prior to treatment as defined herein. The reduction in infection according to the invention is ideally of a statistically significant degree as compared to otherwise identical infected tissues in the absence of the active ingredients contained the composition of the invention.

Full eradication of the infection may also be achieved through methods of the disclosure. Eradication refers elimination of the infection and infectious organisms. The infection is considered to be eliminated when it is no longer detectable using detection methods known in the art.

Pharmaceutical Compositions

The disclosure provides pharmaceutical compositions for use in any of the methods described herein. The pharmaceutical compositions may contain a antimicrobial/antiviral therapeutic agent and optionally, an immunotherapeutic agent.

In embodiments, the pharmaceutical compositions include a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil, olive oil, gel (e.g., hydrogel, etc.), castor oil, and the like. Saline is a preferred carrier when the pharmaceutical composition is administered intravenously. Saline solutions and aqueous dextrose and glycerol solutions may also be employed as liquid carriers, particularly for injectable solutions.

The pharmaceutically acceptable carrier may be selected to provide a specified residence time in the mucosa of a subject. In some embodiments, the "residence time" of the inventive compositions on the mucosa represent average residence times from studies involving multiple applications (intranasal and/or oral) using a sample of multiple individuals sufficient to approximate the population at large. In some embodiments, at least 25% (and preferably, at least 30%, or at least 40% or at least 50%, or at least 60%, or at least 70%, or at least 80%, or at least 90%) by weight of the initially applied active ingredients remain on the mucosa after the specified duration of time. In some embodiments, the pharmaceutically acceptable carrier at 25° C. has the Hansen Solubility Parameters of energy from dispersion ($\delta_d$), energy from dipolar intermolecular force between molecules ($\delta_p$), energy from hydrogen bonds ($\delta_h$) of between about 15 and about 18, about 12 and about 15, about 21 and about 25, respectively.

The pharmaceutically acceptable carrier may be aqueous. In some embodiments, the pharmaceutically acceptable carrier is free of mercurial preservatives. The solvent may be 1,2-propanediol, 1,3-propanediol and a variety of aqueous carriers can be used, e.g. buffered water, 0.9 percent saline, buffered aqueous-ethanol solutions and the like. Combinations of any of these carriers are within the scope of the invention. These compositions can be sterilized by conventional, well-known sterilization techniques, or can be sterile filtered. The resulting solutions can be packaged for use as is or mixed as an adjuvant to another medication. A composition can contain pharmaceutically acceptable auxiliary substances as required to approximate physiological conditions, such as pH adjusting and buffering agents, tonicity adjusting agents, taste modifiers, sweeteners, wetting agents and the like, for example, sodium acetate, sodium lactate, sodium chloride, potassium chloride, calcium chloride, sorbitan monolaurate, triethanolamine oleate, etc. In some embodiments, the pharmaceutically acceptable carrier is a mixture of water and a polyol. In some embodiments, the pharmaceutically acceptable carrier is a mixture of water and propanediol (e.g. 1,2-propendediol, 1,3-propanediol, etc.). In some embodiments, the pharmaceutical composition is a mixture of water and glycerin. The pharmaceutically acceptable carrier may be about 1%-about 35% (e.g. about 5%-about 30%, etc.) aqueous solution of propanediol or glycerin by weight of the aqueous carrier. Some pharmaceutically acceptable carriers include 20% aqueous solution of 1,3-propanediol, 20% aqueous solution of glycerin, 10% aqueous solution of 1,3-propanediol, 10% aqueous solution of glycerin, 20% aqueous solution of 1,3-propanediol with 1% sunflower oil and 5% polysorbate 80, 20% aqueous solution of glycerin with 1% sunflower oil and 5% polysorbate 80, 10% aqueous solution of 1,3-propanediol with 1% sunflower oil and 5% polysorbate 80, 10% aqueous solution of glycerin with 1% sunflower oil and 5% polysorbate 80, the Versaflex V-175 polymeric emulsifier system (i.e. sucrose palmitate, glyceryl stearate, glyceryl sterate citrate, sucrose, mannan, and Xanthan gum), the Versaflex V-175 polymeric emulsifier system with 3% sunflower oil, the Versaflex V-175 polymeric emulsifier system with 3% sunflower oil and about 5 to about 30% propanediol or glycerin, the Versaflex V-175 emulsifier system with 3% acetylated monoglyceride, and the Versaflex V-175 emulsifier system with 3% acetylated monoglyceride and about 5 to about 30% propanediol or glycerin.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin, the contents of which are hereby incorporated by reference in its entirety. Such compositions will generally contain a therapeutically effective amount of the therapeutic agent and/or the immunotherapeutic agent, in purified form, together with a suitable amount of carrier so as to provide the form for proper administration to the patient. The formulation should suit the mode of administration.

In embodiments, the therapeutic agent and/or the immunotherapeutic agent are administered locally as an immediate release or controlled release composition, for example by controlled dissolution and/or the diffusion of the active substance. Dissolution or diffusion controlled release can be achieved by incorporating the active substance into an appropriate matrix. A controlled release matrix may include one or more of shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated metylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

In related embodiments, the controlled release matrix is a hydrogel. A hydrogel is a three-dimensional, hydrophilic or amphiphilic polymeric network capable of taking up large quantities of water. The networks are composed of homopolymers or copolymers, which are insoluble due to the presence of covalent chemical or physical (e.g., ionic, hydrophobic interactions, entanglements, etc.) crosslinks. The crosslinks provide the network structure and physical integrity. Hydrogels exhibit a thermodynamic compatibility with water that allows them to swell in aqueous media. The chains of the network are connected in such a fashion that pores exist and that a substantial fraction of these pores are of dimensions between 1 nm and 1000 nm.

The hydrogels can be prepared by crosslinking hydrophilic biopolymers or synthetic polymers. Examples of the hydrogels formed from physical or chemical crosslinking of hydrophilic biopolymers, include but are not limited to, hyaluronans, chitosans, alginates, collagen, dextran, pectin, carrageenan, polylysine, gelatin, agarose, (meth)acrylate-oligolactide-PEO-oligolactide-(meth)acrylate, poly(ethylene glycol) (PEO), poly(propylene glycol) (PPO), PEO-PPO-PEO copolymers (Pluronics), poly(phosphazene), poly (methacrylates), poly(N-vinylpyrrolidone), PL(G)A-PEO-PL(G)A copolymers, poly(ethylene imine), and the like. See Hennink and van Nostrum, Adv. Drug Del. Rev. 54:13-36 (2002); Hoffman, Adv. Drug Del. Rev. 43:3-12 (2002); Cadee et al., J Control. Release 78:1-13 (2002); Surini et al., J. Control. Release 90:291-301 (2003); and U.S. Pat. No. 7,968,085, each of which is incorporated by reference in its entirety. These materials consist of high-molecular weight backbone chains made of linear or branched polysaccharides or polypeptides.

The amount of the pharmaceutical composition of the disclosure that will be effective in the treatment or prevention of a respiratory infection or allergy may depend on the nature of the pathogen and can be determined by standard clinical techniques, including blood tests and/or imaging techniques. In addition, in vitro assays may optionally be employed to help identify optimal dosage ranges. The precise dose to be employed in the formulation may also depend on the route of administration, and the seriousness of the infection, and should be decided according to the judgment of the practitioner and each patient's circumstances. Effective doses may be extrapolated from dose-response curves derived from in vitro or animal model test systems.

Dosages and Administration Regimens

The therapeutic agents, immunotherapeutic agents, or compositions containing these agents are administered in a manner compatible with the dosage formulation, and in such amount as may be therapeutically affective, protective and immunogenic.

The agents and/or compositions may be administered through different routes, including, but not limited to, nasal, aerosol, topical, buccal and sublingual, oral, intradermal, subcutaneous, and parenteral. The term parenteral as used herein includes, for example, intraocular, subcutaneous, intraperitoneal, intracutaneous, intravenous, intramuscular, intraarticular, intraarterial, intrasynovial, intrastemal, intrathecal, intralesional, and intracranial injection, or other infusion techniques.

In some embodiments, administration of the therapeutic agents is delivered locally or regionally (e.g., intranasally, etc.). In some embodiments, a device is used to deliver the antimicrobial composition to the respiratory tract. The composition may be delivered through use of an inhaler, atomizer, nebulizer, nasal spray bottle, nasal spray pump, ventilator, compressed air tank, aerosolizer, and nasal cannula. The composition can be delivered through insufflation, inhalation, oral ingestion, sublingual, and any combination thereof.

In embodiments, the agents and/or compositions formulated according to the present disclosure are formulated and delivered in a manner to evoke a systemic immune response. Thus, in some embodiments, the formulations are prepared by uniformly and intimately bringing into association the active ingredient with liquid carriers. Formulations suitable for administration include aqueous and non-aqueous sterile solutions, which may contain anti-oxidants, buffers, bacteriostats and solutes which render the formulation isotonic with the blood of the intended recipient, and aqueous and non-aqueous sterile suspensions which may include suspending agents and thickening agents. The formulations may be presented in unit-dose or multi-dose containers, for example, sealed ampoules and vials, and may be stored in a freeze-dried (lyophilized) condition requiring only the addition of the sterile liquid carrier, for example, water, immediately prior to use. Extemporaneous solutions and suspensions may be prepared from sterile powders, granules and tablets commonly used by one of ordinary skill in the art.

The agents and/or compositions may be administered in different forms, including, but not limited to, gases, solutions, emulsions and suspensions, gels, foams, sprays, mists, lotions, microspheres, particles, microparticles, nanoparticles, liposomes, and the like.

The agents and/or compositions are administered in a manner compatible with the dosage formulation, and in such amount as may be therapeutically effective, immunogenic and protective. The quantity to be administered depends on the subject to be treated, including, for example, the size of the infection and the capacity of the individual's immune system to synthesize antibodies and/or to produce a cell-mediated immune response. Precise amounts of active ingredients required to be administered depend on the judgment of the practitioner. However, suitable dosage ranges are readily determinable by one skilled in the art and may be of the order of micrograms to milligrams of the active ingredient(s) per dose. The dosage may also depend on the route of administration and may vary according to the size of the host.

The agents and/or compositions should be administered to a subject in an amount effective to stimulate a protective immune response in the subject. Specific dosage and treatment regimens for any particular subject may depend upon a variety of factors, including the activity of the specific compound employed, the age, body weight, general health status, sex, diet, time of administration, rate of excretion, drug combination, the severity and course of the infection, condition or symptoms, the subject's disposition to the disease, condition or symptoms, method of administration, and the judgment of the treating physician. Actual dosages can be readily determined by one of ordinary skill in the art.

Exemplary unit dosage formulations are those containing a dose or unit, or an appropriate fraction thereof, of the administered ingredient. It should be understood that in addition to the ingredients mentioned herein, the formulations of the present disclosure may include other agents commonly used by one of ordinary skill in the art.

At present the oral or nasal spray or aerosol route (e.g., by inhalation) is most commonly used to deliver therapeutic agents directly to the lungs and respiratory system. However, the invention encompasses the delivery of the inventive pharmaceutical composition by any appropriate route taking into consideration likely advances in the sciences of drug delivery.

In some embodiments, preparations for inhaled or aerosol delivery comprise a plurality of particles. In some embodiments, such preparations have a mean particle size of 4, 5, 6, 7, 8, 9, 10, 11, 12, or 13 microns. In some embodiments, preparations for inhaled or aerosol delivery are formulated as a dry powder. In some embodiments, preparations for inhaled or aerosol delivery are formulated as a wet powder, for example through inclusion of a wetting agent. in some embodiments, the wetting agent is selected from the group consisting of water, saline, or other liquid of physiological pH.

In some embodiments, inventive compositions are administered as drops to the nasal or buccal cavity. In some embodiments, a dose may comprise a plurality of drops (e.g., 1-100, 1-50, 1-20, 1-10, 1-5, etc.).

Typically in conventional systemically administered treatments, a therapeutically effective dosage should produce a serum concentration of compound of from about 0.1 ng/mL to about 50-100 μg/mL. The pharmaceutical compositions typically provide a dosage of from about 0.001 mg to about 2000 mg of compound per kilogram of body weight per day. For example, dosages for administration to a human patient can range from 1-10 μg/kg, 20-80 μg/kg, 5-50 μg/kg, 75-150 μg/kg, 100-500 μg/kg, 250-750 μg/kg, 500-1000 μg/kg, 1-10 mg/kg, 5-50 mg/kg, 25-75 mg/kg, 50-100 mg/kg, 100-250 mg/kg, 50-100 mg/kg, 250-500 mg/kg, 500-750 mg/kg, 750-1000 mg/kg, 1000-1500 mg/kg, 1500-2000 mg/kg, 5 mg/kg, 20 mg/kg, 50 mg/kg, 100 mg/kg, 500 mg/kg, 1000 mg/kg, 1500 mg/kg, or 2000 mg/kg. Pharmaceutical dosage unit forms are prepared to provide from about 1 mg to about 5000 mg, for example from about 100 to about 2500 mg of the compound or a combination of essential ingredients per dosage unit form.

In general, a therapeutically effective amount of the present compounds in dosage form usually ranges from slightly less than about 0.025 mg/kg/day to about 2.5 g/kg/day, preferably about 0.1 mg/kg/day to about 100 mg/kg/day of the patient or considerably more, depending upon the compound used, the condition or infection treated and the route of administration, although exceptions to this dosage range may be contemplated by the present disclosure. In an exemplary embodiment, antimicrobial/antiviral compositions according to the present disclosure may be administered intranasally in amounts ranging from about 0.5 mg/mL of dosing solution to about 50 mg/mL. In another exemplary embodiment, antimicrobial compositions according to the present disclosure may be administered intranasally in amounts ranging from about 10 mg/mL to about 30 mg/mL. The dosage of the antimicrobial composition(s) may depend on the type of infection being treated, the particular compound used, the therapeutic agent, and other clinical factors and conditions of the patient. It is to be understood that the present disclosure has application for both human and veterinary use.

The agents and/or compositions may be administered in one or more doses as required to achieve the desired effect. Thus, the agents and/or compositions may be administered in 1, 2, to 3, 4, 5, or more doses. Further, the doses may be separated by any period of time, for example hours, days, weeks, months, and years.

The agents and/or compositions may be formulated as liquids or dry powders, or in the form of microspheres.

The agents and/or compositions may be stored at temperatures of from about −100° C. to about 25° C. depending on the duration of storage. The agents and/or compositions may also be stored in a lyophilized state at different temperatures including room temperature. The agents and/or compositions may be sterilized through conventional means known to one of ordinary skill in the art. Such means include, but are not limited to, filtration.

The amount of active ingredient that may be combined with carrier materials to produce a single dosage form may vary depending upon the host treated and the particular mode of administration. In embodiments, a preparation may contain from about 0.1% to about 95% active compound (w/w), from about 20% to about 80% active compound, or from any percentage there between.

In embodiments, the pH of the formulation may be adjusted with pharmaceutically acceptable acids, bases, or buffers to enhance the stability of the formulated compound or its delivery form.

In embodiments, the pharmaceutical carriers may be in the form of a sterile liquid preparation, for example, as a sterile aqueous or oleaginous suspension.

Among the acceptable vehicles and solvents that may be employed are mannitol, water, Ringer's solution and isotonic sodium chloride solution.

In addition, sterile, fixed oils are conventionally employed as a solvent or suspending medium. For this purpose, any bland fixed oil may be employed including synthetic mono- or to diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions.

Other commonly used surfactants such as TWEEN® or SPAN® and/or other similar emulsifying agents or bioavailability enhancers which are commonly used in the manufacture of pharmaceutically acceptable solid, liquid, or other dosage forms may also be used for the purposes of formulation.

In embodiments, the agents and/or compositions can be delivered in an exosomal delivery system. Exosomes are small membrane vesicles that are released into the extracellular environment during fusion of multivesicular bodies with plasma membrane. Exosomes are secreted by various cell types including hematopoietic cells, normal epithelial cells and even some tumor cells. Exosomes are known to carry MHC class I, various costimulatory molecules and some tetraspanins. Recent studies have shown the potential of using native exosomes as immunologic stimulants.

Also contemplated by the disclosure is delivery of the agents and/or compositions using nanoparticles. For example, the agents and/or compositions provided herein can contain nanoparticles having at least one or more agents linked thereto, e.g., linked to the surface of the nanoparticle. A composition typically includes many nanoparticles with each nanoparticle having at least one or more agents linked thereto. Nanoparticles can be colloidal metals. A colloidal metal includes any water-insoluble metal particle or metallic compound dispersed in liquid water. Typically, a colloid metal is a suspension of metal particles in aqueous solution. Any metal that can be made in colloidal form can be used, including gold, silver, copper, nickel, aluminum, zinc, calcium, platinum, palladium, and iron. In some cases, gold nanoparticles are used, e.g., prepared from $HAuCl_4$. Nanoparticles can be any shape and can range in size from about 1 nm to about 10 nm in size, e.g., about 2 nm to about 8 nm, about 4 to about 6 nm, or about 5 nm in size. Methods for making colloidal metal nanoparticles, including gold colloidal nanoparticles from $HAuCl_4$, are known to those having ordinary skill in the art. For example, the methods described herein as well as those described elsewhere (e.g., US Pat. Publication Nos. 2001/005581; 2003/0118657; and 2003/0053983, which are hereby incorporated by reference) are useful guidance to make nanoparticles.

In certain cases, a nanoparticle can have two, three, four, five, six, or more active agents linked to its surface. Typically, many molecules of active agents are linked to the surface of the nanoparticle at many locations. Accordingly, when a nanoparticle is described as having, for example, two active agents linked to it, the nanoparticle has two active agents, each having its own unique molecular structure, linked to its surface. In some cases, one molecule of an active agent can be linked to the nanoparticle via a single attachment site or via multiple attachment sites. An active agent can be linked directly or indirectly to a nanoparticle surface. For example, the active agent can be linked directly to the surface of a nanoparticle or indirectly through an intervening linker.

Any type of molecule can be used as a linker. For example, a linker can be an aliphatic chain including at least two carbon atoms (e.g., 3, 4, 5, 6, 7, 8, 9, 10 or more carbon atoms), and can be substituted with one or more functional groups including ketone, ether, ester, amide, alcohol, amine, urea, thiourea, sulfoxide, sulfone, sulfonamide, and disulfide to functionalities. In cases where the nanoparticle includes gold, a linker can be any thiol-containing molecule. Reaction of a thiol group with the gold results in a covalent sulfide (—S—) bond. Linker design and synthesis are well known in the art.

In embodiments, the nanoparticle is linked to a targeting agent/moiety. A targeting functionality can allow nanoparticles to accumulate at the target (e.g. nasal membrane) at higher concentrations than in other tissues. In general, a targeting molecule can be one member of a binding pair that exhibits affinity and specificity for a second member of a binding pair. For example, an antibody or antibody fragment therapeutic agent can target a nanoparticle to a particular region or molecule of the body (e.g., the region or molecule for which the antibody is specific) while also performing a therapeutic function. In some cases, a receptor or receptor fragment can target a nanoparticle to a particular region of the body, e.g., the location of its binding pair member. Other therapeutic agents such as small molecules can similarly target a nanoparticle to a receptor, protein, or other binding site having affinity for the therapeutic agent.

When the compositions of this disclosure comprise one or more additional therapeutic or prophylactic agents, the therapeutic/enhancing/immunotherapy agent and the additional agent should be present at dosage levels of between about 0.1 to 100%, or between about 5 to 95% of the dosage normally administered in a monotherapy regimen. The additional agents may be administered separately, as part of a multiple dose regimen, from the agents of this disclosure. Alternatively, those additional agents may be part of a single dosage form, mixed together with the agents of this disclosure in a single composition.

The administration of the agents and/or compositions of the disclosure elicits an immune response against a pathogen. Typically, the dose can be adjusted within this range based on, e.g., the subject's age, the subject's health and physical condition, the capacity of the subject's immune system to produce an immune response, the subject's body weight, the subject's sex, diet, time of administration, the degree of protection desired, and other clinical factors. Those in the art can also readily address parameters such as biological half-life, bioavailability, route of administration, and toxicity when formulating the agents and/or compositions of the disclosure.

The following examples further demonstrate several embodiments of this disclosure. While the examples illustrate the disclosure, they are not intended to limit it.

EXAMPLES

The structures, materials, compositions, and methods described herein are intended to be representative examples of the disclosure, and it will be understood that the scope of the disclosure is not limited by the scope of the examples. Those skilled in the art will recognize that the disclosure may be practiced with variations on the disclosed structures, materials, compositions and methods, and such variations are regarded as within the ambit of the disclosure.

Example 1: Administration of Antimicrobial Compositions in Non-Human Subjects to Prevent Infection Varying concentrations of antimicrobial compositions containing ingredients from Table 1 are administered intranasally to a group of healthy, uninfected mice selected for age, gender and weight. After a suitable period of time to allow the compositions to take effect, mice are inoculated nasally with varying doses of respiratory pathogens (influenza, rhinovirus, bacteria, and fungi). At different subsequent time points, samples are extracted from the mice and analyzed for microbial infection. Lack of infection indicates the antimicrobial composition prevents the airborne pathogens from infecting the mice. The antimicrobial composition enhances the filtering capabilities of the nasal membrane and protects against the airborne pathogens.

Example 2: Administration of Antimicrobial Compositions in Non-Human Subjects to Treat Infection A group of healthy, uninfected mice selected for age, gender and weight are inoculated nasally with varying doses of respiratory pathogens (influenza, rhinovirus, bacteria, and fungi). After allowing suitable time for the pathogens to infect the mice, varying concentrations of antimicrobial compositions containing ingredients from Table 1 (as in Example 1) are administered intranasally to the infected mice. After a suitable period of time to allow the compositions to take effect, samples are extracted from the mice and analyzed for microbial infection. Lack of infection indicates the antimicrobial composition treats the respiratory infections within the mice. The antimicrobial composition enhances the filtering capabilities of the nasal membrane and treats the infection caused by airborne pathogens.

Example 3: Administration of Antimicrobial Compositions in Human Subjects to Treat Infection A group of human subjects presenting without pre-existing influenza or rhinoviral infections are selected for treatment and their baseline blood drawn to screen for markers of respiratory infection. Antimicrobial compositions containing ingredients from Table 1 (as in Examples 1 and 2) are administered intranasally to the subjects. After a suitable period of time to allow the compositions to take effect, subjects are exposed to airborne rhinovirus or influenza. After a suitable period of time to determine whether they had been infected, their bloods would again be drawn and screened for systemic markers of respiratory infection and they would be observed and questioned for visible evidence of respiratory infection. Lack of infection indicates the antimicrobial composition prevents respiratory infections. The antimicrobial composition enhances the filtering capabilities of the nasal membrane and prevents the viruses from causing respiratory infection.

Example 4: Measurements of Compositions on Full Differentiated 3D Cell Model of the Human Airway Epithelia Inoculated with Rhinovirus A16

Various compositions were tested for their ability to protect a 3D model of human airway epithelium, constituted with primary human epithelial cells freshly isolated from nasal, tracheal or bronchial biopsies (MucilAir™). MucilAir™ is composed of basal cells, ciliated cells and mucus cells from the respiratory tract. The proportion of these various cell types is preserved compared to what one observes in vivo (Huang et al., Drug Discovery and Development-Present and Future, 8, 201). Moreover, the epithelia are started from de-differentiated cells. Epithelia (MucilAir™-Pool) were reconstituted with a mixture of cells isolated from 14 different normal nasal donors and cultured for 41 days. Epithelial cells were freshly isolated from biopsies (nose and bronchi), then seeded onto a semi-porous membrane (Costar Transwell, pore size 0.4 μm). After about 45 days of culture at air-liquid interface, the epithelia were fully differentiated, both morphologically and functionally. After 45 days of culture, the epithelia are fully ciliated, secreted mucus and are electrically tight (TEER>200 $\Omega cm^2$). The activity of the main epithelial ionic channels, such as CFTR, EnaC, Na/K ATPase, is preserved and the epithelia is shown to respond in a regulated and vectorial manner to the pro-inflammatory stimulus, TNF-α (Huang et al., 2011 and Huang et al., 3R-Info-Bulletin No. 41, October 2009).

Compositions with various active ingredients were prepared as shown in Table 5. Each composition was prepared in a buffered saline solution (0.9% NaCl, 1.25 mM $CaCl_2$, 10 mM HEPES). As used herein, "HRV1" refers to compositions comprising apolactoferrin (i.e., HRV1-1, HRV1-2, and HRV1-3) as the sole active, "HRV2" refers to compositions comprising lysozyme (i.e., HRV2-1, HRV2-2, and HRV2-3) as the sole active, and reference to "HRV3" refers to compositions comprising soluble ICAM-1 (sICAM) (i.e., HRV3-1, HRV3-2, and HRV2-3) as the sole active. Reference to "HRV4" refers to compositions comprising a combination of apolactoferrin, lysozyme and soluble ICAM-1.

TABLE 5

| Composition Name | Active Ingredients (Concentration) |
|---|---|
| HRV1-1 | Apolactoferrin (500 µg/mL) |
| HRV1-2 | Apolactoferrin (500 µg/mL) |
| HRV1-3 | Apolactoferrin (5 µg/mL) |
| HRV2-1 | Lysozyme (2500 µg/mL) |
| HRV2-2 | Lysozyme (250 µg/mL) |
| HRV2-3 | Lysozyme (25 µg/mL) |
| HRV3-1 | soluble ICAM-1 (50 µg/mL) |
| HRV3-2 | soluble ICAM-1 (5 µg/mL) |
| HRV3-3 | soluble ICAM-1 (0.5 µg/mL) |
| HRV4-1 | Apolactoferrin (500 µg/mL) |
|  | Lysozyme (2500 µg/mL) |
|  | soluble ICAM-1 (50 µg/mL) |
| HRV4-2 | Apolactoferrin (50 µg/mL) |
|  | Lysozyme (250 µg/mL) |
|  | soluble ICAM-1 (5 µg/mL) |
| HRV4-3 | Apolactoferrin (5 µg/mL) |
|  | Lysozyme (25 µg/mL) |
|  | soluble ICAM-1 (0.5 µg/mL) |

20 µL of each formulation was applied apically onto separate MucilAir™-Pools immediately prior to inoculation (time=0) with Human Rhinovirus-A16. 20 µL of the each of the formulations was also applied at 3.5 and 24 hours post-inoculation ("pi"). Innoculation with Human Rhinovirus-A16 was achieved by the application of 50 µL, of 2×10⁶/mL Human Rhinovirus A16 (clinical strain: QCHRV.16) on the apical side of the 3D model for 3 h at 34° C., 5% $CO_2$. The virus stocks were produced in MucilAir™ cultures and diluted in culture medium without purification or concentration.

After inoculation (time=0), epithelia were washed twice with MucilAir™ culture medium in order to clean the inoculum. Cell free, apical washes (20 minutes) with 200 µL MucilAir™ culture media were collected at 3.5 hours post-inoculation and then at 24 and 48 hours pi and stocked at −80° C.

From the apical washes, viral RNA was extracted with the QIAamp® Viral RNA kit (Qiagen). Viral RNA was quantified by quantitative RT-PCR (QuantiTect Probe RT-PCR, Qiagen) with the TaqMan ABI 7000. Using known concentration of the corresponding viral RNA to establish a standard curve, the quantification was absolute. Data are presented as genome copy number/mL on the graphs illustrating the results of viral replication, unless otherwise indicated. Experiments and data with a "(+)" designation refer to experiments performed on inoculated media and experiments and data with a "(−)" designation refer to experiments performed on media not inoculated with virus. To compare two sets of data, Students unpaired t-test was used. To compare means of three or more samples, One-way analysis of variance (ANOVA) was performed with Dunnett's multiple comparison tests (*=p<0.001, =p<0.01, *=p <0.05). As negative control, non-infected and non-treated cultures (Mock) were used.

To compare the potential effects of HRV compounds, positive controls were included. For the toxic effect, cultures were treated with 20 µL of 10% Triton X-100 in a buffered saline solution (0.9% NaCl, 1.25 mM $CaCl_2$), 10 mM HEPES). For the anti-Rhinovirus effect, 20 µL of 5 µM Rupintrivir was added to basal medium. Rupintrivir (Santa Cruz Biotechnologies) stock solution of 2 mM in DMSO (−20° C.) was diluted to 5 µM in MucilAir™ medium (0.25% DMSO final concentration).

Error bars in any FIG. refer to Standard Error of the Mean (SEM). All comparisons are versus the data from vehicle infected (without active) and all data reported are single measurement on three separate inserts (n=3). All reported results are statistically significant.

TEER Measurements

Tissue integrity was monitored using transepithelial electrical resistance ("TEER") measurements. TEER is a dynamic parameter that reflects the state of epithelia that can be affected by several factors. For example, if holes were present or if cellular junction were broken, the TEER values would be generally below 100 $\Omega cm^2$. In contrast, when epithelia are not damaged, the TEER values are typically above 200 $\Omega cm^2$. A notable decrease of the TEER values (but >100 $\Omega cm^2$) generally reflects an activation of the ion channels. A drastic increase of the TEER value reflects a blockage of the ion channel activity or a destruction of the ciliated cells. When an epithelium is damaged, a decrease of TEER would be associated with an increase of LDH release or a decrease of the cell viability. TEER monitoring was performed 24 (D1) and 48 (D2) hours post-inoculation. The Triton X-100 control corresponds to a loss of TEER (<100 $\Omega cm^2$) after cell damage. After addition of 200 µL of MucilAir™ medium to the apical compartment of the MucilAir™ cultures, resistance was measured with an EVOMX volt-ohm-meter (World Precision Instruments UK, Stevenage) for each condition. Measured resistance values (S2) were converted to TEER ($\Omega.cm^2$) with the membrane resistance (100Ω) connected in series to the epithelium. The epithelium has a total surface area of 0.33 cm². TEER may be calculated by the following formula:

$$TEER(\Omega cm^2)=(resistance\ value(\Omega)-100(\Omega))\times 0.33\ (cm^2)$$

The results of TEER measurements are found in FIGS. 1-4. As can be seen, no significant change in TEER was observed at 24 (D1) hours pi or at 48 (D2) hours pi for any of the HRV tes formulations.

Lactate Dehydrogenase Release

Lactate dehydrogenase ("LDH") is a stable cytoplasmic enzyme that is rapidly released into the culture medium upon rupture of the plasma membrane. 100 µL basolateral medium collected at each time-point was incubated with the reaction mixture of the Cytotoxicity Detection KitPLUS, following manufacturer's instructions (Sigma, Roche, 11644793001). The amount of the released LDH was then quantified by measuring the absorbance of each sample at 490 nm with a microplate reader. To determine the percentage of cytotoxicity, the difference of experimental absorbance ($A_{exp}$) from a low control is compared to the difference between Absorbance values of the low ($A_{low}$) and high control ($A_{high}$), using the following equation:

$$Cytotoxicity(\%)=(A_{exp}-A_{low})/(A_{high}-A_{low})$$

A percentage below 5% reflects a physiological release of LDH in the medium. LDH measurements were taken at 24 and 48 hours pi. The results are shown in FIGS. 5-8. As can be seen, drug formulations do not increase LDH release in the 3D models.

Cilia Beating Frequency

Cilia beating frequency ("CBF") was measured by an experimental system consisting of three parts: a camera (Sony XCD V60 Firewire), a PCI card and a specific package of software. 256 images were captured at high frequency rate (125 fps) at room temperature and the cilia beating frequency was then calculated using Epithelix software. CBF values may be subject to fluctuations due to parameters such as temperature, mucus viscosity or liquid (such as a buffered saline solution) applied on the apical surface of the MucilAir™ 3D epithelial model. Therefore results are considered significant when a ratio >20% between the infected vehicle control and the drug composition was reached. FIGS. 9-12 illustrate the results of the cilia beating frequency measurements taken 24 and 48 hours pi. As can be seen, HRV treatments showed no significant effect on cilia beating frequency.

Mucociliary Clearance

Figure 13:
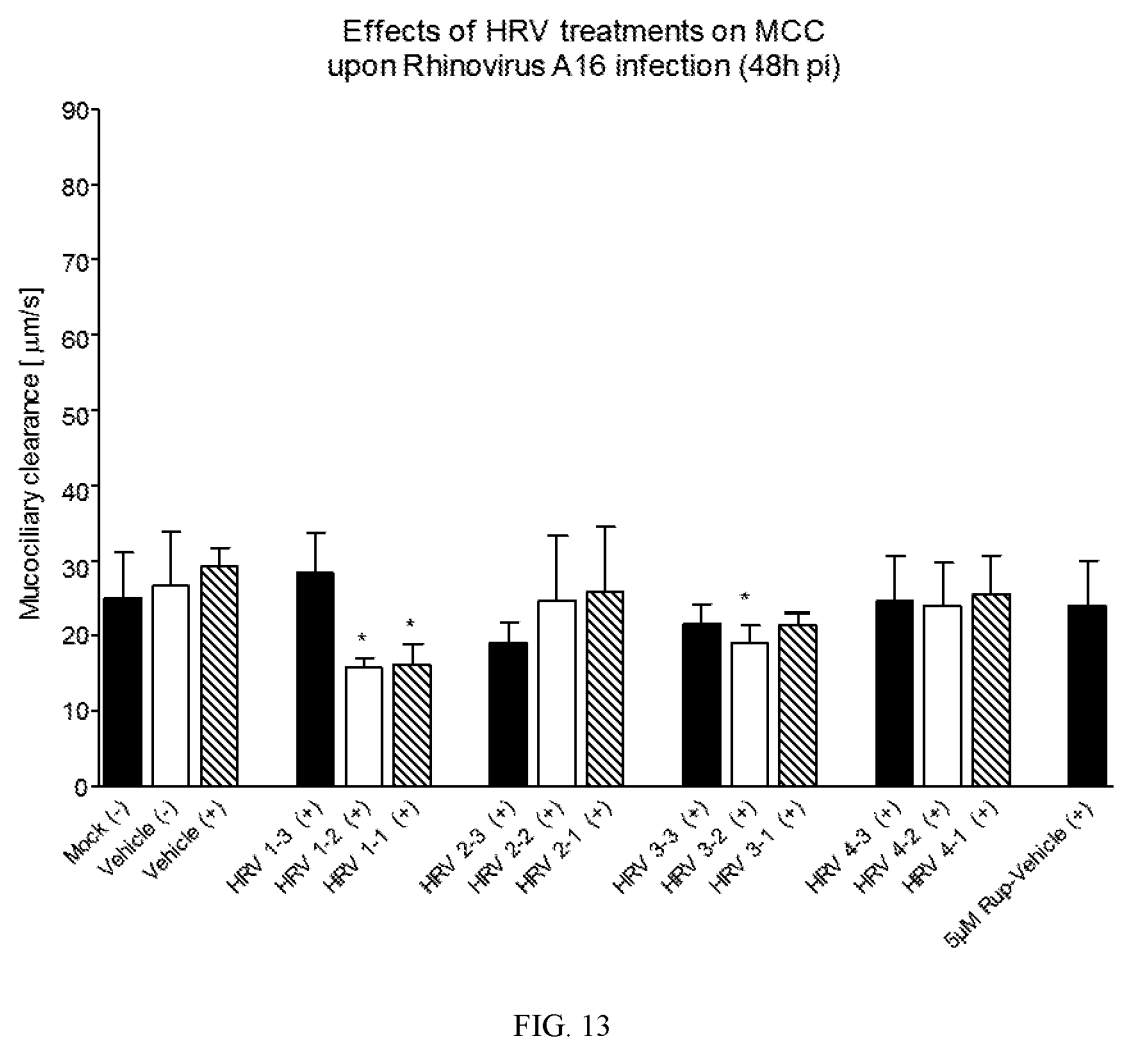

The mucociliary clearance ("MCC") was monitored using a Sony XCD-U100CR camera connected to an Olympus BX51 microscope with a 5× objective. Polystyrene microbeads of 30 μm diameter (Sigma, 84135) were added on the apical surface of MucilAir™. Microbead movements were video tracked at 2 frames per second for 30 images at room temperature. Three movies were taken per insert. Average beads movement velocity (Ωm/sec) was calculated with ImageProPlus 6.0 software. Mucociliary clearance values less than 10 μm/s are considered pathological. FIG. 13 illustrates the effect of Rhinovirus A16 infection on MCC on treatment with each of the actives alone and in combination measured 48 hours pi. As can be seen, combination treatment demonstrated superior and consistent response across the doses tested, as compared to the other test formulations. MCC was decreased for lower concentrations of HRV1 formulations and the HRV3-3 formulation. However, these negative effects were not seen with the HRV4 formulations at any concentration. Surprisingly, even though apolactoferrin alone inhibited ciliary movement at some doses (see, e.g., HRV1-1 and HRV1-2), the effect was completely ameliorated in the HRV combination at each dose.

Apical Rhinovirus Replication

From the 200 μL apical washes, 20 μL was used for viral RNA extraction with the QIAamp® Viral RNA kit (Qiagen) resulting in 60 μL RNA elution volume. Viral RNA was quantified by quantitative RT-PCR (QuantiTect Probe RT-PCR, Qiagen) using 5 μL of viral RNA, Mastermix, two Picornaviridae family specific and a Pan-Picornaviridae primers, and a Picornaviridae probe with FAM-TAMRA reporter-quencher dyes. Four dilutions of known concentration of Rhinovirus A16 as well as controls for RNA extraction and RT-PCR were included and the plates were run on a TaqMan ABI 7000 from Applied Biosystems. Count ("Ct") data were reported to the standard curve, corrected with the dilutions and presented as genome copy number/mL. FIGS. 14-16 and 17A, 17B, and 17C illustrate the results of Rhinovirus A16 replication. As can be seen Rhinovirus showed a significant replication which was inhibited by Rupintrivir. No significant change in Rhinovirus replication was achieved using HRV1 and HRV2 formulations. Application of HRV3 formulations results in a dose response relationship similar to that of Rupintrivir. HRV4 formulations show a dose dependent response on Rhinovirus A16 replication to a far greater degree than Rupintrivir treatment.

Enzyme-Linked Lectin Assay

Mucin secretion was quantified using an Enzyme-linked Lectin Assay ("ELLA") protocol detecting the carbohydrates groups of the collected mucus. 96-well plates were coated with 6 μg/mL Lectin from *Triticum vulgaris* (wheat) (Sigma, L0636) in phosphate buffered solution ("PBS") adjusted at pH 6.8 and incubated for 1 hour at 37° C. After washing steps with high salt phosphate buffered saline (PBS) (0.5 M NaCl, 0.1% Tween-20 in PBS), samples and standards (Mucin from porcine stomach Type II, Sigma, M2378) were incubated for 30 minutes at 37° C. After washing, plates were incubated 30 minutes at 37° C. with a detection solution containing 1 μg/mL of Peroxidase conjugated Lectin from *Glycine Max* (soybean) (Sigma, L2650), in 0.1% BSA-PBS adjusted at pH 7.4. After the final washing steps, a substrate reagent (TMB) was added and incubated for 10 minutes in the dark at room temperature. The reaction was stopped with 2N H2504 and the plates were read at 450 nm. FIGS. 18-21 illustrate the mucin quantity from the apical medium at 24 and 48 hours. As can be seen, the HRV test formulations showed no significant effect on mucin secretion.

Example 5: Measurements of Compositions on Full Differentiated 3D Cell Model of the Human Airway Epithelia Inoculated with Influenza a H1N1

Epithelia (MucilAir™-Pool) were reconstituted with a mixture of cells isolated from 14 different normal nasal donors and cultured for 41 days. Compositions with various active ingredients were prepared as shown in Table 6. Each composition was prepared in a buffered saline solution (0.9% NaCl, 1.25 mM $CaCl_2$), 10 mM HEPES). As used herein, "IAV1" refers to compositions comprising apolactoferrin (i.e., IAV1-1, IAV 1-2, and IAV 1-3), reference to "IAV2" refers to compositions comprising lysozyme (i.e., IAV 2-1, IAV 2-2, and IAV 2-3), and reference to "IAV3" refers to compositions comprising soluble ICAM-1 (i.e., IAV 3-1, IAV 3-2, and IAV 2-3). Reference to "IAV4" refers to example compositions comprising a combination of apolactoferrin, lysozyme, 3'-sialyllactose, and 6'-sialyllactose. These various test formulations are shown below in Table 6.

TABLE 6

| Composition Name | Active Ingredients (Concentration) |
|---|---|
| IAV1-1 | Apolactoferrin (500 μg/mL) |
| HRV1-2 | Apolactoferrin (50 μg/mL) |
| IAV1-3 | Apolactoferrin (5 μg/mL) |
| IAV2-1 | Lysozyme (2500 μg/mL) |
| IAV2-2 | Lysozyme (250 μg/mL) |
| IAV2-3 | Lysozyme (25 μg/mL) |
| IAV3-1 | 3'-sialyllactose (327 μg/mL)<br>6'-sialyllactose (327 μg/mL) |
| IAV3 -2 | 3'-sialyllactose (3.27 μg/mL)<br>6'-sialyllactose (3.27 μg/mL) |
| IAV3-3 | 3'-sialyllactose (0.327 μg/mL)<br>6'-sialyllactose (0.327 μg/mL) |
| IAV4-1 | Apolactoferrin (500 μg/mL)<br>Lysozyme (2500 μg/mL)<br>3'-sialyllactose (327 μg/mL)<br>6'-sialyllactose (327 μg/mL) |
| IAV4-2 | Apolactoferrin (50 μg/mL)<br>Lysozyme (250 μg/mL)<br>3'-sialyllactose (3.27 μg/mL)<br>6'-sialyllactose (3.27 μg/mL) |
| IAV4-3 | Apolactoferrin (5 μg/mL)<br>Lysozyme (25 μg/mL)<br>3'-sialyllactose (0.327 μg/mL)<br>6'-sialyllactose (0.327 μg/mL) |

20 μL of each formulation was applied apically onto separate MucilAir™-Pools immediately prior to inoculation with Influenza A H1N1. 20 μL of the each formulation was also applied at 3.5 and 24 hours post-inoculation. Innoculation with Influenza A H1N1 (t=0) was achieved by the application of 50 μL of 2×10⁶/mL H1N1 (clinical strain: A/California/7/09) on the apical side of MucilAir™ tissue for 3 h at 34° C., 5% $CO_2$. The virus stocks were produced in MucilAir™ cultures and diluted in culture medium without purification or concentration. Measurements on TEER, LDH release, CBF, MCC and mucin secretion were performed in an otherwise identical fashion as described above, except that 10 µM Oseltamivir was used instead of Ruptinivir for the antiviral effect formulation. For the antiviral effect, 10 µM Oseltamivir was added to basal medium. Oseltamivir acid (Carbosynth) stock solution of 4 mM in DMSO (–20° C.) was diluted to 10 µM in MucilAir™ basolateral medium (0.25% DMS final concentration).

TEER Measurements

FIGS. 22-25 illustrate the results of TEER measurements with Influenza A H1N1. As can be seen, the cytopathic effect of the influenza virus caused a decrease in the TEER resistance measurement. The IAV3 and IAV4 test formulations appear to limit the decrease in TEER at 48 hours (D2) pi, with the mitigation of resistance loss most pronounced in formulations comprising higher concentrations of actives (i.e., IAV4-2 and IAV4-1).

Lactate Dehydrogenase Release

FIGS. 26-29 illustrate the results of LDH release from the epithelial cells. As can be seen, no cytotoxic effect was observed for any of the IAV formulations.

Cilia Beating Frequency

FIGS. 30-33 illustrate the effects of the various treatments on the CBF of epithelial cells with Influenza H1N1 infection. As can be seen, IAV4 showed no significant effect on CBF.

Mucociliary Clearance

Figure 1:
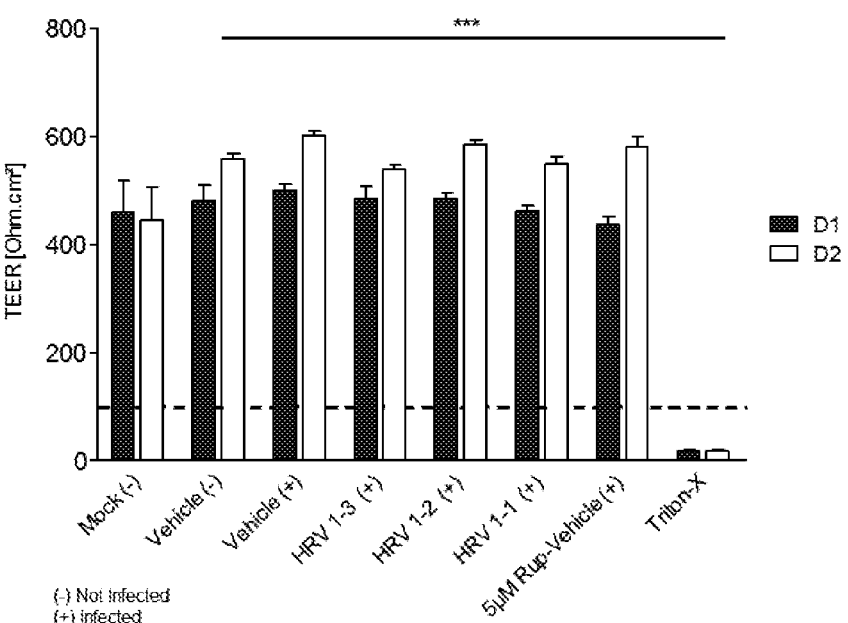
FIG. 1 illustrates the effect apolactoferrin treatment at 500 µg/mL (HRV1-1), 50 µg/mL (HRV1-2), and 5 µg/mL (HRV1-3) on the integrity of tissue infected with Rhinovirus A16. TEER was monitored 24 (D1) and 48 hours (D2) post-inoculation on MucilAir™ 3D media.
Figure 2:
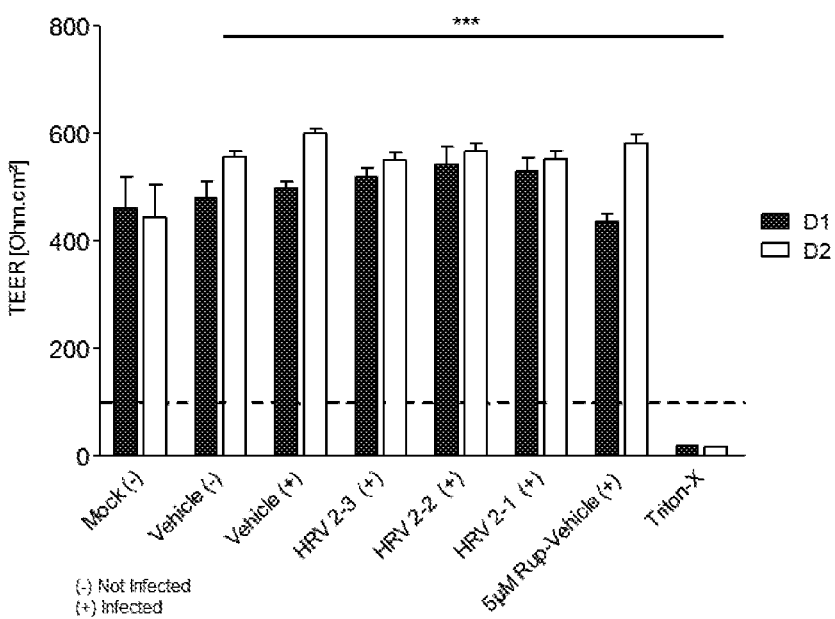
FIG. 2 illustrates the effect of lysozyme treatment at 2500 µg/mL (HRV2-1), 250 µg/mL (HRV2-2), and 25 µg/mL (HRV2-3) on the integrity of tissue infected with Rhinovirus A16. TEER was monitored 24 (D1) and 48 hours (D2) post-inoculation on MucilAir™ 3D media.
Figure 3:
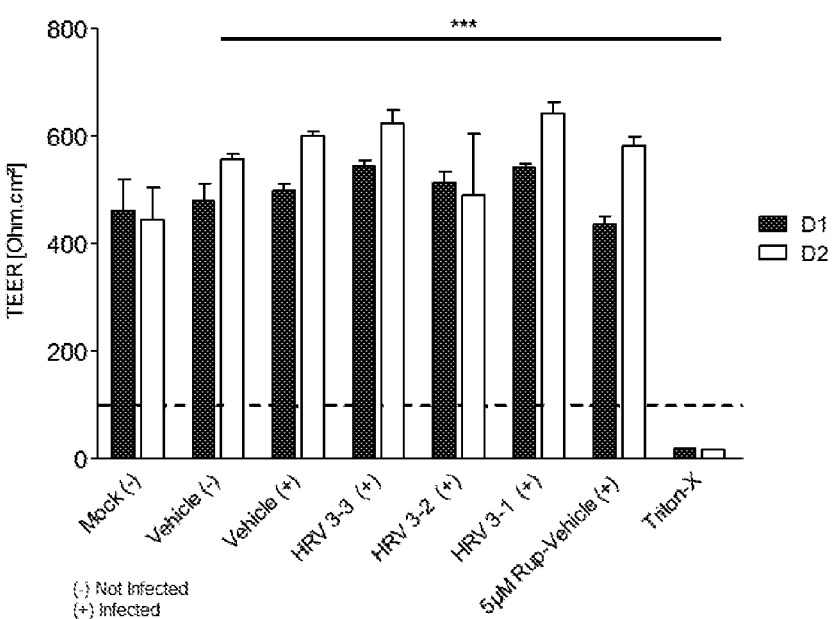
FIG. 3 illustrates the effect of soluble ICAM-1 treatment at 50 µg/mL (HRV3-1), 5 µg/mL (HRV3-2), and 0.5 µg/mL (HRV3-3) on the integrity of tissue infected with Rhinovirus A16. TEER was monitored 24 (D1) and 48 hours (D2) post-inoculation on MucilAir™ 3D media.
Figure 4:
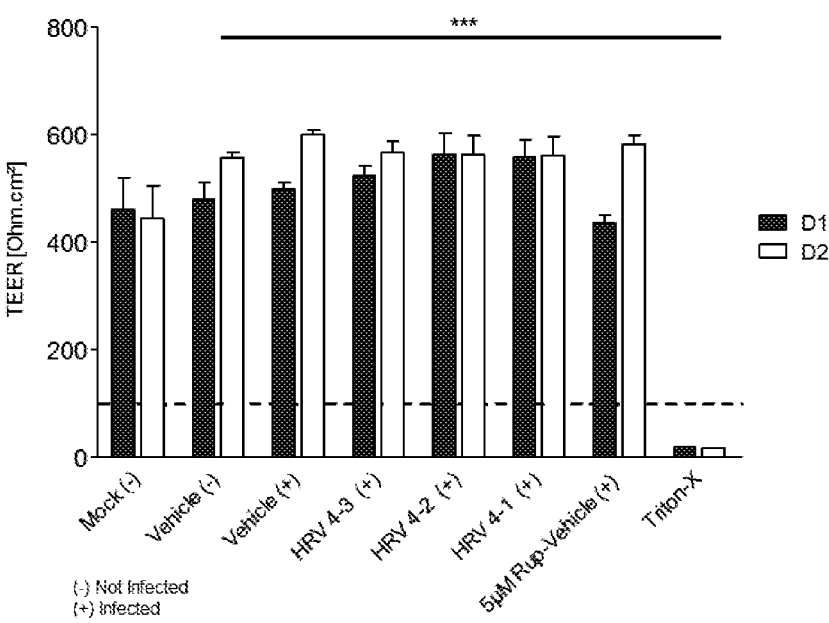
FIG. 4 illustrates the effect of treatment with a combination of apolactoferrin, lysozyme, and soluble ICAM-1 at the three different doses shown in Table 5 (HRV4-1, HRV4-2, and HRV4-3), on the integrity of tissue infected with Rhinovirus A16. TEER was monitored 24 (D1) and 48 hours (D2) post-inoculation on MucilAir™ 3D media.
Figure 5:
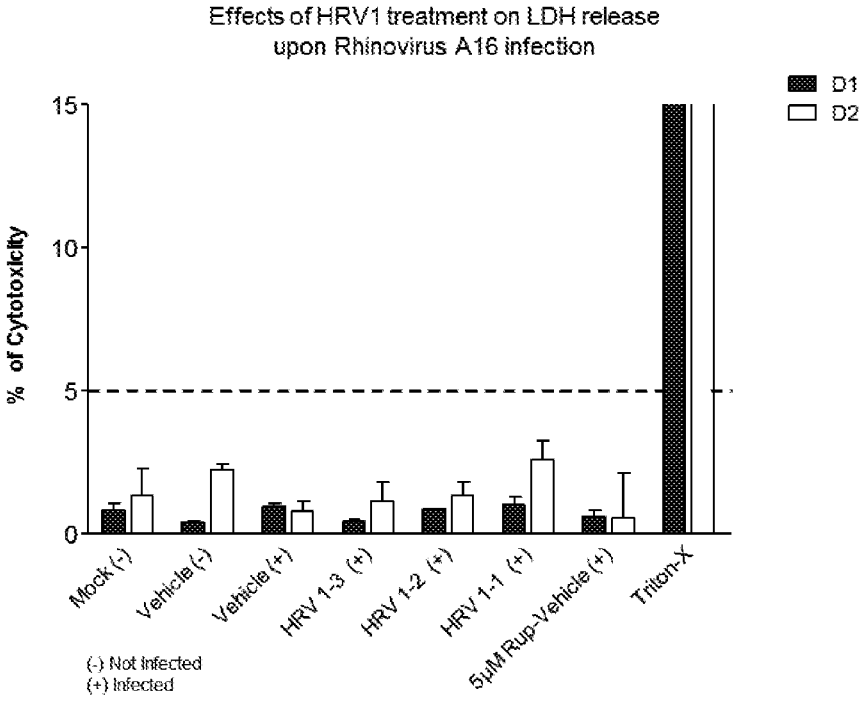
FIG. 5 illustrates the effect of apolactoferrin treatment at 500 µg/mL (HRV1-1), 50 µg/mL (HRV1-2), and 5 µg/mL (HRV1-3) on LDH release of cells infected with Rhinovirus A16. Cytotoxicity was monitored 24 (D1) and 48 (D2) hours post-inoculation on MucilAir™ 3D media.
Figure 6:
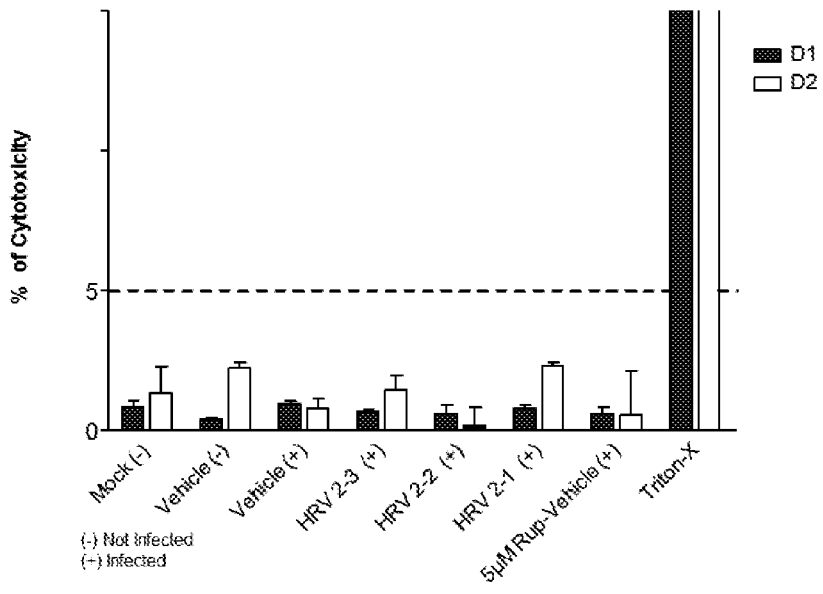
FIG. 6 illustrates the effect of lysozyme treatment at 2500 µg/mL (HRV2-1), 250 µg/mL (HRV2-2), and 25 µg/mL (HRV2-3) on LDH release of cells infected with Rhinovirus A16. Cytotoxicity was monitored 24 (D1) and 48 (D2) hours post-inoculation on MucilAir™ 3D media.
Figure 7:
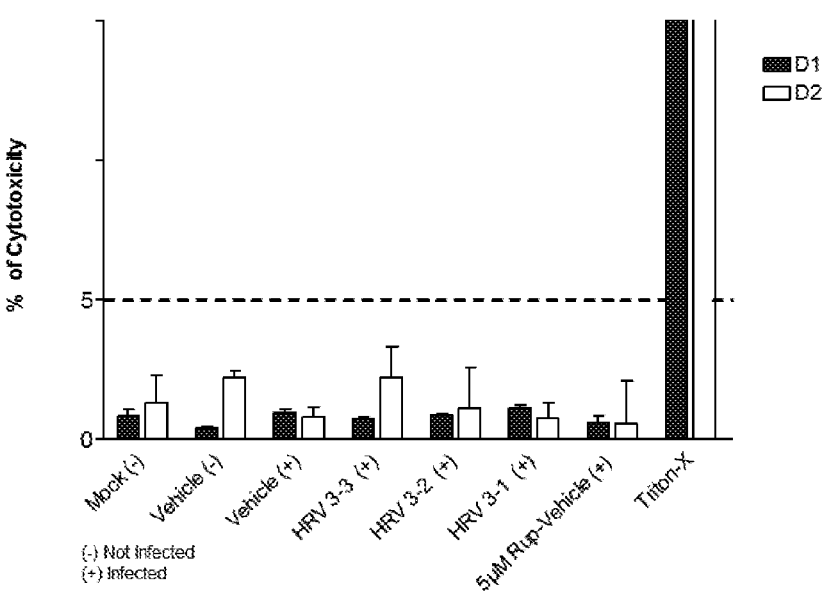
FIG. 7 illustrates the effect of soluble ICAM-1 treatment at 50 µg/mL (HRV3-1), 5 µg/mL (HRV3-2), and 0.5 µg/mL (HRV3-3) on LDH release of cells infected with Rhinovirus A16. Cytotoxicity was monitored 24 (D1) and 48 (D2) hours post-inoculation on MucilAir™ 3D media.
Figure 8:
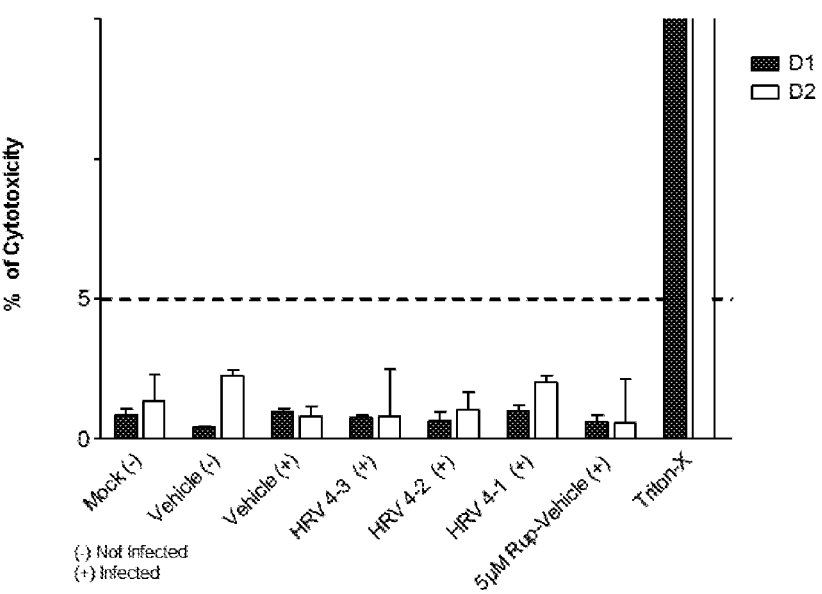
FIG. 8 illustrates the effect of a combination of apolactoferrin, lysozyme, and soluble ICAM-1 at the three different doses shown in Table 5 (HRV4-1, HRV4-2, and HRV4-3) on LDH release infected with Rhinovirus A16. Cytotoxicity was monitored 24 (D1) and 48 (D2) hours post-inoculation on MucilAir™ 3D media.
Figure 9:
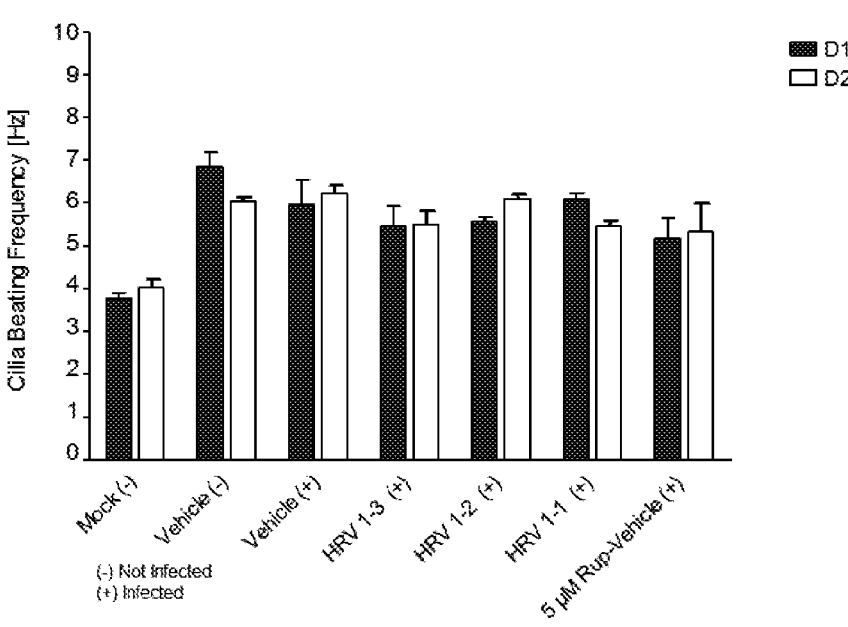
FIG. 9 illustrates the effect of apolactoferrin treatment at 500 µg/mL (HRV1-1), 50 µg/mL (HRV1-2), and 5 µg/mL (HRV1-3) on cilia beating. Cilia beating frequency was monitored 24 (D1) and 48 (D2) hours post-inoculation on MucilAir™ 3D media.
Figure 10:
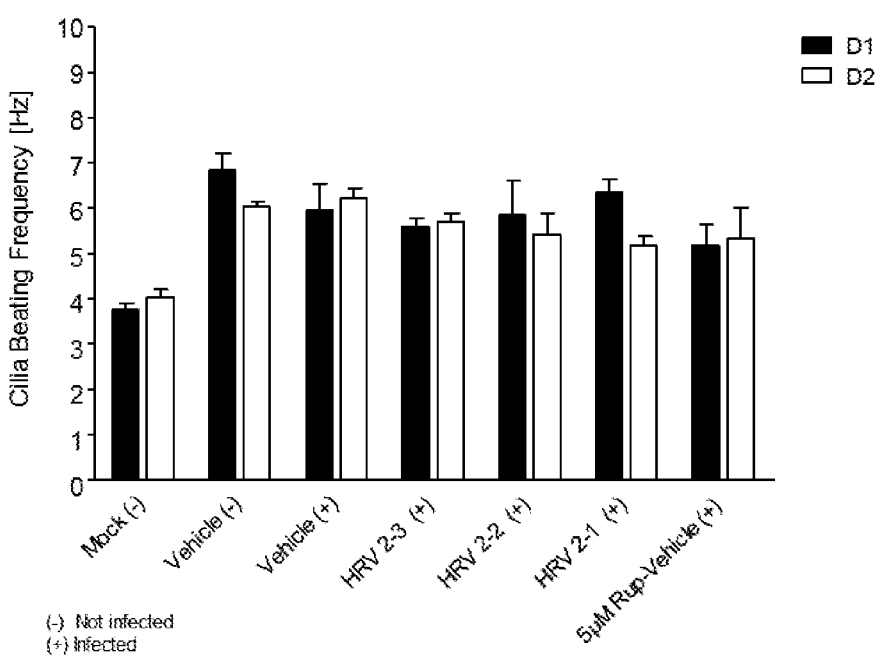
FIG. 10 illustrates the effect of Rhinovirus A16 infection on cilia beating frequency of epithelial cells with lysozyme treatment at 2500 µg/mL (HRV2-1), 250 µg/mL (HRV2-2), and 25 µg/mL (HRV2-3). Cilia beating frequency was monitored 24 (D1) and 48 (D2) hours post-inoculation on MucilAir™ 3D media.
Figure 11:
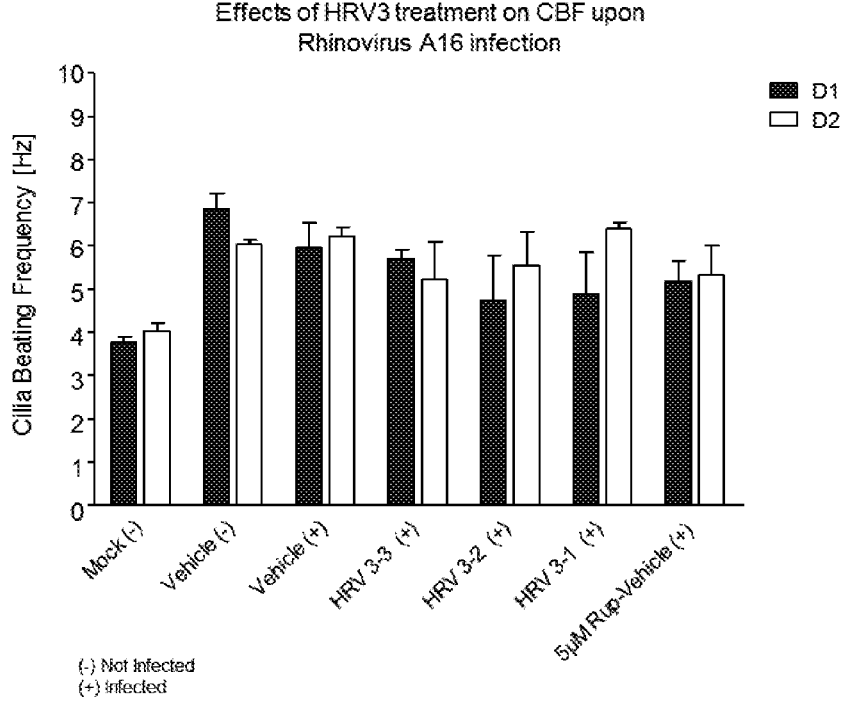
FIG. 11 illustrates the effect of Rhinovirus A16 infection on cilia beating frequency of epithelial cells with soluble ICAM-1 treatment at 50 µg/mL (HRV3-1), 5 µg/mL (HRV3-2), and 0.5 µg/mL (HRV3-3). Cilia beating frequency was monitored 24 (D1) and 48 (D2) hours post-inoculation on MucilAir™ 3D media.
Figure 12:
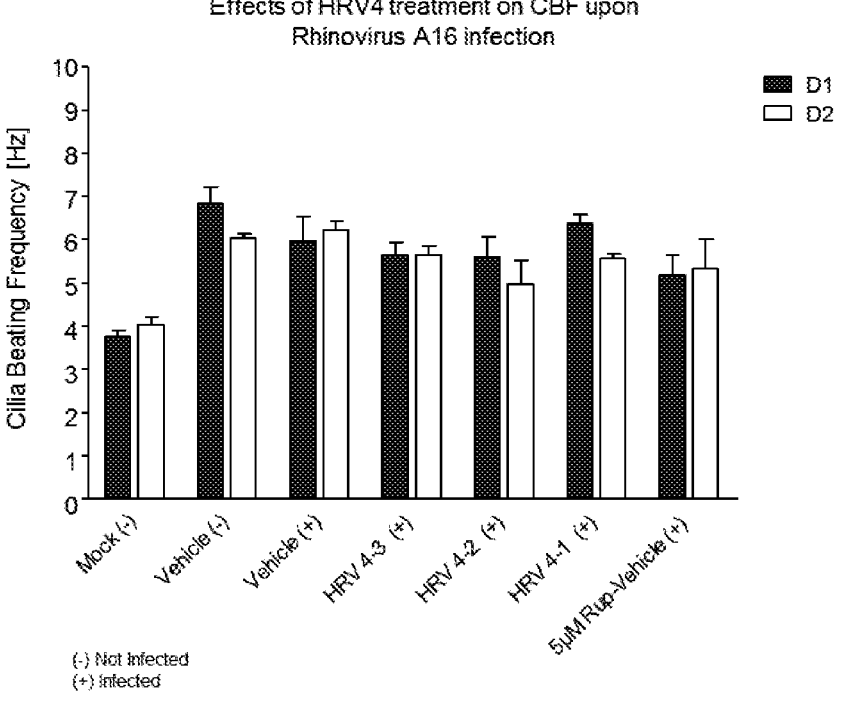
FIG. 12 illustrates the effect of Rhinovirus A16 infection on cilia beating frequency of epithelial cells with a combination of apolactoferrin, lysozyme, and soluble ICAM-1 at the three different doses shown in Table 5 (HRV4-1, HRV4-2, and HRV4-3). Cilia beating frequency was monitored 24 (D1) and 48 (D2) hours post-inoculation on MucilAir™ 3D media.
Figure 14:
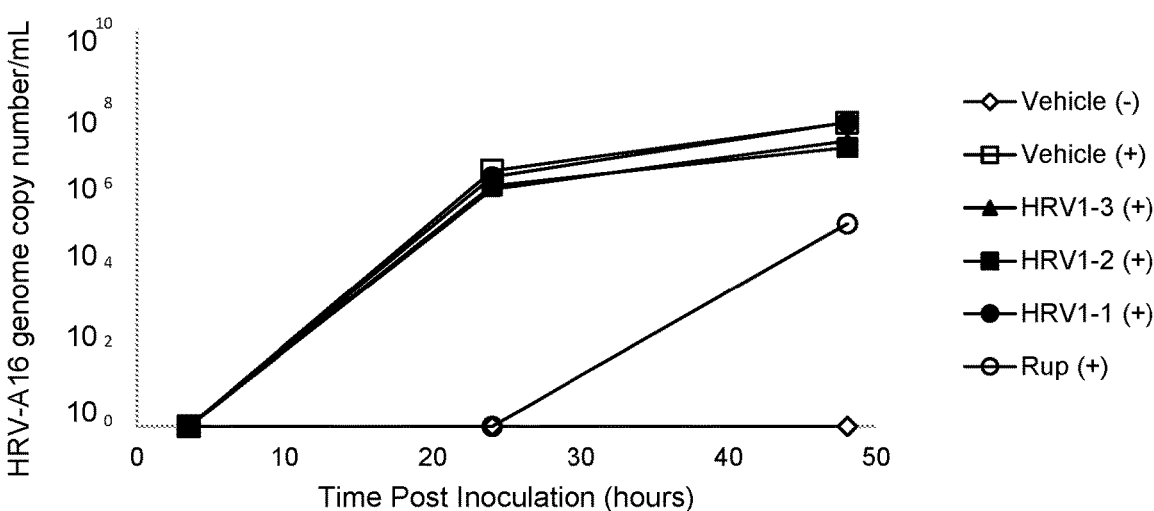
FIG. 14 illustrates the genome copy number of Rhinovirus A16 infection with apolactoferrin treatment at 500 µg/mL (HRV1-1), 50 µg/mL (HRV1-2), and 5 µg/mL (HRV1-3). Viral load was measured at 3.5, 24, and 48 hours post-inoculation on MucilAir™ 3D media.
Figure 15:
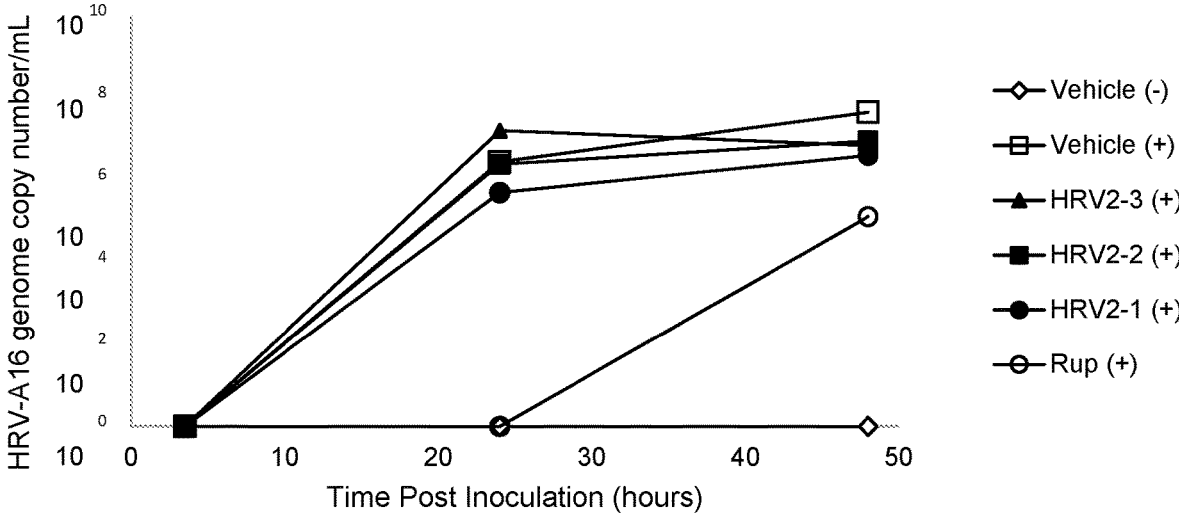
FIG. 15 illustrates the genome copy number of Rhinovirus A16 infection with lysozyme treatment at 2500 µg/mL (HRV2-1), 250 µg/mL (HRV2-2), and 25 µg/mL (HRV2-3). Viral load was measured at 3.5, 24, and 48 hours post-inoculation on MucilAir™ 3D media.
Figure 16:
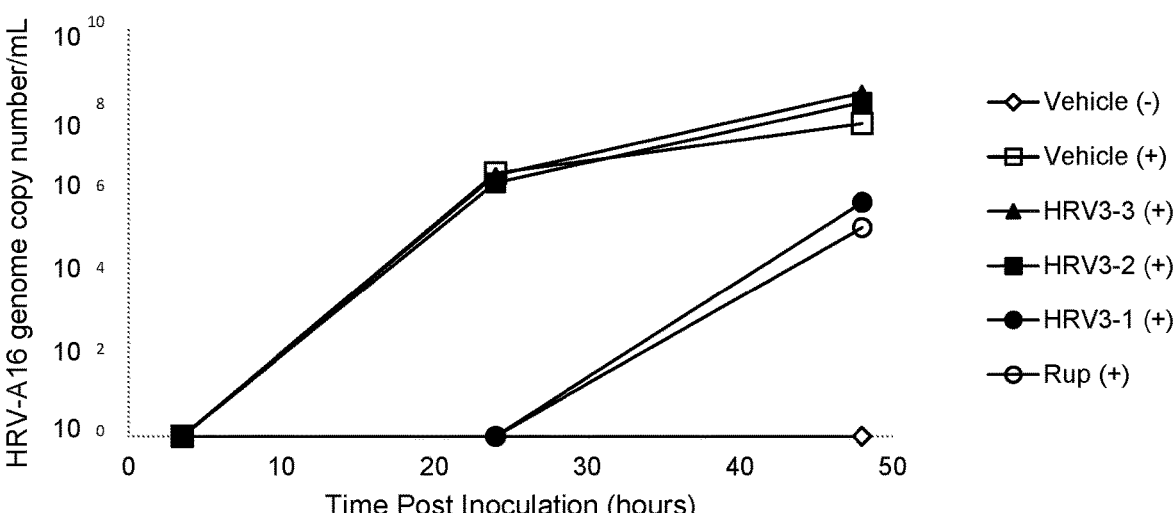
FIG. 16 illustrates the genome copy number of Rhinovirus A16 infection with soluble ICAM-1 treatment at 50 µg/mL (HRV3-1), 5 µg/mL (HRV3-2), and 0.5 µg/mL (HRV3-3). Viral load was measured at 3.5, 24, and 48 hours post-inoculation on MucilAir™ 3D media.
Figure 17A:
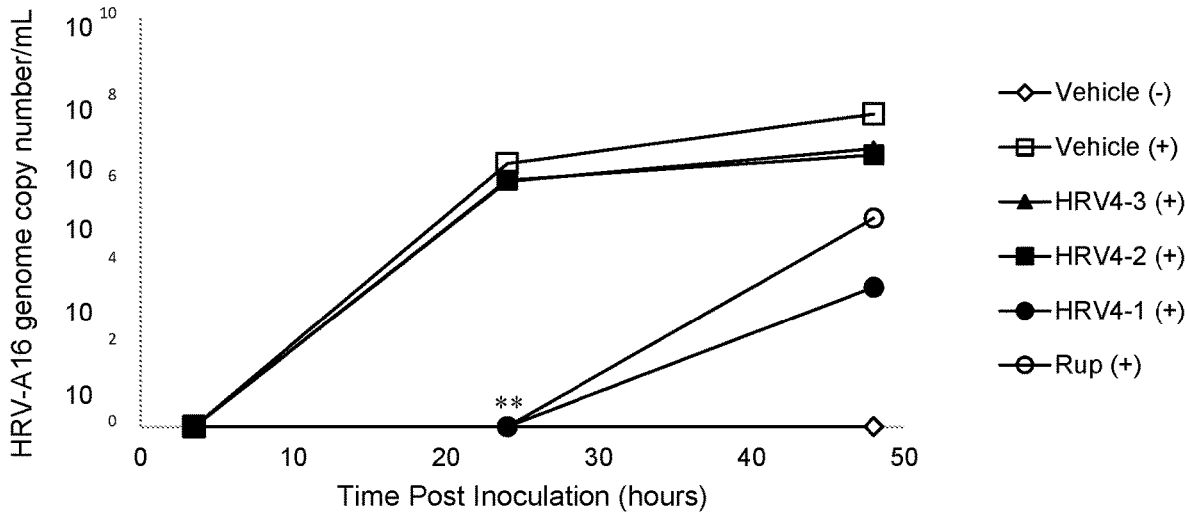
FIG. 17A illustrates the genome copy number of Rhinovirus A16 infection with a combination of apolactoferrin, lysozyme, and soluble ICAM-1 at the three different doses shown in Table 5 (HRV4-1, HRV4-2, and HRV4-3). Viral load was measured at 3.5, 24, and 48 hours post-inoculation on MucilAir™ 3D media.
Figure 17B:
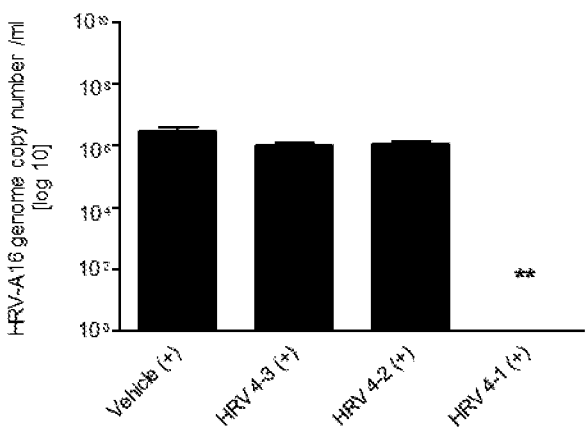
FIGS. 17B and 17C show the genome copy number ($Log_{10}$) of Rhinovirus A16 infection with HRV4 formulations comprising combinations of the actives as detailed in Table 5 at 24 hours pi and 48 hours pi, respectively. Statistical significance is measured with respect to control (Vehicle(+)): *:$p < 0.05$; :$p < 0.01$; *: $p < 0.001$.
Figure 17C:
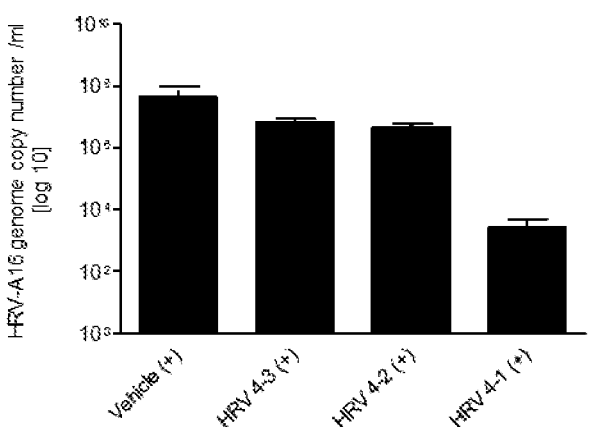
Figure 18:
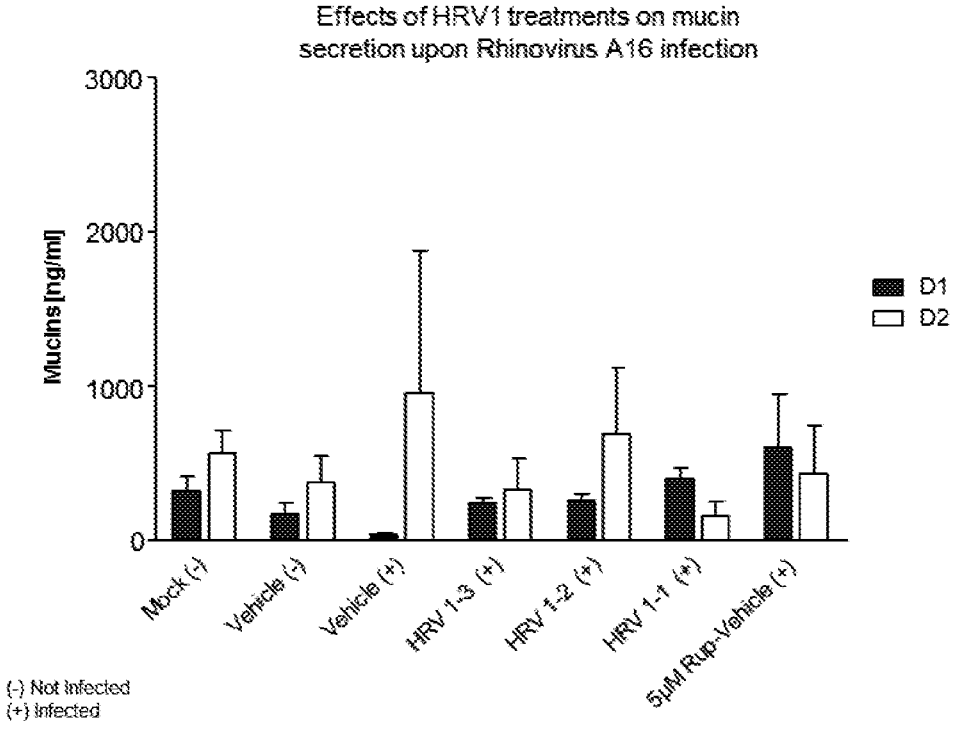
FIG. 18 illustrates the mucin quantity as measured with an ELLA assay from the apical medium with apolactoferrin treatment at 500 µg/mL (HRV1-1), 50 µg/mL (HRV1-2), and 5 µg/mL (HRV1-3) and Rhinovirus A16 infection at 24 (D1) and 48 hours (D2) post-inoculation on MucilAir™ 3D media.
Figure 19:
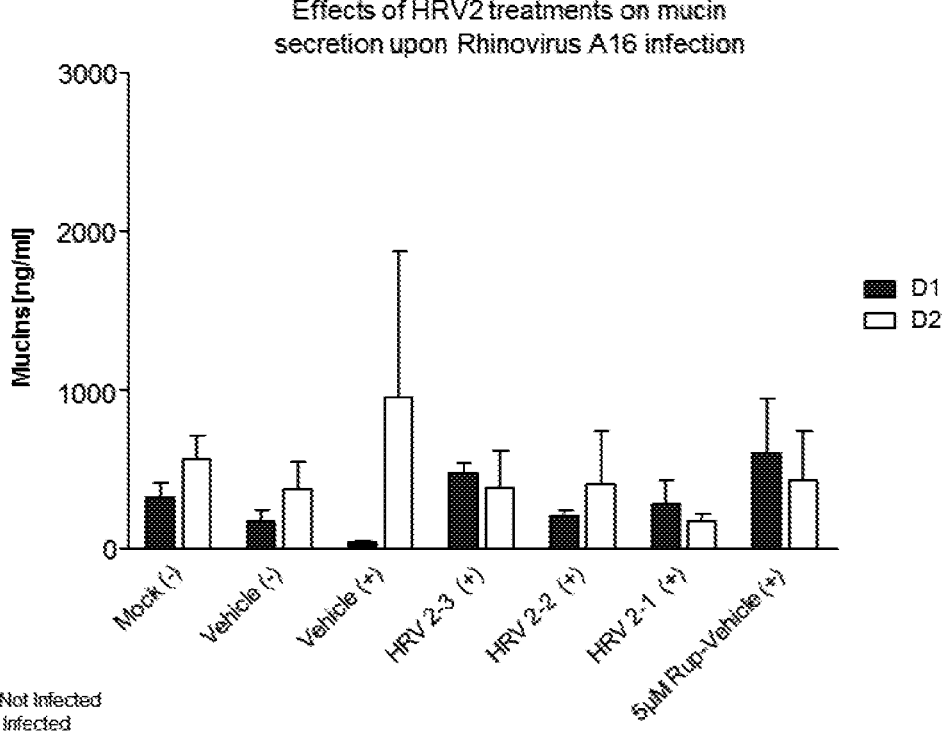
FIG. 19 illustrates the mucin quantity as measured with an ELLA assay from the apical medium with lysozyme treatment at 2500 μg/mL (IAV2-1), 250 μg/mL (HRV2-2), and 25 μg/mL (HRV2-3) and Rhinovirus A16 infection at 24 (D1) and 48 hours (D2) post-inoculation on MucilAir™ 3D media.
Figure 20:
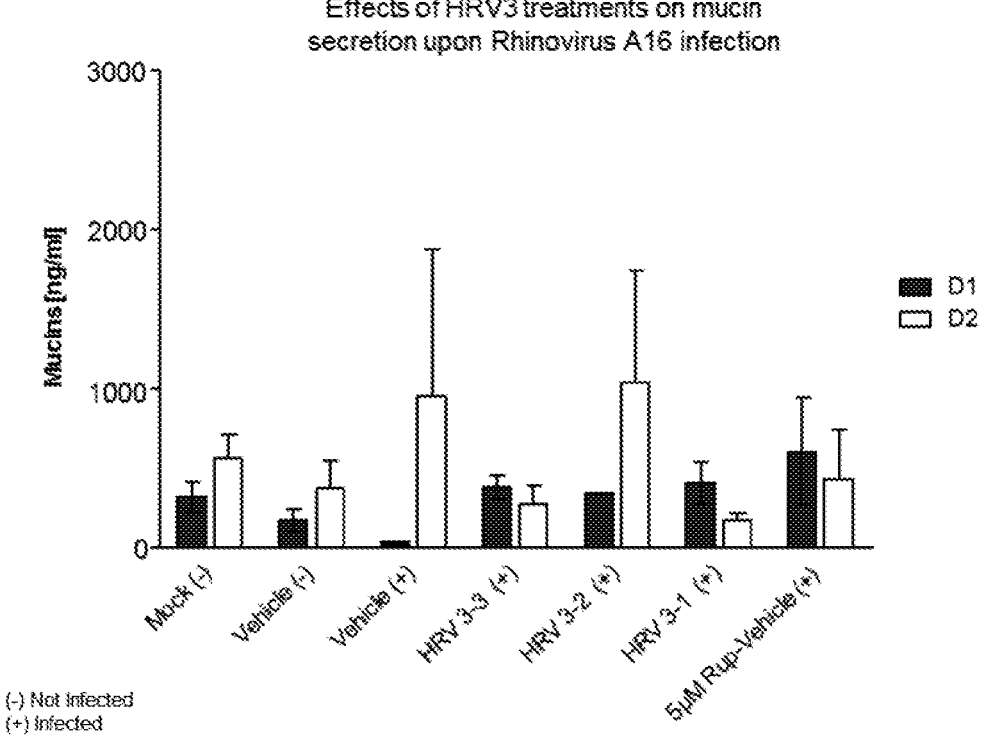
FIG. 20 illustrates the mucin quantity as measured with an ELLA assay from the apical medium with with soluble ICAM-1 treatment at 50 μg/mL (HRV3-1), 5 μg/mL (HRV3-2), and 0.5 μg/mL (HRV3-3) and Rhinovirus A16 infection at 24 (D1) and 48 hours (D2) post-inoculation on Muci-lAir™ 3D media.
Figure 21:
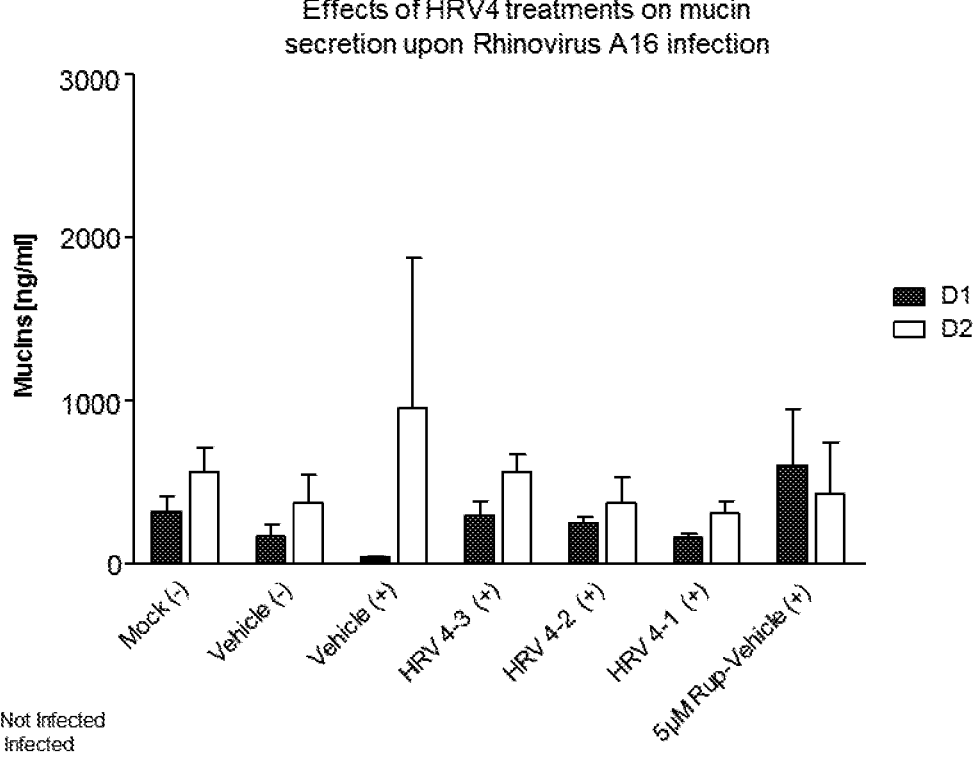
FIG. 21 illustrates the mucin quantity as measured with an ELLA assay from the apical medium with with apolactoferrin treatment at 500 μg/mL (HRV1-1), 50 μg/mL (HRV1-2), and 5 μg/mL (HRV1-3) and Rhinovirus A16 infection at 24 (D1) and 48 hours (D2) post-inoculation on MucilAir™ 3D media.
Figure 22:
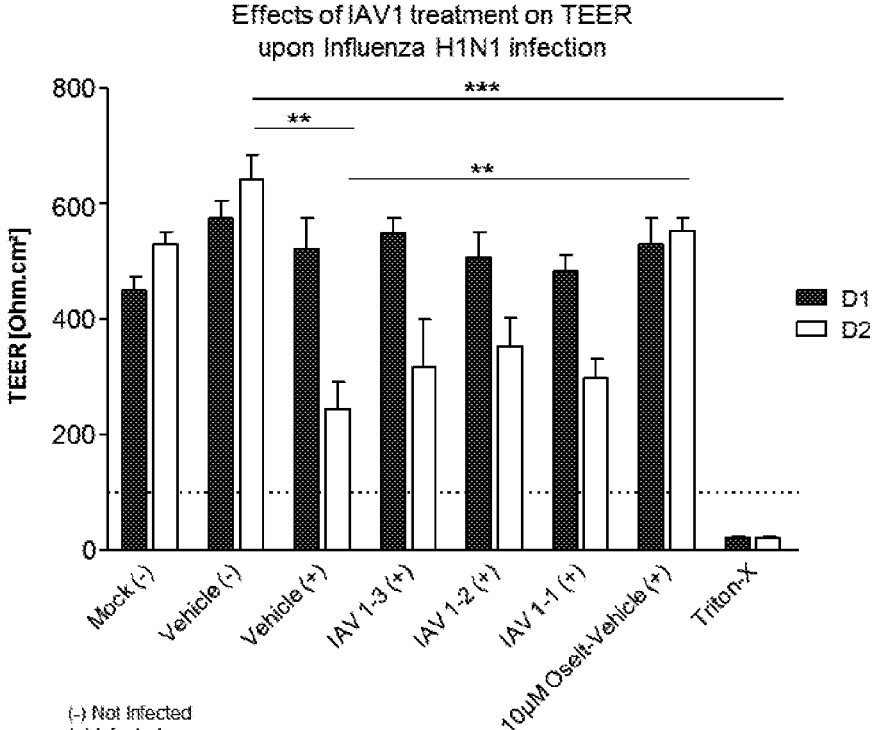
FIG. 22 illustrates the effect of Influenza A H1N1 infection on tissue integrity with apolactoferrin treatment at 500 μg/mL (IAV1-1), 50 μg/mL (IAV1-2), and 5 μg/mL (IAV1-3). TEER was monitored 24 (D1) and 48 hours (D2) post-inoculation on MucilAir™ 3D media.
Figure 23:
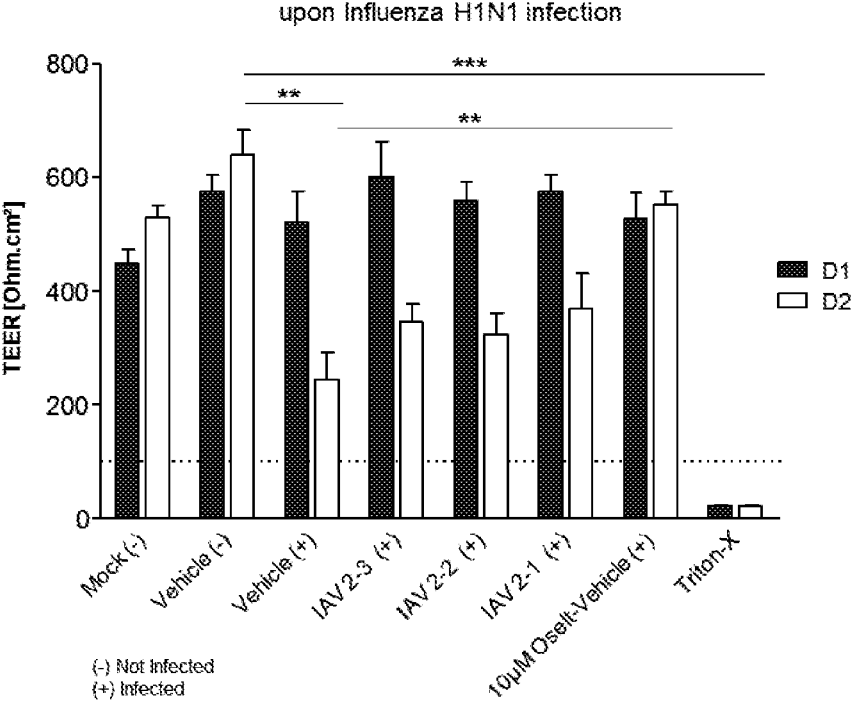
FIG. 23 illustrates the effect of Influenza A H1N1 infection on tissue integrity with lysozyme treatment at 2500 μg/mL (IAV2-1), 250 μg/mL (IAV2-2), and 25 μg/mL (IAV2-3). TEER was monitored 24 (D1) and 48 (D2) hours post-inoculation on MucilAir™ 3D media.
Figure 24:
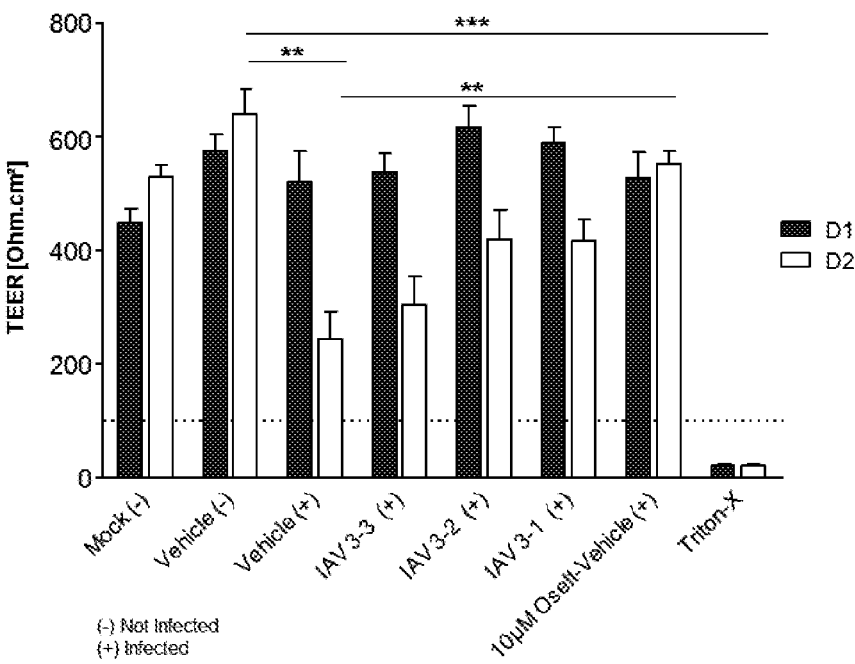
FIG. 24 illustrates the effect of Influenza A H1N1 infection on tissue integrity with a combination of 3'-sialyllactose and 6'sialyllactose treatment each at 327 μg/mL (IAV3-1), 3.27 μg/mL (IAV3-2), and 0.327 μg/mL (IAV3-3). TEER was monitored 24 (D1) and 48 (D2) hours post-inoculation on MucilAir™ 3D media.
Figure 25:
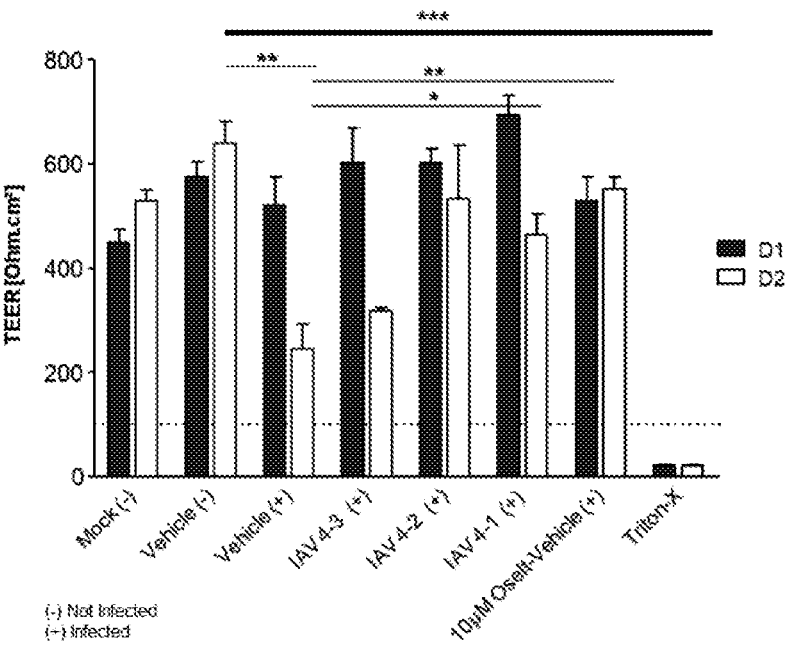
FIG. 25 illustrates the effect of Influenza A H1N1 infection on tissue integrity with a combination of apolactoferrin, lysozyme, and sialyllactoses at the three different doses shown in Table 5 (IAV4-1, IAV4-2, and IAV4-3). TEER was monitored 24 (D1) and 48 (D2) hours post-inoculation on MucilAir™ 3D media.
Figure 26:
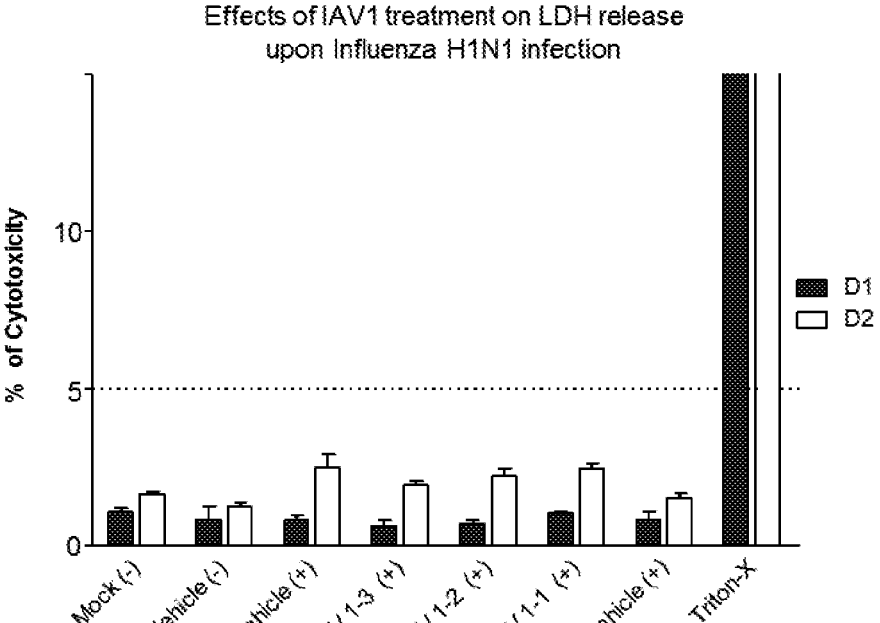
FIG. 26 illustrates the effect of Influenza A H1N1 infection on LDH release from epithelial cells apolactoferrin treatment at 500 μg/mL (IAV1-1), 50 μg/mL (IAV1-2), and 5 μg/mL (IAV1-3). Cytotoxicity was monitored 24 (D1) and 48 (D2) hours post-inoculation on MucilAir™ 3D media.
Figure 27:
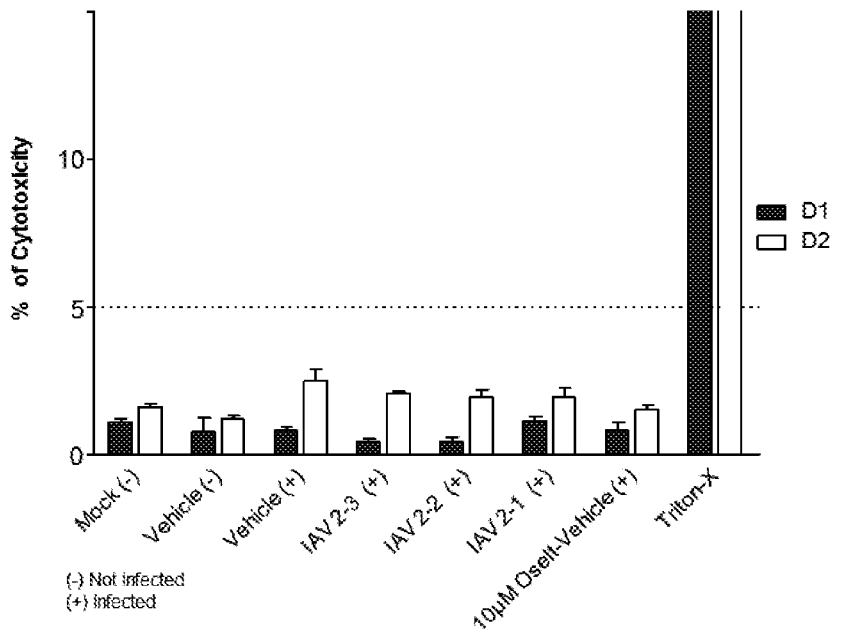
FIG. 27 illustrates the effect of Influenza A H1N1 infection on LDH release from epithelial cells with lysozyme treatment at 2500 μg/mL (IAV2-1), 250 μg/mL (IAV2-2), and 25 μg/mL (IAV2-3). Cytotoxicity was monitored 24 (D1) and 48 (D2) hours post-inoculation on MucilAir™ 3D media.
Figure 28:
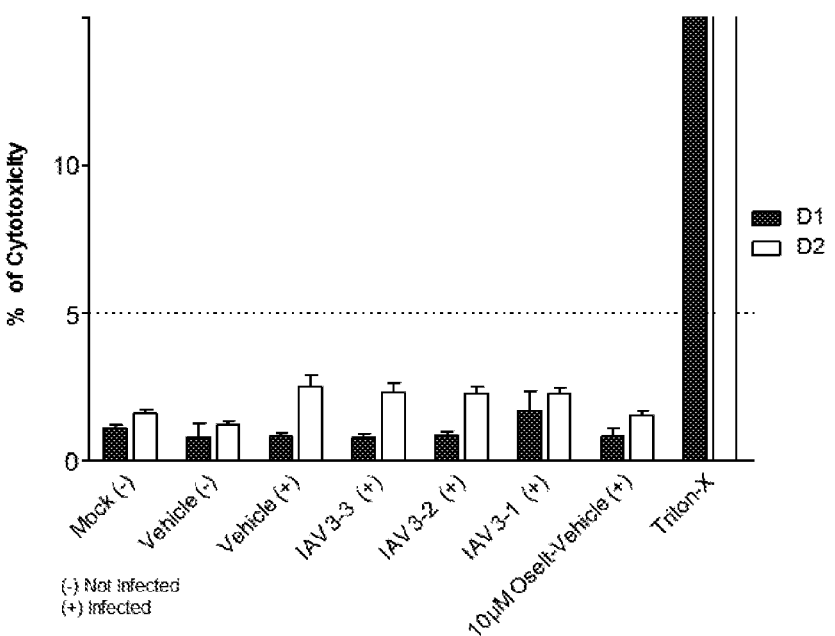
FIG. 28 illustrates the effect of Influenza A H1N1 infection on LDH release from epithelial cells with a combination of 3'-sialyllactose and 6'sialyllactose treatment each at 327 μg/mL (IAV3-1), 3.27 μg/mL (IAV3-2), and 0.327 μg/mL (IAV3-3). Cytotoxicity was monitored 24 (D1) and 48 (D2) hours post-inoculation on MucilAir™ 3D media.
Figure 29:
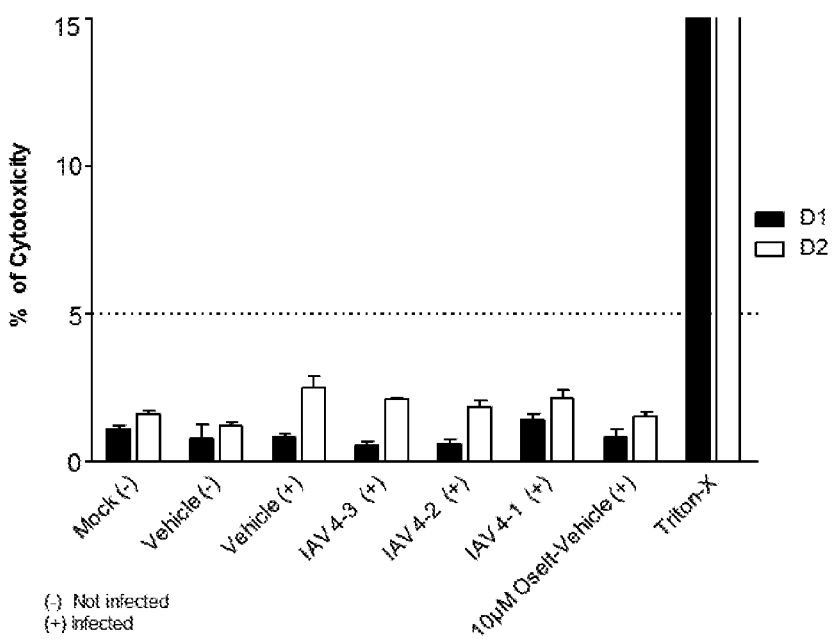
FIG. 29 illustrates the effect of Influenza A H1N1 infection on LDH release from epithelial cells with a combination of apolactoferrin, lysozyme, and sialyllactoses at the three different doses shown in Table 5 (IAV4-1, IAV4-2, and IAV4-3). Cytotoxicity was monitored 24 (D1) and 48 (D2) hours post-inoculation on MucilAir™ 3D media.
Figure 30:
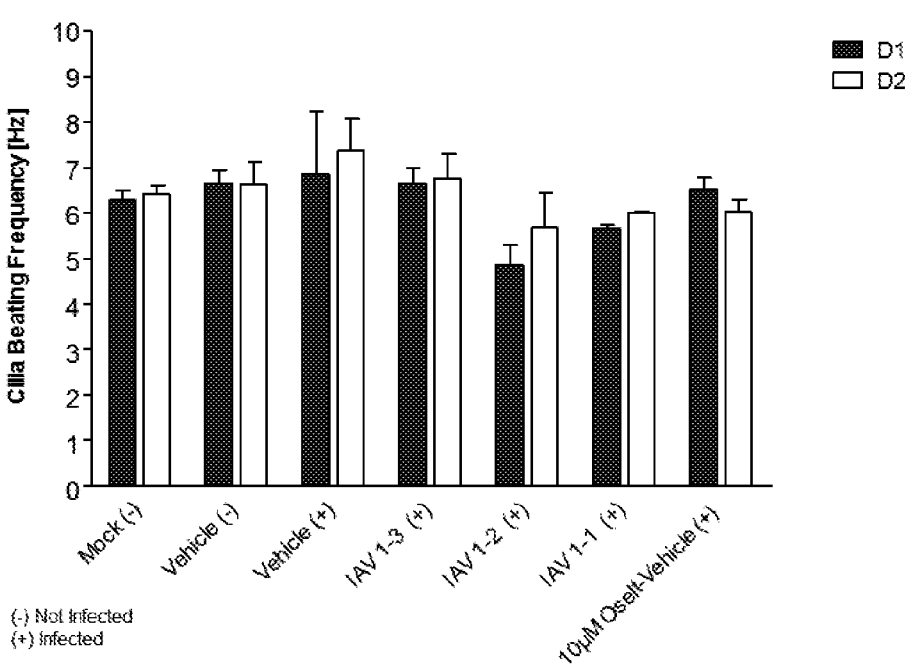
FIG. 30 illustrates the effect of Influenza A H1N1 infection on cilia beating frequency of epithelial cells with apolactoferrin treatment at 500 μg/mL (IAV1-1), 50 μg/mL (IAV1-2), and 5 μg/mL (IAV1-3). Cilia beating frequency was monitored 24 (D1) and 48 (D2) hours post-inoculation on MucilAir™ 3D media.
Figure 31:
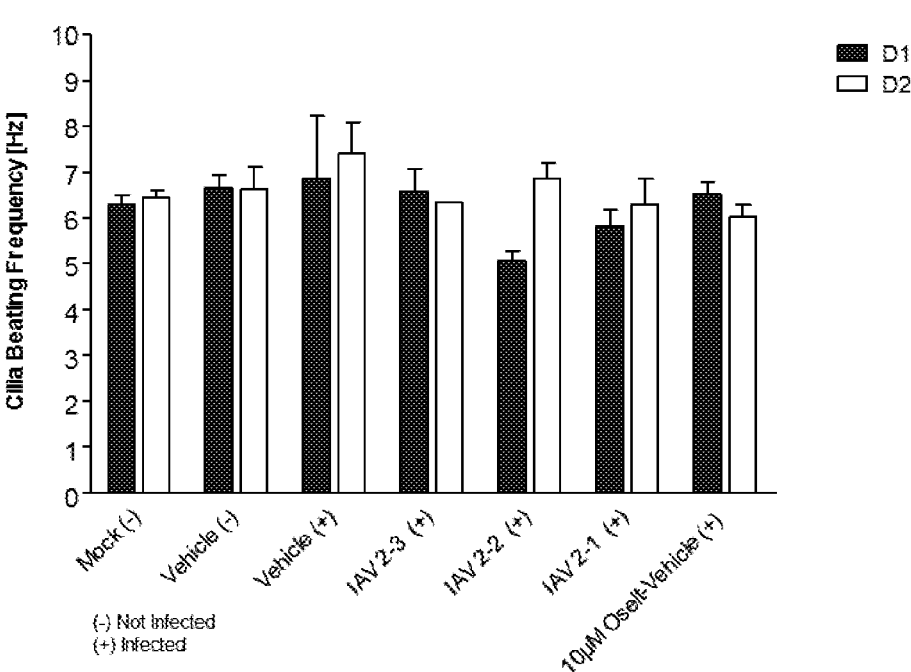
FIG. 31 illustrates the effect of Influenza A H1N1 infection on cilia beating frequency of epithelial cells with lysozyme treatment at 2500 μg/mL (IAV2-1), 250 μg/mL (IAV2-2), and 25 μg/mL (IAV2-3). Cilia beating frequency was monitored 24 (D1) and 48 (D2) hours post-inoculation on MucilAir™ 3D media.
Figure 32:
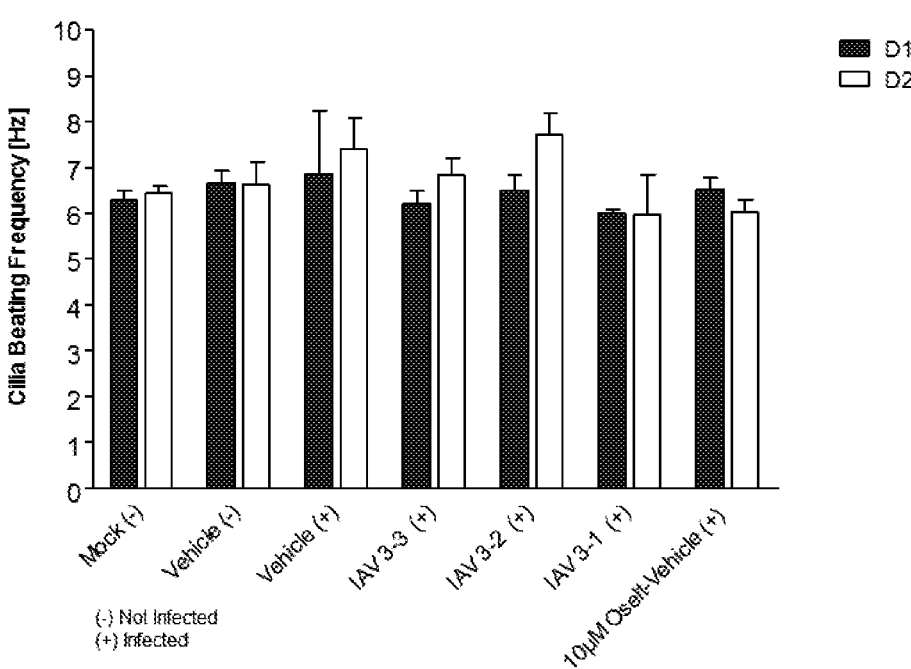
FIG. 32 illustrates the effect of Influenza A H1N1 infection on cilia beating frequency of epithelial cells with a combination of 3'-sialyllactose and 6' sialyllactose treatment each at 327 μg/mL (IAV3-1), 3.27 μg/mL (IAV3-2), and 0.327 μg/mL (IAV3-3). Cilia beating frequency was monitored 24 (D1) and 48 (D2) hours post-inoculation on Muci-lAir™ 3D media.
Figure 33:
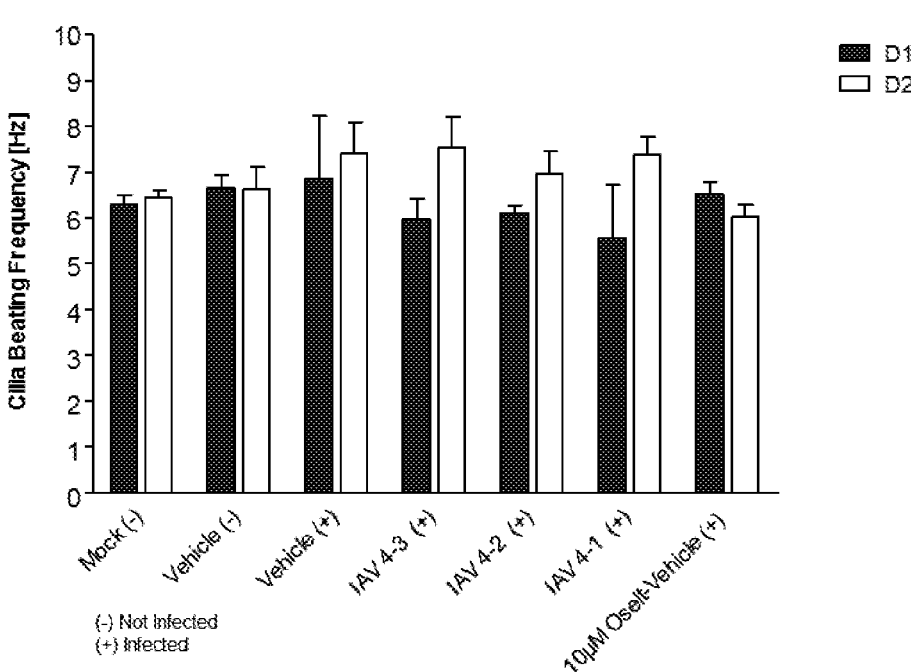
FIG. 33 illustrates the effect of Influenza A H1N1 infection on cilia beating frequency of epithelial cells with a combination of apolactoferrin, lysozyme, and sialyllactoses at the three different doses shown in Table 5 (IAV4-1, IAV4-2, and IAV4-3). Cilia beating frequency was monitored 24 (D1) and 48 (D2) hours post-inoculation on Muci-lAir™ 3D media.
Figure 34:
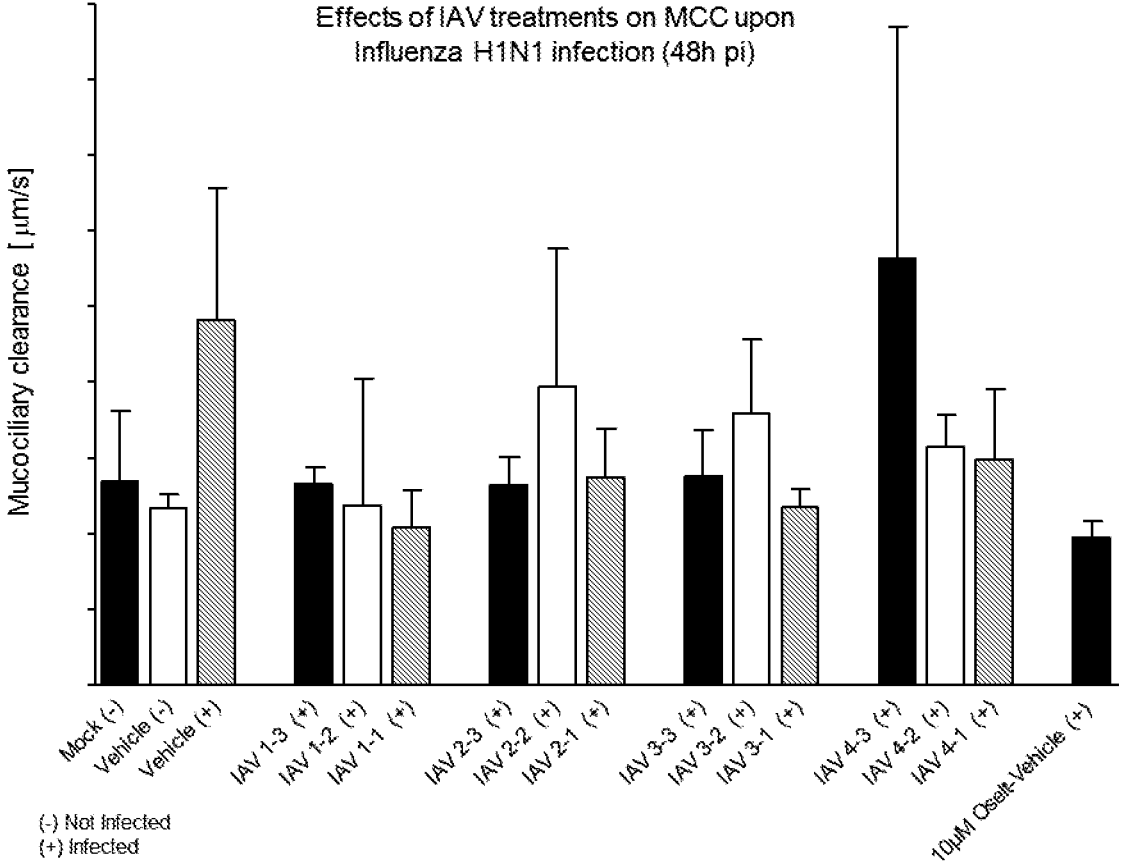
FIG. 34 illustrates the effect of Influenza A H1N1 infection on mucociliary clearance of epithelial cells with IAV treatments. Mucociliary clearance was monitored 48 (D2) hours post-inoculation on MucilAir™ 3D media.
Figure 35:
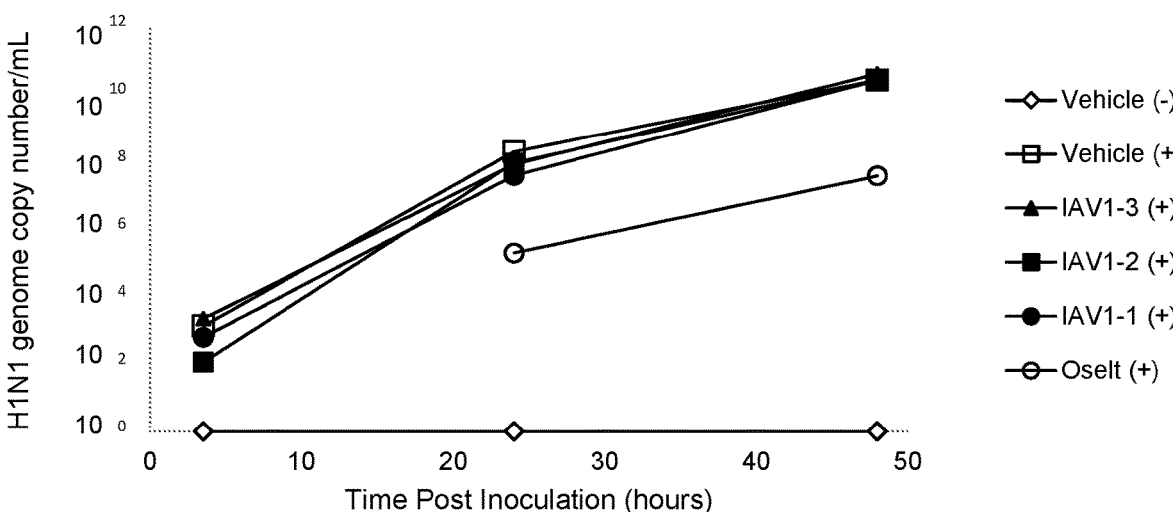
FIG. 35 illustrates the genome copy number of Influenza A H1N1 infection with apolactoferrin treatment at 500 μg/mL (IAV1-1), 50 μg/mL (IAV1-2), and 5 μg/mL (IAV1-3). Viral load was measured at 3.5, 24, and 48 hours post-inoculation on MucilAir™ 3D media.
Figure 36:
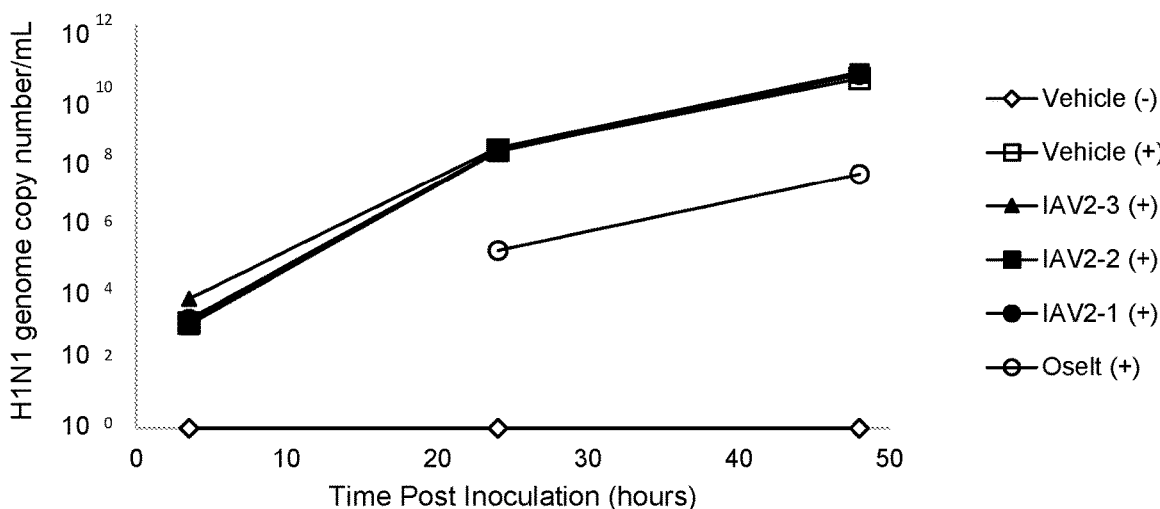
FIG. 36 illustrates the genome copy number of Influenza A H1N1 infection with lysozyme treatment at 2500 μg/mL (IAV2-1), 250 μg/mL (IAV2-2), and 25 μg/mL (IAV2-3). Viral load was measured at 3.5, 24, and 48 hours post-inoculation on MucilAir™ 3D media.
Figure 37:
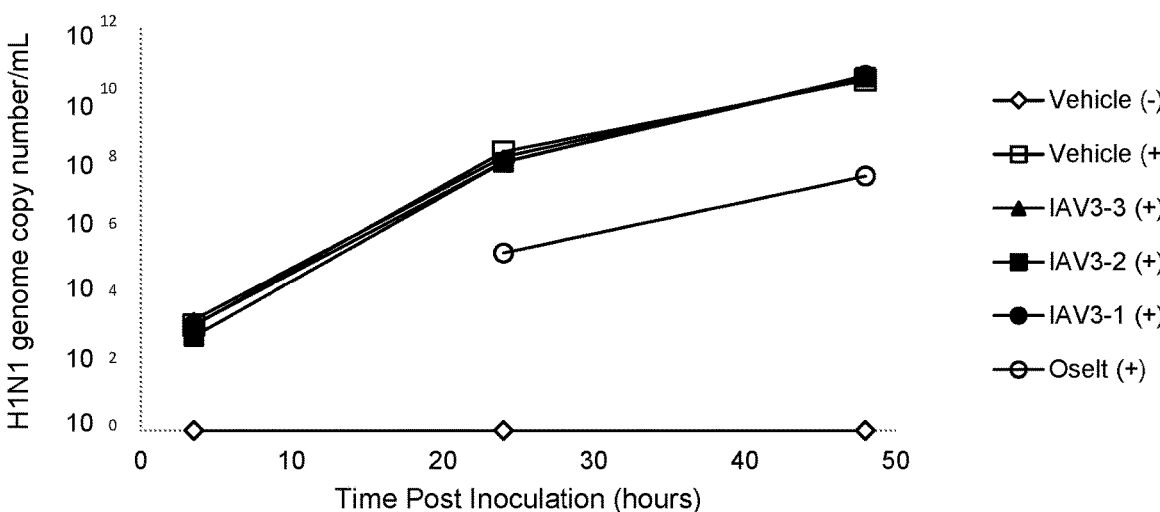
FIG. 37 illustrates the genome copy number of Influenza A H1N1 infection with a combination of 3'-sialyllactose and 6' sialyllactose treatment each at 327 μg/mL (IAV3-1), 3.27 μg/mL (IAV3-2), and 0.327 μg/mL (IAV3-3). Viral load was measured at 3.5, 24, and 48 hours post-inoculation on MucilAir™ 3D media.
Figure 38:
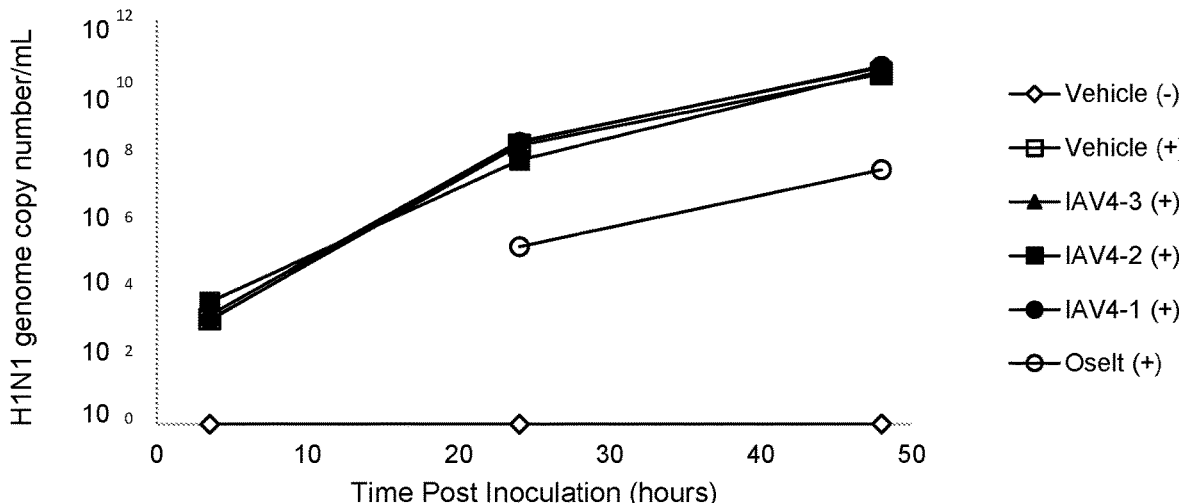
FIG. 38 illustrates the genome copy number of Influenza A H1N1 infection with a combination of apolactoferrin, lysozyme, and sialyllactoses at the three different doses shown in Table 5 (IAV4-1, IAV4-2, and IAV4-3). Viral load was measured at 3.5, 24, and 48 hours post-inoculation on MucilAir™ 3D media.
Figure 39:
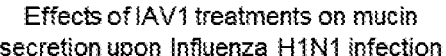
FIG. 39 illustrates the mucin quantity as measured with an ELLA assay from the apical medium with apolactoferrin treatment at 500 μg/mL (IAV1-1), 50 μg/mL (IAV1-2), and 5 μg/mL (IAV1-3) and Influenza A H1N1 infection at 24 (D1) and 48 (D2) hours post-inoculation on MucilAir™ 3D media.
Figure 39:
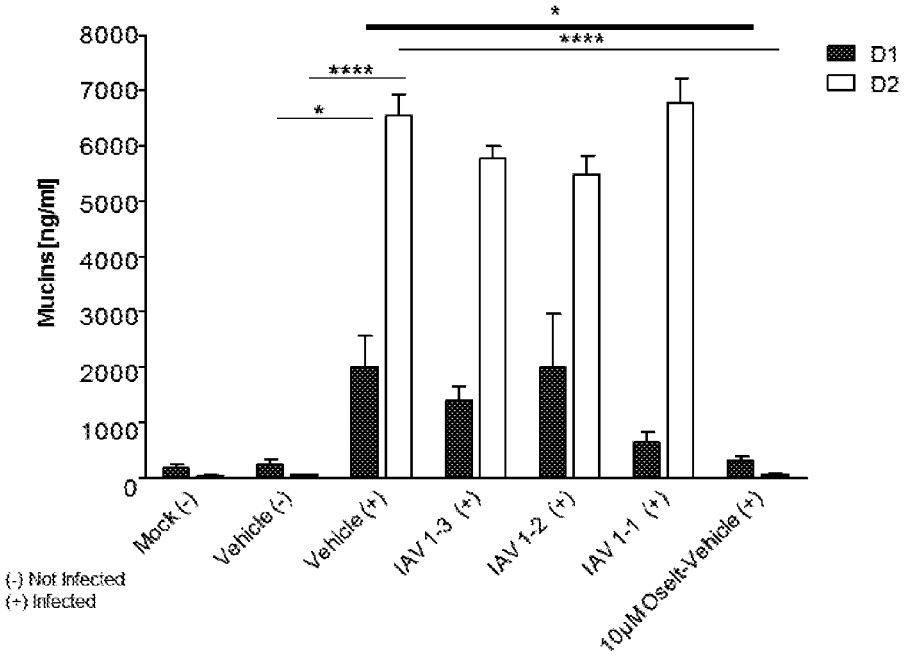
Figure 40:
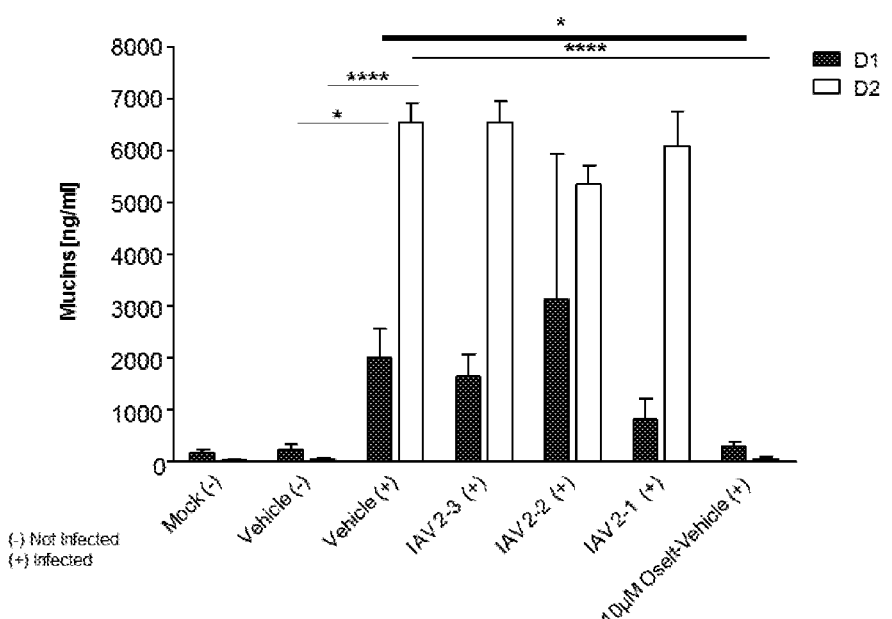
FIG. 40 illustrates the mucin quantity as measured with an ELLA assay from the apical medium with lysozyme treatment at 2500 μg/mL (IAV2-1), 250 μg/mL (IAV2-2), and 25 μg/mL (IAV2-3) and Influenza A H1N1 infection at 24 (D1) and 48 (D2) hours post-inoculation on MucilAir™ 3D media.
Figure 41:
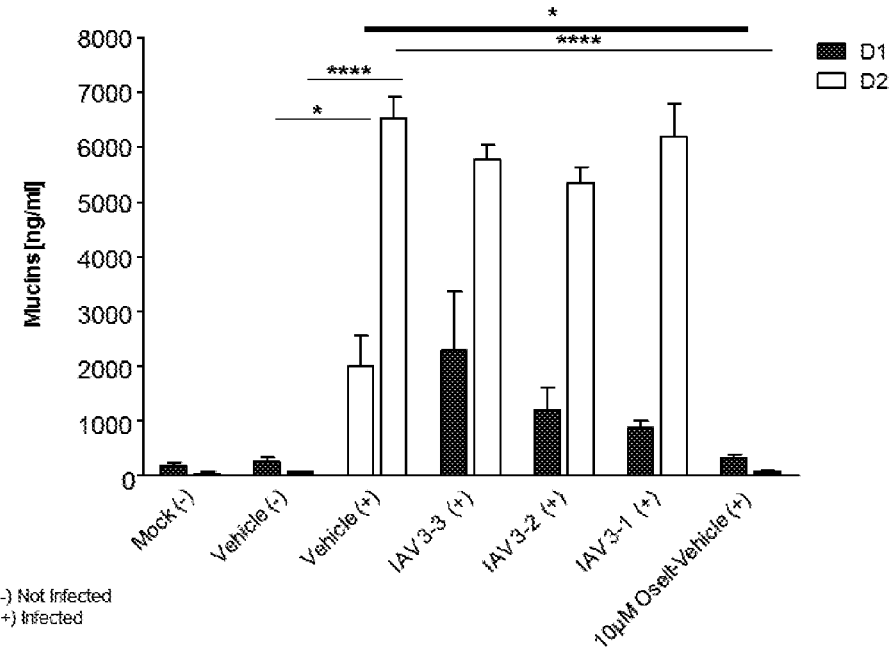
FIG. 41 illustrates the mucin quantity as measured with an ELLA assay from the apical medium with a combination of 3'-sialyllactose and 6' sialyllactose treatment each at 327 μg/mL (IAV3-1), 3.27 μg/mL (IAV3-2), and 0.327 μg/mL (IAV3-3) and Influenza A H1N1 infection at 24 (D1) and 48 (D2) hours post-inoculation on MucilAir™ 3D media.
Figure 42:
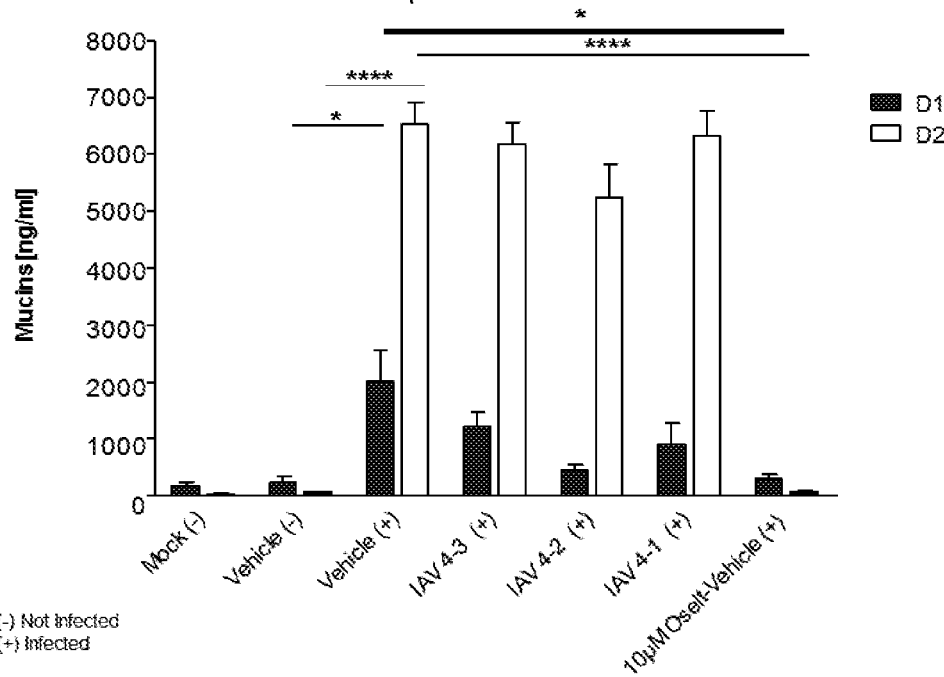
FIG. 42 illustrates the mucin quantity as measured with an ELLA assay from the apical medium with a combination of apolactoferrin, lysozyme, and sialyllactoses at the three

FIG. 34 illustrates the results on mucociliary clearance after treatment with the specified test formulations. As can be seen, the IAV formulations showed no significant effect on mucociliary clearance.

Apical Influenza Replication

From the 200 µL apical washes, 20 µL was used for viral RNA extraction with the QIAamp® Viral RNA kit (Qiagen) resulting in 60 µL RNA elution volume. Viral RNA was quantified by quantitative RT-PCR (QuantiTect Probe RT-PCR, Qiagen) using 5 µL of viral RNA, Mastermix, two Influenza A specific primers and Influenza A probe with FAM-BHQ1 reporter-quencher dyes. Four dilutions of known concentration of H1N1 as well as controls for RNA extraction and RT-PCR were included and the plates were run on a TaqMan ABI 7000 from Applied Biosystems. Ct data were reported to the standard curve, corrected with the dilutions and presented as genome copy number/mL. FIGS. 35-38 illustrate the results of Influenza A H1N1 replication in presence of the specified test formulation. As can be seen Influenza showed a significant replication which was inhibited by Oseltamivir. No significant change in Influenza A H1N1 replication was achieved using IAV formulations.

Enzyme-Linked Lectin Assay

FIGS. 39-42 illustrate the mucin quantity from the apical medium at 24 (D1) and 48 (D2) hours pi. As can be seen, IAV4 showed a dose dependent response in mucin secretion.

As shown by TEER measurements, H1N1 infection results in a loss of tissue integrity on human airway epithelia resulting in the breakdown of the barrier function of the airway. This results in further infection and inflammation. A decrease of TEER is the earliest and most sensitive parameter affected by H1N1 infection. Combination formulations IAV3 and IAV4 resulted in the partial mitigation of this breakdown of tissue integrity. Additionally, these formulations prevented any of the negative effects on CBF that was seen in IAV1 and IAV2 formulations.

Example 6: Measurements of Compositions on Full Differentiated 3D Cell Model of the Human Airway Epithelia Inoculated with Rhinovirus A16

Epithelia (MucilAir™-Pool) were reconstituted with a mixture of cells isolated from 14 different normal nasal donors and cultured for 41 days. Compositions with various active ingredients were prepared as shown in Table 7. Each composition was prepared in a buffered saline solution (3.6% NaCl, 5.00 mM $CaCl_2$, 40 mM HEPES). As used herein, compositions names may indicate each active ingredient (separated by "+" signs), wherein each individual active ingredient is designated by "R1," "R2," "R3," or "R4." As used herein, the "L" and "H" designations in composition names, when present, refer to lower and higher concentrations of the indicated component, respectively, comparative of one another (i.e., [R1L]<[R1H]). For example, the composition identified as "R1L+R2H" is intended to indicate the composition has active ingredient R1 (i.e., apolactoferrin) and active ingredient R2 (i.e., lysozyme) at the concentrations indicated. As used herein, "R1" in a composition name refers to compositions comprising apolactoferrin (i.e., R1L, R1H, R1H+R2H, R1H+R2L, R1H+R3H, R1L+R2L+R3H, R1L+R2L+R4H), reference to "R2" and refers to compositions comprising lysozyme (i.e., R2L, R2H, R1H+R2H, R1L+R2L, R1H+R2L, R1L+R2H, R2H+R3H), reference to "R3" refers to compositions comprising soluble ICAM-1 available from RnD Biosystems (i.e., R3, R1H+R3, and R1L+R2L+R3), and reference to "R4" refers to compositions comprising soluble ICAM-1 available from Planet Biotechnology (i.e., R4, R1H+R4, and R1L+R2L+R4). These various test formulations are shown below in Table 7.

TABLE 7

| Composition Name | Active Ingredients (Concentration) |
| --- | --- |
| R1H | Apolactoferrin (1 mg/mL) |
| R1L | Apolactoferrin (0.5 mg/mL) |
| R2H | Lysozyme (5 mg/mL) |
| R2L | Lysozyme (2.5 mg/mL) |
| R3 | soluble ICAM-1 (0.5 mg/mL) |
| R4 | sICAM-1 (0.5 mg/mL) |
| R1H+R2H | Apolactoferrin (1 mg/mL) |
| | Lysozyme (5 mg/mL) |
| R1L+R2L | Apolactoferrin (0.5 µg/mL) |
| | Lysozyme (2.5 mg/mL) |
| R1H+R2L | Apolactoferrin (1 mg/mL) |
| | Lysozyme (2.5 mg/mL) |
| R1L+R2H | Apolactoferrin (0.5 µg/mL) |
| | Lysozyme (5 mg/mL) |
| R2H+R3 | Lysozyme (5 mg/mL) |
| | soluble ICAM-1 (0.5 mg/mL) |
| R1L+R2L+R3 | Apolactoferrin (0.5 mg/mL) |
| | Lysozyme (2.5 mg/mL) |
| | soluble ICAM-1 (0.5 mg/mL) |
| R1L+R2L+R4 | Apolactoferrin (0.5 mg/mL) |
| | Lysozyme (2.5 mg/mL) |
| | soluble ICAM-1 (0.5 mg/mL) |

To compare the potential effects of compositions, positive controls were included. For a control of the toxic effect ("Vehicle (+)"), virus cultures were treated with 10% Triton X-100 in a buffered saline solution (0.9% NaCl, 1.25 mM $CaCl_2$, 0 mM HEPES). For the antiviral control, 5 µM Rupintrivir ("Rup") was added to basal medium and vehicle to the apical side. Rupintrivir (Santa Cruz Biotechnologies) stock solution of 2 mM in DMSO (–20° C.) was diluted to 5 µM in MucilAir™ medium (0.25% DMSO final concentration).

20 µL of each formulation was applied apically onto separate MucilAir™-Pools immediately prior to inoculation (time=0) with Human Rhinovirus-A16. 20 µL of the each of the formulations was also applied at 3.5 and 24 hours post-inoculation ("pi") after the apical washing of the medium at each time point as described below. Inoculation with Human Rhinovirus-A16 was achieved by the application of 50 µL of 2×10⁶/mL Human Rhinovirus A16 (clinical strain: QCHRV.16) on the apical side of the 3D model for 3 h at 34° C., 5% $CO_2$. The virus stocks were produced in MucilAir™ cultures and diluted in culture medium without purification or concentration.

After inoculation (time=0), epithelia were washed three times with MucilAir™ culture medium in order to clean the inoculum. This washing eliminates all viral particles that have not been processed by the tissue to avoid any contamination during further quantification of active virus production (next measure at 24 hours). Wash efficiency may be characterized by the genome copy measurement at 3.5 hours (see FIGS. 43 and 44). Cell free, apical washes (20 minutes) with 200 µL MucilAir™ culture media were collected at 3.5 hours post-inoculation and then at 24 and 48 hours pi and stocked at −80° C. for further measurements.

Apical Rhinovirus Replication

From the 200 µL apical washes, 20 µL was used for viral RNA extraction with the QIAamp® Viral RNA kit (Qiagen) resulting in 60 µL RNA elution volume. Viral RNA was quantified by quantitative RT-PCR (QuantiTect Probe RT-PCR, Qiagen) using 5 µL of viral RNA, Mastermix (two Picornaviridae family specific and a Pan-Picornaviridae primers, and a Picornaviridae probe with FAM-TAMRA reporter-quencher dyes). Four dilutions of known concentration of known concentration of Rhinovirus A16 as well as controls for RNA extraction and RT-PCR were included and the plates were run on a TaqMan ABI 7000 from Applied Biosystems. Ct data were reported to the standard curve, corrected with the dilutions and presented as genome copy number/mL. FIGS. 43-46 illustrate the results of Rhinovirus A16 replication in presence of the specified test formulation. The quantified concentration of the Rhinovirus A16 inoculation was 3.73×10⁶/mL (planned 2×10⁶/mL). As can be seen Rhinovirus showed a significant replication which was inhibited by Rupintrivir.

At 24 hours pi ("D1"), soluble ICAM-1 has inhibited replication of HRV-A16 virus. However, this effect of compositions with soluble ICAM-1 as the sole antiviral agent (formulation R3 or formulation R4) appears to have diminished at 48 hours ("D2"). When soluble ICAM-1 is mixed with apolactoferrin (formulation R1H+R3), lysozyme (formulation R2H+R3), or apolactoferrin and lysozyme (formulation R1L+R2L+R3), the inhibitory effect persists at D2.

Mucociliary Clearancy (MCC)

The mucociliary clearance was monitored using a MAKO G030B camera (Allied Vision) connected to a Leica DMIRE2 microscope with a 5× objective. Polystyrene microbeads of 30 µm diameter (Sigma, cat. no. 84135) were added on the apical surface of the MucilAir™ medium. Microbead movements were video tracked at 2 frames per second for 30 images at 34° C. A representative collection of images is shown in FIGS. 47A and 47B. FIG. 47A shows representatives images from the tracked position (represented by each line) of the microbeads for Vehicle(−). FIG. 47B shows representative images from tracking analysis for Formulation R1L+R2L+R4. The scale bar represents 100 µm. Three movies were taken per insert. The average bead movement velocity (µm/sec) for each formulation was calculated with ImageProPlus 6.0 software. The results for each formulation are shown in FIG. 48. As can be seen, the formulations do not provide a significant change in the measured mucociliary clearance.

Lactate Dehydrogenase (LDH) Release

Lactate dehydrogenase is a stable cytoplasmic enzyme that is rapidly released into the culture medium upon rupture of the plasma membrane. 100 µL basolateral medium is collected at 24 and 48 hour pi and incubating with the reaction mixture of the Cytotoxicity Detection KitPLUS, following manufacturer's instructions (Sigma, Roche, 11644793001). The amount of the released LDH was quantified using the absorbance of each sample at 490 nm with a microplate reader. The high control value was obtained by 10% Triton X-100 treatment 24 hours prior to the assay and corresponds to 100% cytotoxicity. The negative controls (Mock (−) and Vehicle (−) correspond to a physiological release of LDH in MucilAir™. FIG. 49 illustrates the results of LDH release from the epithelial cells. As can be seen, no cytotoxic effect was observed for any of the formulations.

Example 7: Measurements of Compositions on Full Differentiated 3D Cell Model of the Human Airway Epithelia Inoculated with Influenza H1N1

Epithelia (MucilAir™-Pool) were reconstituted with a mixture of cells isolated from 14 different normal nasal donors and cultured for 41 days. Compositions with various active ingredients were prepared as shown in Table 8. Each composition was prepared in a buffered saline vehicle (3.6% NaCl, 5.00 mM $CaCl_2$), 40 mM HEPES). As used herein, compositions names may indicate each active ingredient (separated by "+" signs), wherein each individual active ingredient is designated by "I1," "I2," "I3," or "I4." For example, the composition identified as "I1+I2" is intended to indicate the composition has active ingredient I1 (i.e., apolactoferrin) and active ingredient I2 (i.e., lysozyme) at the concentrations indicated. As used herein, "I1" in a composition name refers to compositions comprising apolactoferrin (i.e., I1, I1+I2, I1+I3, I1+I2+I3, I1+I2+I4, I1+I2+I3+I4), reference to "I2" and refers to compositions comprising lysozyme (i.e., I2, I1+I2, I2+I3, I1+I2+I3, I1+I2+I4, I1+I2+I3+I4), reference to "I3" refers to compositions comprising sialic acids (i.e., I3, I1+I3, I2+I3, I1+I2+I3, I1+I3+I4, I2+I3+I4, I3+I4, and I1+I2+I3+I4), and reference to "I4" refers to compositions comprising a neuraminidase inhibitor (i.e., I4, I2+I4, I3+I4, I1+I2+I4, I1+I3+I4, I2+I3+I4, I1+I2+I3+I4). These various test formulations are shown below in Table 7.

TABLE 8

| Composition Name | Active Ingredients (Concentration) |
|---|---|
| I1 | Apolactoferrin (0.5 mg/mL) |
| I2 | Lysozyme (10 mg/mL) |
| I3 | 6'-sialyllactose (0.5 mg/mL) |
| | 3'-sialyllactose (0.5 mg/mL) |
| I4 | Isoquercetin (1 µM) |
| I1+I2 | Apolactoferrin (0.5 mg/mL) |
| | Lysozyme (10 mg/mL) |
| I1+I3 | Apolactoferrin (0.5 mg/mL) |
| | 6'-sialyllactose (0.5 mg/mL) |
| | 3'-sialyllactose (0.5 mg/mL) |
| I1+I4 | Apolactoferrin (1 mg/mL) |
| | Isoquercetin (1 µM) |
| I2+I3 | Lysozyme (10 mg/mL) |
| | 6'-sialyllactose (0.5 mg/mL) |
| | 3'-sialyllactose (0.5 mg/mL) |
| I2+I4 | Lysozyme (10 mg/mL) |
| | Isoquercetin (1 µM) |
| I3+I4 | 6'-sialyllactose (0.5 mg/mL) |
| | 3'-sialyllactose (0.5 mg/mL) |
| | Isoquercetin (1 µM) |
| I1+I2+I3 | Apolactoferrin (0.5 mg/mL) |
| | Lysozyme (10 mg/mL) |
| | 6'-sialyllactose (0.5 mg/mL) |
| | 3'-sialyllactose (0.5 mg/mL) |

TABLE 8-continued

| Composition Name | Active Ingredients (Concentration) |
|---|---|
| I1+I2+I4 | Apolactoferrin (0.5 mg/mL) |
| | Lysozyme (10 mg/mL) |
| | Isoquercetin (1 μM) |
| I1+I3+I4 | Apolactoferrin (0.5 mg/mL) |
| | 6'-sialyllactose (0.5 mg/mL) |
| | 3'-sialyllactose (0.5 mg/mL) |
| | Isoquercetin (1 μM) |
| I2+I3+I4 | Lysozyme (10 mg/mL) |
| | 6'-sialyllactose (0.5 mg/mL) |
| | 3'-sialyllactose (0.5 mg/mL) |
| | Isoquercetin (1 μM) |
| I1+I2+I3+I4 | Apolactoferrin (0.5 mg/mL) |
| | Lysozyme (10 mg/mL) |
| | 6'-sialyllactose (0.5 mg/mL) |
| | 3'-sialyllactose (0.5 mg/mL) |
| | Isoquercetin (1 μM) |

To compare the potential effects of compositions, positive controls were included. For a control of the toxic effect ("Vehicle (+)"), virus cultures were treated with 10% Triton X-100 in a buffered saline solution (0.9% NaCl, 1.25 mM $CaCl_2$), 10 mM HEPES). For the antiviral control, 14 μM Oseltamivir ("Oselt") was added to basal medium and vehicle to the apical side. Oseltamivir acid (Carbosynth) stock solution of 4 mM in DMSO (−20° C.) was diluted to 10 μM in MucilAir™ basolateral medium (0.25% DMSO final concentration).

22 μL of each formulation was applied apically onto separate MucilAir™-Pools immediately prior to inoculation (time=0) with Influenza H1N1. 22 μL of the each of the formulations was also applied at 3.5 and 24 hours post-inoculation ("pi") after the apical washing of the medium at each time point as described below. Inoculation with Influenza H1N1 was achieved by the application of 50 μL of $2 \times 10^6$/mL Influenza H1N1 (clinical strain: A/California/7/09) on the apical side of the 3D model for 45 minutes at 34° C., 5% $CO_2$. The virus stocks were produced in MucilAir™ cultures and diluted in culture medium without purification or concentration.

After inoculation (time=0), epithelia were washed three times with MucilAir™ culture medium in order to clean the inoculum. This washing eliminates all viral particles that have not been processed by the tissue to avoid any contamination during further quantification of active virus production (next measure at 24 hours). Wash efficiency may be characterized by the genome copy measurement at 3.5 hours (see FIGS. 43 and 44). Cell free, apical washes (20 minutes) with 200 μL MucilAir™ culture media were collected at 3.5 hours post-inoculation and then at 24 and 48 hours pi and stocked at −80° C. for further measurements.

Apical Influenza Replication

From the 200 μL apical washes, 20 μL was used for viral RNA extraction with the QIAamp® Viral RNA kit (Qiagen) resulting in 60 μL RNA elution volume. Viral RNA was quantified by quantitative RT-PCR (QuantiTect Probe RT-PCR, Qiagen). For dilutions of known concentration H1N1 as well as controls for RNA extraction and RT-PCR were included and the plates were run on a Chromo4 PCR Detection System from Bio-Rad. Ct data were reported to the standard curve, corrected with the dilutions and presented as genome copy number/mL. The quantified concentration of the Rhinovirus A16 inoculation was $7.93 \times 10^5$/mL (planned $2 \times 10^6$/mL). FIG. 50 illustrates the Influenza H1N1 replication in presence of the specified test formulation as measured from the apical washes. FIG. 51 illustrates the Influenza H1N1 replication in presence of the specified test formulation as measured from the basal medium. In FIGS. 50 and 51, statistical significance is shown in relation to the Vehicle(+) measurement at the specified time point. The quantified concentration of the Rhinovirus A16 inoculation was $3.73 \times 10^6$/mL (planned $2 \times 10^6$/mL).

As can be seen in FIG. 50, I1+I2 (apolactoferrin and lysozyme), I1+I2+I3 (apolactoferrin, lysozyme, and sialic acids) and I1+I2+I3+I4 (apolactoferrin, lysozyme, sialic acids, and isoquercetin) formulations inhibit H1N1 replication statistically. Moreover, these inhibitory effects are not present in the formulations comprising each individual ingredient alone. However, due only to the very high titer of H1N1 in the MucilAir™ cultures, this inhibitory effect of the formulations is mitigated at D2. In FIG. 51, the basal medium which has a delayed H1N1 release, similar inhibitory effects of these formulations are seen.

TEER Measurements

FIG. 52 illustrates the results of TEER measurements with Influenza A H1N1 and the specified formulations. As can be seen, the cytopathic effect of the influenza virus does not appear to cause TEER diminution, possibly due to the inoculation duration. However, the formulations comprising I4 (isoquercetin) show a slight reduction in resistance as compared to Vehicle(+) at D2.

Lactate Dehydrogenase (LDH) Release

FIG. 53 illustrates the results of LDH release from the epithelial cells exposed to Influenza H1N1 and the specified formulation. As can be seen, the decrease in TEER for several formulations with isoquercetin correlates with an increase in cytotoxic effect at D2. However, the combination formulation I1+I2+I3+I4 (apolactoferrin, lysozyme, sialic acids, isoquercetin), prevents the H1N1 induced increased in cytotoxicity beyond the 5% threshold limit. This effect is not seen in the other formulations comprising isoquercetin.

Having thus described in detail a number of preferred embodiments of the present disclosure, it is to be understood that the disclosure defined by the above paragraphs is not to be limited to particular details set forth in the above description, as many apparent variations thereof are possible without departing from the spirit or scope of the present disclosure.

All documents cited or referenced herein and all documents cited or referenced in the herein cited documents, together with any manufacturer's instructions, descriptions, product specifications, and product sheets for any products mentioned herein or in any document incorporated by reference herein, are hereby incorporated by reference, and may be employed in the practice of the disclosure.

The invention claimed is:

1. A method of protecting the epithelial and mucous membranes of a subject from viral respiratory infection comprising administration of a pharmaceutical composition to the subject having a residence time on the oral mucosa of at least 5 minutes, wherein said pharmaceutical composition comprises a pharmaceutically acceptable carrier and:
   a) lysozyme; and
   b) lactoferrin,
the pharmaceutical composition is in the form of a nasal spray, oral spray, oral rinse, or lozenge, and said composition is isotonic to the nasal epithelia or mucous membrane; wherein administration of the pharmaceutical composition to the subject inhibits the viral respiratory infection on the epithelial and/or mucous membranes, a weight ratio of lactoferrin:lysozyme of about 1:4 to about 1:25.

2. The method according to claim 1, wherein the viral respiratory infection is rhinovirus or influenza.

3. The method according to claim 1, wherein the pharmaceutical composition further comprises sialic acid and/or soluble ICAM-1.

4. The method according to claim 1, wherein the pharmaceutical composition is in the form of a lozenge.

5. The method according to claim 1, wherein the carrier at 25° C. has the Hansen Solubility Parameters of an energy from dispersion ($\delta_d$) of between about 15 and about 18, an energy from dipolar intermolecular force between molecules ($\delta_p$) of between about 15 and about 15, and energy from hydrogen bonds ($\delta_h$) of between about 21 and about 25.

6. The method according to claim 5, wherein the pharmaceutically acceptable carrier comprises a mixture of water and propanediol or a mixture of water and glycerin.

7. The method according to claim 1, wherein the weight ratio of lactoferrin to lysozyme is from 1:5 to 1:20.

8. The method according to claim 1, wherein the composition does not comprise carrageenan.

\* \* \* \* \*